(12) United States Patent
Shachar et al.

(10) Patent No.: US 8,684,010 B2
(45) Date of Patent: Apr. 1, 2014

(54) DIAGNOSTIC AND THERAPEUTIC MAGNETIC PROPULSION CAPSULE AND METHOD FOR USING THE SAME

(75) Inventors: Yehoshua Shachar, Santa Monica, CA (US); Laszlo Farkas, Ojai, CA (US); Bruce E. Marx, Ojai, CA (US); David Johnson, West Hollywood, CA (US); Shawn Hakim, Northridge, CA (US); Winston Wu, Alhambra, CA (US)

(73) Assignee: Magnetecs Corporation, Inglewood, CA (US)

( * ) Notice: Subject to any disclaimer, the term of this patent is extended or adjusted under 35 U.S.C. 154(b) by 669 days.

(21) Appl. No.: 12/963,502

(22) Filed: Dec. 8, 2010

(65) Prior Publication Data

US 2011/0301497 A1 Dec. 8, 2011

Related U.S. Application Data

(60) Provisional application No. 61/267,663, filed on Dec. 8, 2009.

(51) Int. Cl.
*A61B 19/00* (2006.01)

(52) U.S. Cl.
USPC .......................................................... 128/899

(58) Field of Classification Search
CPC .................................. A61B 5/06; A61B 5/062
USPC .......... 128/899; 600/117, 118, 160, 178, 424; 600/476; 335/299
See application file for complete search history.

(56) References Cited

U.S. PATENT DOCUMENTS

| | | |
|---|---|---|
| 7,122,001 B2 | 10/2006 | Uchiyama |
| 7,173,507 B2 | 2/2007 | Ries |
| 7,398,117 B2 | 7/2008 | Minai |
| 7,637,864 B2 | 12/2009 | Yokoi |
| 7,663,458 B2 | 2/2010 | Reinschke |
| 2004/0181127 A1 | 9/2004 | Matsumoto |
| 2006/0224063 A1 | 10/2006 | Segawa |
| 2007/0016006 A1* | 1/2007 | Shachar ........................ 600/424 |
| 2007/0219405 A1 | 9/2007 | Uchiyama |
| 2007/0265496 A1 | 11/2007 | Kawano |
| 2007/0299550 A1* | 12/2007 | Nishijima et al. .............. 700/61 |
| 2008/0281188 A1 | 11/2008 | Aoki |
| 2008/0294006 A1* | 11/2008 | Uchiyama et al. ............ 600/118 |
| 2009/0093678 A1 | 4/2009 | Kimura |
| 2009/0253954 A1 | 10/2009 | Katayama |
| 2010/0001592 A1 | 1/2010 | Kawano |
| 2010/0030026 A1 | 2/2010 | Uchiyama |
| 2010/0305402 A1* | 12/2010 | Shachar et al. ............... 600/118 |

* cited by examiner

*Primary Examiner* — Jacqueline Cheng
*Assistant Examiner* — Kaylee Wilson
(74) *Attorney, Agent, or Firm* — Marcus C. Dawes; Daniel L. Dawes

(57) ABSTRACT

A guided medical propulsion capsule driven by strong electro-magnetic interaction between an external AC/DC magnetic gradient-lobe generator and a set of uniquely magnetized ferrous-conductive elements contained within the capsule. The capsule is navigated through the lumens and cavities of the human body wirelessly and without any physical contact for medical diagnostic, drug delivery, or other procedures with the magnetically guiding field generator external to the human body. The capsule is equipped with at least two sets of magnetic rings, disks and/or plates each possessing anisotropic magnetic properties. The external magnetic gradient fields provide the gradient forces and rotational torques on the internal conductive and magnetic elements needed to make the capsule move, tilt, and rotate in the body lumens and cavities according to the commands of an operator.

17 Claims, 51 Drawing Sheets

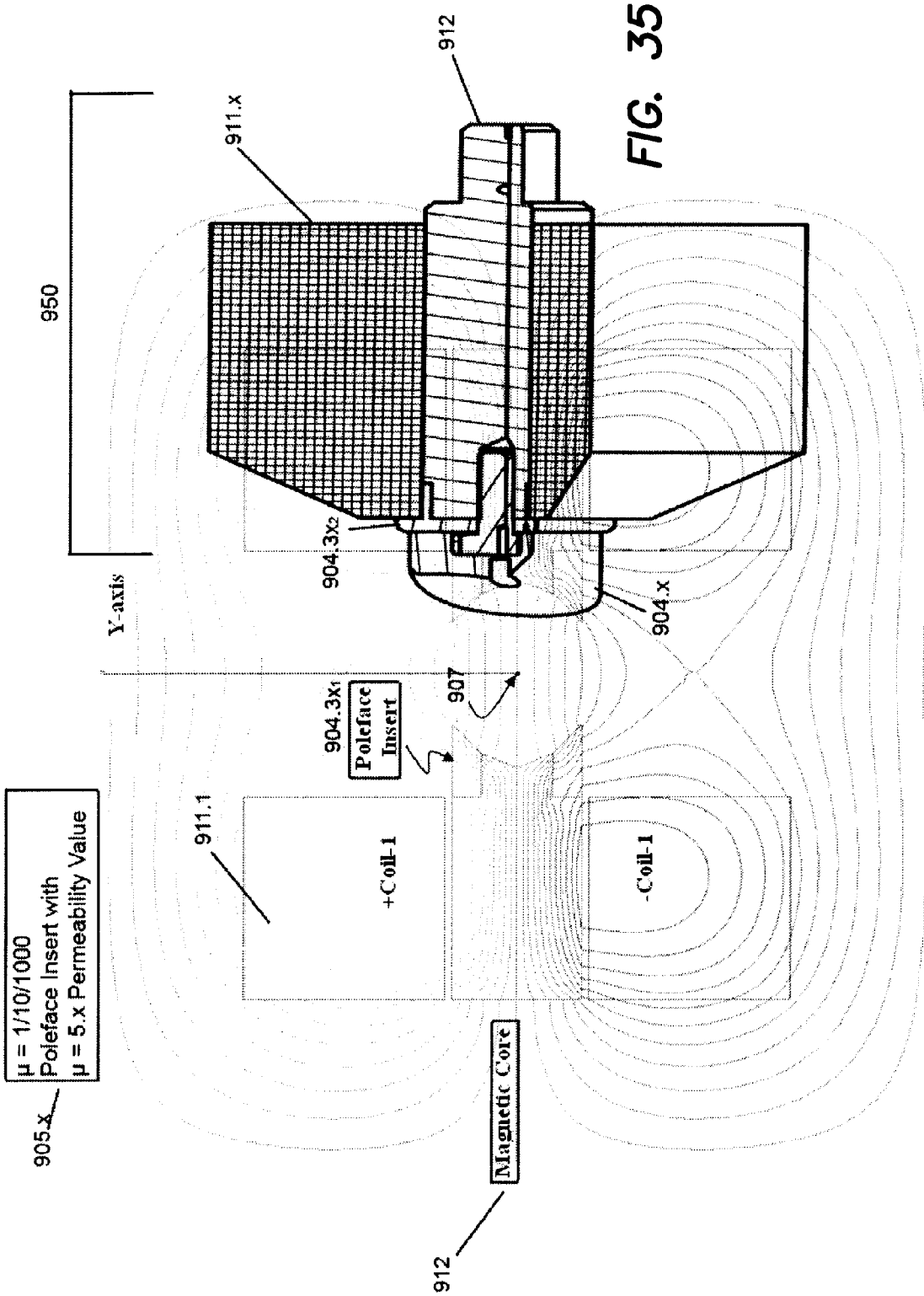

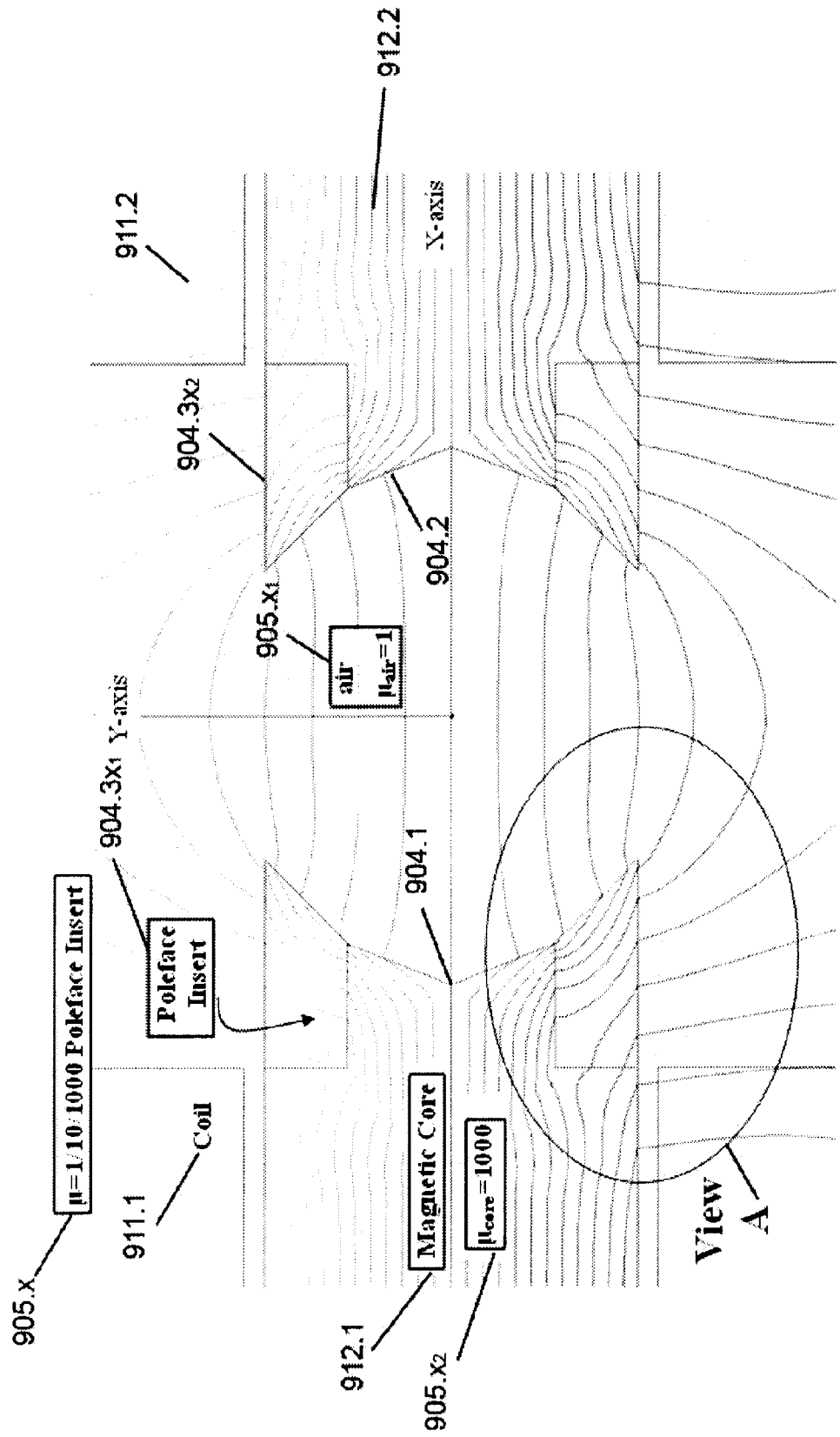

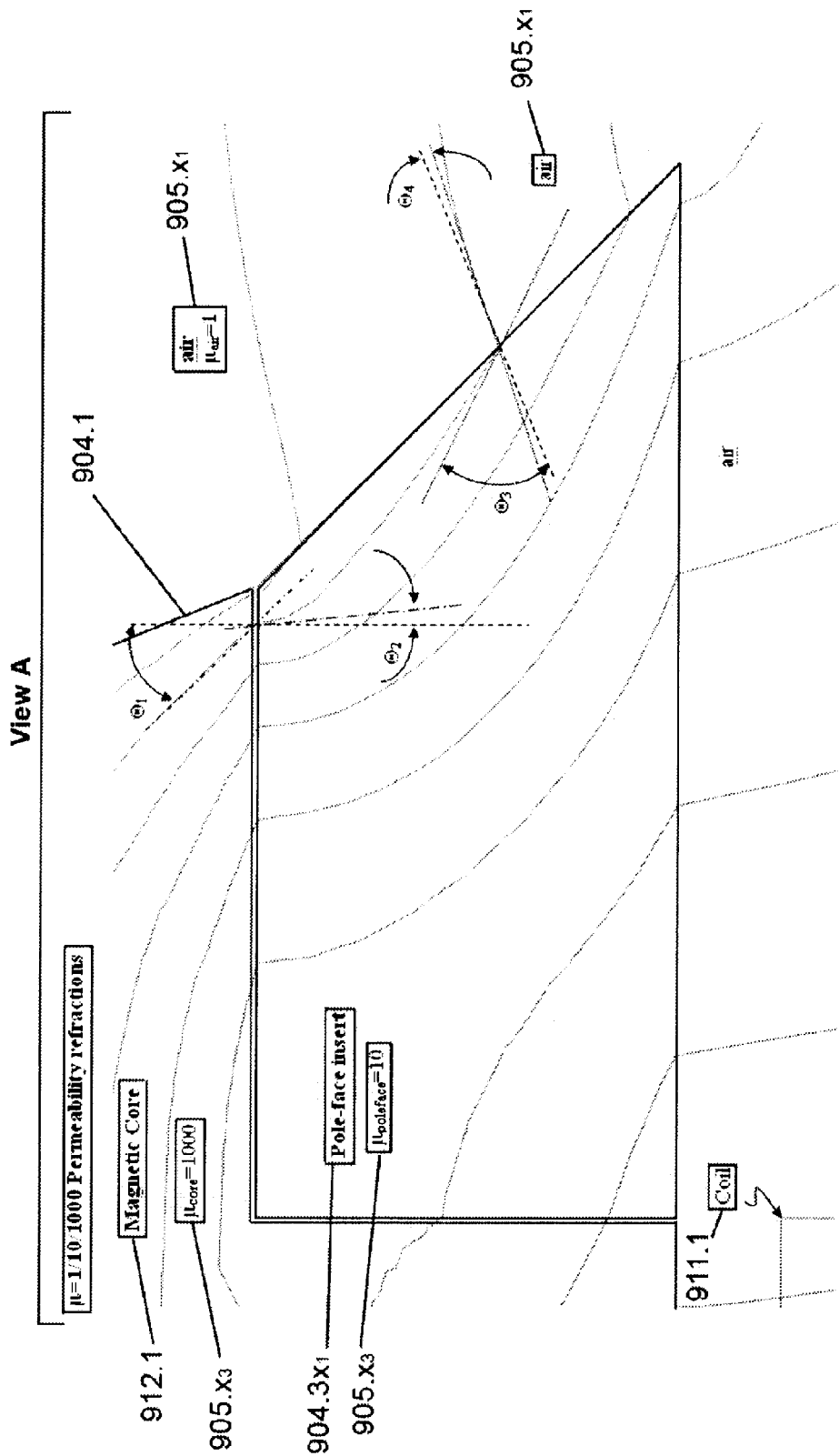

DIAGNOSTIC AND THERAPEUTIC MAGNETIC PROPULSION CAPSULE AND METHOD FOR USING THE SAME

RELATED APPLICATIONS

The present application is related to U.S. Provisional Patent Application, Ser. No. 61/267,663, filed on Dec. 8, 2009, which is incorporated herein by reference and to which priority is claimed pursuant to 35 USC 119.

BACKGROUND OF THE INVENTION

1. Field of the Invention

The invention relates to the field of magnetically guided medical devices, specifically a medical device deployed to move freely within the lumens, cavities and chambers of the human body according the computer aided control of a physician.

2. Description of the Prior Art

Ingestible diagnostic, delivery and therapeutic devices, such as the 'GI capsules', which travel through the cavities and ducts of the gastrointestinal tract, has been in use for over a decade. When a patient swallows just such a device which commonly takes the shape of a pill or capsule, the natural muscular (peristaltic) wave of the digestive tract propels it through the intestinal lumen. While the capsule is moving through the GI tract, a small camera disposed within the capsule enables the physician to inspect the walls of the intestinal ducts for possible detection of tumors, ulcers, and/or bleeding. However, the speed, position, and the direction of the capsule and by therefore by extension the small camera contained within it, are uncontrolled. Currently, obtaining and maintaining a desired observational point or viewing direction is impractical and most of the intestinal walls remain uninspected during a single pass, requiring additional capsules to be swallowed which increase the expense and time used to complete the procedure. Additionally, delivering drugs to a specific locale within the GI tract using a swallowed robotic capsule is imprecise and mostly unattainable.

Other methods for examining and delivering therapeutic drugs to the GI tract include manually operated devices common to endoscopy and colonoscopy. These methods have limited success in reaching clinically important anatomic sites and are generally not comfortable to the patient's experience. Additionally, therapeutic drug delivery to organs such as the brain, the heart, the kidneys, and other critical areas has similar difficulties in accessibility for the purposes of diagnosis and therapeutic treatment.

With the rapid increase of cases such as stomach ulcers and colon cancers, effective and painless methods of regular preventive and anticipatory examinations are desired. Specifically, what is needed is an apparatus and method that allows a small magnetic capsule that is orally ingested to be carefully controlled and guided as it traverses the GI tract of a patient with a minimum level of patient discomfort. The apparatus should also include means for examining specific portions the patient's GI tract as well as delivering a therapeutic or medicating agent to that specific portion by remote command of an operating physician.

There is a considerable library of prior patents wherein attempts have been made to control the movement of an untethered capsule through the body lumens. The prior art suffers from the fundamental inability of controlling an untethered device while being suspended in a levitating state. The inherent instability of an untethered device is known to those familiar with the art of guiding and controlling a permanent magnet in three dimensional space with six degrees of freedom, a condition described by the formal description of Earnshaw exclusion principle.

The presentation and the disclosed solutions provided by the prior art fail to address the fact that a medical device such as an endoscopic capsule with a specific mass necessitate a magnetic force and force gradient sufficient to lift, levitate, rotate and translate such an object in a suspended state. The prior art provides for literal descriptions of such alleged physical control, but do not disclose any solution that practically enables such control. This failure to enable a solution to the problem renders such prior art embodiments impractical and unusable.

Because of these drawbacks, what is needed is further development of the method and system of the described embodiments in Shachar, "Apparatus And Method For Catheter Guidance Control And Imaging", U.S. Pat. No. 7,769,427, which discloses a magnetically guided tethered catheter to provide a system for magnetic guidance control and imaging using a magnetic field and field gradient to rotate, translate and levitate a medical untethered-capsule.

Recently, magnetic systems have been disclosed wherein magnetic fields produced by one or more electromagnets are used to guide and advance a magnetically-tipped device. The electromagnets in such systems produce large magnetic fields that are potentially dangerous to medical personnel and that can be disruptive to other equipment. A novel solution to the limitations noted by the art was developed by the introduction of a magnetic guidance system titled "Catheter Guidance Control and Imaging apparatus (CGCI)", by Magnetecs corp. of Inglewood California. The properties and embodiments of the "CGCI" apparatus and methods are detailed by the following patents and applications: U.S. Pat. No. 7,769,427, Apparatus and Method for Catheter Guidance Control and Imaging; 2006/0116634, System and Method for Controlling Movement of a Surgical Tool; 2006/0114088, Apparatus and Method for Generating a Magnetic Field; 2006/0116633, System and Method for a Magnetic Catheter Tip; U.S. Pat. No. 7,280,863, System and Method for Radar-Assisted Catheter Guidance and Control; 2008/0027313, System and Method for Radar-Assisted Catheter Guidance and Control; 2007/0016006, Apparatus and Method for Shaped Magnetic Field Control for Catheter, Guidance, Control, and Imaging; 2007/0197891, Apparatus for Magnetically Deployable Catheter with Mosfet Sensor and Method for Mapping and Ablation; 2009/0248014, Apparatus for Magnetically Deployable Catheter with Mosfet Sensor and Method for Mapping and Ablation; 2008/0249395, Method And Apparatus for Controlling Catheter Positioning and Orientation; Ser. No. 12/103,518, Magnetic Linear Actuator for Deployable Catheter Tools; 2009/0253985, Apparatus and Method for Lorentz-Active Sheath Display and Control of Surgical Tools; 2009/0275828, Method and Apparatus for Creating a High Resolution Map of the Electrical and Mechanical Properties of the Heart; 2010/0130854, System and Method for a Catheter Impedance Seeking Device; Ser. No. 12/475,370, Method and Apparatus for Magnetic Waveguide Forming a Shaped Field Employing a Magnetic Aperture for Guiding and Controlling a Medical Device; Ser. No. 12/582,588, Method for Acquiring High Density Mapping Data With a Catheter Guidance System; Ser. No. 12/582,621, Method for Simulating a Catheter Guidance System for Control, Development and Training Applications; Ser. No. 12/615,176, Method for Targeting Catheter Electrodes; Ser. No. 12/707,085, System and Method for Using Tissue Contact Information in the Automated Mapping of Coronary Chambers Employing Magnetically Shaped Fields; PCT/US2009/

064439, System and Method for a Catheter Impedance Seeking Device; PCT/US2010/036149, Method and Apparatus for Magnetic Waveguide Forming a Shaped Field Employing a Magnetic Aperture for Guiding and Controlling a Medical Device; PCT/US2010/052696, Method for Acquiring High Density Mapping Data With a Catheter Guidance System; and PCT/US2010/052684, Method for Simulating a Catheter Guidance System for Control, Development and Training Applications. Each of the above listed patents and applications for patent are incorporated in their entirety by reference herein.

Nevertheless, there is a great and still unsatisfied need for an apparatus and method for guiding, steering, and advancing invasive devices and for accurately controlling their positions for providing positioning of magnetic fields and field gradient, for providing a fields configured to push/pull, bend/rotate, and by further enabling apparatus to align the capsule to achieve controlled movement in three dimensional space.

DEFINITIONS

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention. The definitions are provided as exemplars for the sake of clarity and explanation and are not intended to restrict the construction or limit the scope of the claims as may be proper in view of the law and the prosecution history of the application.

Actual Position (AP)—The six degree of freedom position and orientation of the capsule. The capsule position is measured at the center of the distal end.

Automatic Guidance—Methods of automatically advancing, steering and pushing a capsule toward a desired position.

Automatic Magnetic Mode—The control mode that enables the physician to automatically guide the capsule to a target with a simple point-and-click of the mouse button.

Biot-Savart law—is an equation in electromagnetism that describes the magnetic field B generated by an electric current. The vector field B depends on the magnitude, direction, length, and proximity of the electric current, and also on a fundamental constant called the magnetic constant.

capsule—A minimally invasive medical tool used for diagnostic and therapeutic medical procedures. The capsule may have a wide variety of shapes, sizes and capabilities, but all are a combination of a functional end.

Desired Position (DP)—The desired or target six degree of freedom position and orientation of the capsule, or the three degree of freedom desired location for a capsule with an implied optimized orientation which is based on the orientation of the target. Three degree of freedom desired positions are typically used, and the capsule guidance system adjusts the orientation of the capsule for maintaining optimal orientation with a moving surface.

Determining capsule Axis by Intersection of Magnetic Sensor Planes—A method for detecting the orientation of a magnetic pellet in free space using at least two three dimensional magnetic sensors Distal—At the most distant end, or the end of the capsule furthest within the patient.

Earnshaw's theorem—states that a collection of point charges cannot be maintained in a stable stationary equilibrium configuration solely by the electrostatic interaction of the charges. This was first proven by Samuel Earnshaw in 1842. It is usually referenced to magnetic fields, but originally applied to electrostatic fields. It applies to the classical inverse-square law forces (electric and gravitational) and also to the magnetic forces of permanent magnets and paramagnetic materials.

Electromagnetic induction—the production of voltage across a conductor situated in a changing magnetic field or a conductor moving through a stationary magnetic field.

Electromagnetic Refraction and Snell Law—as used, refers to a system of forming an anisotropic wave front due to the use of Snell's observation that the tangential components of two intersecting materials with order of magnitude permeability ($\mu$) difference, will generate a (B) field which is discontinuous regardless of any current density at the interface. This discontinuity is related to the permeability of the two mediums and is defined by the phenomena of ferromagnetic reflection.

Fiducial Alignment—The use of a fiduciary sensor on the patient that monitors the patient's position and orientation with respect to the Magnetically Guided Capsule Endoscope (MGCE), and the use of that sensor data to synchronize the patient's local geometric coordinate system.

Geometric Location—A specific Cartesian point on the geometric map which represents the average position of the tissue location that passes through that point.

Geometric Manifold—A hollow geometric shell that represents the inner surface of a body lumen or cavity.

Geometric Normal Vectors for Tissue Contact Direction—The chamber geometry is analyzed to provide the perpendicular directions at each part of the surface which are considered the directions of optimal tissue contact.

Hall Effect Position Sensors—noncontact devices that convert energy from a magnetic field into an electrical signal. They use the Hall Effect, a voltage caused by current-flow in the presence of a magnetic field. Hall Effect position sensors function via an electrical potential (the Hall voltage) that is developed between the two edges of a current-carrying conductor whose faces are perpendicular to an applied current flow. The presence of a magnetic field is also required, as the Hall element is the most basic magnetic field sensor.

Insert Ring—as used refers to a ferrous material with permeability of one order magnitude lower than the pole face.

Lens—as used refers to an apparatus used in a MGCE system which generates a DC magnetic field, with magnetic geometry on demand by the use of combination of different material permeabilities. The "lens" comprises a ferromagnetic core having an anisotropy axis permanently magnetized in a direction perpendicular to the insert ring, the insert ring being disposed in the magnetic field such that the anisotropy axis is opposite the magnetization direction of the DC magnetic field, the pole face encircled by the ring having cut-outs shaped and dimensioned to create a localized minimum of the magnitude of the magnetic field vector of the combined magnetic field in a focus volume away from the aperture.

Local Coordinates and Global Coordinates, Transformation Matrices—The local coordinate system is a Cartesian coordinate set that is fixed with respect to the patient's frame. Using the fiducial alignment data, transformation matrices are created and used to convert positions and orientations between the patient's local coordinate system and the MGCE-referenced global coordinate system.

Magnetic Aperture—as used refers to the optical behavior of ferrous materials having negative permeability at or near permeability resonance which can yield large field amplifications and can refract the flux lines through negative angles. This enhancement is guided analytically by the Biot-Savart law and the inclusion of mirror image currents.

Magnetic flux—represented by the Greek letter φ (phi), is a measure of quantity of magnetism, taking into account the strength and the extent of a magnetic field.

Maxwell's equations—are a set of four partial differential equations that relate the electric and magnetic fields to their sources, charge density and current density.

Motion Algorithm—An additional motion that is injected into the standard position control system to provide a useful agitation to the capsule position as to collect data over a greater spatial volume.

Motion Compensation Filter—Motion compensation filters use a fiducial reference to subtract the movement of that reference position and orientation from that of the tool coordinate position. This allows the regulator to ignore the unwanted motion as it guides the capsule from the actual position to desired position.

Multi-Position Solenoid Bobbin—A standard solenoid is a two-position magnetic actuator that uses a magnetic coil to move a permanent magnet back-and-forth. The disclosure further expands on the standard solenoid to allow multiple positions and finer control when used to actuate surgical tools.

Nanocrystalline magnet—are used as an embedded pallet within the MGCE Tool Set, such as magnetically deployable tools, which further provides for large coactivity and dramatic improvement in energy density.

Obstacle Detection and Avoidance—An algorithm for seeking out a target when it detects contact with an obstacle outside of the targeting manifold and directs the navigation artificial intelligence (AI) to select a different path to Desired Position (DP).

Path Planning—The analysis of the acquired mapping geometry of the GI track to optimize the path to Desired Position (DP).

Path to Tissue Contact, Target Manifold—The Navigation AI selects a path to Desired Position (DP), region of expected target, and allowable error which become the targeting manifold. Contact outside of the targeting manifold is considered to be with an obstacle.

Pole face—as used refers to an aperture comprising of ferrous material formed with a specific geometry and a high permeability ($\mu > 1000$) value.

Predictive Kinematic Algorithm, Kinematic Rest Position—A mathematical simulation of the capsule position and orientation in free space under each magnetic field setting and capsule length.

Predictive Motion Control Cursor—The use of a predictive algorithm to produce a realistic capsule cursor that simulates the movement and final location of a capsule before the physician commands the actual cursor there.

Proximal—Closer to the point of attachment or observation. The side of the device that is the opposite of the distal end.

Relative Contraction Displacement and Velocity—The local contraction of the tissue as measured with respect to the tissue itself.

Respiration Compensation—The patient's respiration is an additional factor body motion. Low frequency filters can use the fiducial alignment sensor data to extract the motion due to respiration and use anatomical data to compensate for it.

Runge-Kutta Ordinary Differential Equation Based Physics Engine—In the absence of position detection electrodes along the entire capsule length, the MGCE uses a mathematical simulation engine used to produce a realistic line representing the capsule relative to its GI track. The line gives a realistic view of the amount of line in the GI track that the capsule traveled and how it probably lies along the anatomical surface.

Savitzky-Golay smoothing filter—a type of filter, which essentially performs a local polynomial regression on a series of values to determine the smoothed value for each point. Methods are also provided for calculating the first up to the fifth derivatives.

Scaling Factors—are the technique of scale modeling as it applies to magnetic field problems. Simple relations for modeling static and dynamic linear devices are presented first. Particular attention is then given to the problem of scale modeling of nonlinear ferromagnetic devices. While static nonlinear fields can usually be modeled with good accuracy, time-varying fields in nonlinear ferromagnetic materials have severe modeling limitations.

Shaped Magnetic Field—as used, refers to a system of forming shape magnetic field geometry (Lobe), which operates under the principles defined by the invention.

Six Degrees of Freedom—A coordinate set that describes both the position of an object and its orientation in space.

Tactile Feedback, Haptic Joystick controller—To expand the physician's sensory input, tactile 'Haptic' feedback may be used in the controller so the physician can feel the surfaces, motion and obstacles within the workspace.

Tissue Contact—Where the distal end of the capsule maintains continuous contact with the surface of the GI wall throughout the peristaltic cycle.

Tissue Displacement Map, Global Displacement—The movement of the tissue with respect to an external reference.

virtual capsule or (VC)—as used refers to a physical assembly, similar to a joystick, which is manipulated by the surgeon/operator and delivers tactile feedback to the surgeon in the appropriate axis or axes if the actual capsule encounters an obstacle.

Magnetically Guided Capsule Endoscopy (MGCE)—as used refers to a system for guiding and controlling a medical device within a body of a patient comprising a set of electromagnets formed with a specific geometry and act as a magnetic cavity to deliver electromagnetic radiation acting on a permanent magnet further delivering energy in a manner to push, pull, and rotate a surgical tool(s) fitted with such. The chamber is a highly compact magnetic aperture assembly which economically provides the highest field strength on the axis with the minimum DC field and minimum outer field strength of the coil winding. The assembly is fitted with a parabolic shielding antenna and eight electromagnets coaxially aligned with the lens axis, the chamber means each having a first end and a second end, the first ends being spaced from each other to define a unshielded lens gap there between, the lens gap having a coil means positioned about the chamber to create a magnetic field, a cooling agent adapted to be present about the chamber which cause a concentration of the magnetic field adjacent to a permanent magnet tool, and a ferromagnetic ring-shaped pole face on each of the first ends of the coil for regulating and guiding the magnetic field. The definition is further expanded in the patent to include a method for magnetically detecting the capsule position and relating that global capsule position to the patient's local coordinate system.

BRIEF SUMMARY OF THE INVENTION

The disclosed application of newly configured magnetic cavity or magnetic chamber enables the control of the magnetic field, namely control of shaped field characteristics, and by further using a magnetic-aperture as described below. The disclosed embodiments will improve the art of robotic guidance of an untethered capsule within a patient's GI tract.

These and other problems are solved by a the disclosed MGCE system which employ a magnetic chamber for guidance and control of system that uses a magnetic aperture and electromagnets to configure a magnetic shaped field for guiding an untethered device, such as a capsule endoscope or other medical device through a patient's body cavities. This is achieved by the use of varying the electromagnetic wave and its respective flux density axis. This is accomplished by a method for forming a shaped magnetic field and is augmented by the use of a regulator which enables a nonperiodic or what is hereafter denoted as a static (DC) or quasi-static (quasi-DC) field generator and a pulse-burst field regulator. Static (DC) or quasi-static (quasi-DC) may also be referenced in this specification as simply DC.

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification.

Thus it can be understood that the illustrated embodiment of this invention present a medical capsule navigation system comprised of a magnetically equipped untethered propulsion capsule and at least two external multicoil electromagnetic magnetic field generators, one for generating field gradients and one for generating pulse-bursts of repulsive fields, which together offer a method and procedure overcoming the dynamic instability issues associated with magnetically maneuvered and levitated intra-lumen medical devices. The presented magnetic and navigation method enables rapid diagnoses and treatments of specific anatomical locations within the lumens and cavities of the human body.

The capsule is magnetically equipped comprising advantageously shaped magnetic and electrically conductive rings, disks, and plates placed internal to the capsule exhibiting anisotropic electromagnetic properties typical to permanent magnets and silver-coated, or other high conductivity materials respectively. In response to externally generated and regulated static (DC) or quasi-static (quasi-DC) magnetic and pulsed electromagnetic fields the capsule will levitate, move, and orient in a controlled manner.

Holding the capsule in place is achieved by controlling the external magnetic fields such that the gradient forces generated by the static (DC) or quasi-static (quasi-DC) magnetic fields balance with the peristaltic forces and gravitational pull exerted on the capsule while the dynamic repulsive forces generated by the pulsed electromagnetic fields rapidly counter any movements and rotations away from the desired position and orientation. The dynamic, naturally repulsive magnetic forces generated by the induced currents in the conductive rings and plates during the short pulse-bursts of the periodic field generator are sufficient to stabilize the position and orientation of the capsule against the Earnshaw instability. The instability is due to the rapid increase of forces the capsule's permanent magnets would experience if the above the force balance is disturbed by whatever causes. The capsule carrying the capsule would accelerate toward the strongest proximate magnets of the external static (DC) or quasi-static (quasi-DC) field generator, or the capsule would spin around its long axis.

Moving and orienting the capsule along the long axis of the capsule is accomplished by utilizing at least one permanent magnet magnetized in the capsule's axial direction. The static (DC) or quasi-static (quasi-DC) field gradients provide the propulsion forces in accord with equation:

$$F = M \cdot \frac{dB}{dz} \cdot A \cdot L_Z$$

where M is the permanent magnet magnetization including its vector direction, A is the cross section of the permanent magnet and $L_z$ is the length of the permanent magnet along with the capsule's long-axis z direction. The derivative $$\frac{dB}{dz}$$

is the gradient slope of the magnetic field generated by the static (DC) or quasi-static (quasi-DC) external field generator and it can take either plus or minus signs. The field gradients are controlled with six degrees of freedom by the gradient regulator to set the direction and magnitude of the highest slope. The capsule rotates into the direction of the maximum gradient with opposite magnetic poles of the capsule and the field generator aligning. The capsule is then propelled along that gradient path by the force calculated by above equation. During this maneuver the periodic pulse-bursts generate repulsive forces in the at least one conductive ring or plate of the capsule to damp the speed of the movement and keep the dynamic control stability of the moving capsule. The repulsive forces are controlled with six degrees of freedom by the pulse burst regulator.

Rotating the capsule around the long, cylindrical axis z is accomplished by having a y axis, perpendicularly magnetized at least one permanent magnet ring in addition to the axially magnetized at least one permanent magnet in the capsule. The radially magnetized ring responds to the circular rotation of the static (DC) or quasi-static (quasi-DC) magnetic field by rotating the capsule with this field. This rotation enables the operator to place a medical device carried in the capsule into an advantageous position in relation to the tissue or cavity.

In another embodiment of the magnetically guided capsule the permanent magnet rings in the capsule are arranged to have at least one permanent magnet ring magnetized cylindrically around the z axis. Such magnetization can be obtained by magnetizing segments of a cylindrically shaped magnetic material, and then assemble the segments into a full cylinder after magnetization. The magnetization creates a single permanent magnet which has one pole around the cylinder's long outer surface, and has two opposite poles returning the flux at the ends of the cylinder. The cylindrical magnetization enables controlled capsule movement toward a magnetic null at the center of the gradient field generator. In this embodiment the pulse-bursts of the repulsive field generator keeps the control stability by preventing the capsule spin into a force-neutral position before it reaches the magnetic null. To accomplish the control stability the induced currents in at least one of the conductor ring producing repelling forces will be activated and regulated with six degrees of freedom by the pulse-burst regulator. Rotation of the capsule is accomplished by unevenly magnetizing the individual cylinder segments before assembly. The unevenly magnetized permanent magnet responds to the circular rotation of the static (DC) or quasi-static (quasi-DC) magnetic field by rotating the capsule with this field. This rotation enables the operator to place a medical device carried in the capsule into an advantageous position in relation to the tissue or cavity.

In another embodiment of the magnetically guided capsule the magnetic elements in the capsule are the combination of the z axis and the cylindrically magnetized permanent magnet rings assembled together with the pulse burst induced current conductive rings. The z axis permanent magnets will exhibit the Earnshaw instability effect, but the cylindrically magnetized permanent magnet reduces the instability by pulling and holding the capsule close to the magnetic gradient null. However, the available forces generated by the static (DC) or quasi-static (quasi-DC) fields will be much higher than the single permanent magnet embodiment. In this embodiment the pulse-bursts of the repulsive field generator also keeps the control stability by preventing the capsule spin into a force-neutral position before it reaches the magnetic null preventing the capsule to yield the accelerating forces due to the Earnshaw effect. To accomplish the control stabilization the induced currents in at least one of the conductor ring producing repelling forces will be regulated with six degrees of freedom by the pulse-burst regulator. Rotation of the capsule is also accomplished by unevenly magnetizing the cylinder segments. The unevenly magnetized permanent magnet cylinder responds to the circular rotation of the static (DC) or quasi-static (quasi-DC) magnetic field by rotating the capsule with this field. This rotation enables the operator to place a medical device carried in the capsule into an advantageous position in relation to the tissue or cavity.

The pulse burst field generator provides the induced currents in the at least one conductive ring and plate of the capsule. Induced by the directed and regulated pulse bursts of the multicoil periodic magnetic field generator, the plates have circulating currents in them generating a magnetic field which, in accord with Lenz-law, oppose the fields which induce them. Thereby, there are opposing magnetic forces as well between the plates and the pulse-burst field generator. Thus, the plates being perpendicular to the z axis have forces along the z axis moving the capsule forward or reverse, or holding the capsule in place against the external peristaltic forces and gravitational pull.

The pulse burst generator also induces circulating currents in the electrically conductive ring. The rings have circulating currents on the ring surfaces penetrating into the conductive material to the Skin-effect depth. The circulating currents on the ring surfaces generate magnetic fields according to the Lenz-law opposing the fields which induce them. The opposing magnetic forces are between the at least one conductive ring and the pulse-burst field generator. The conductive ring has forces along the y and x axis of the capsule moving the capsule up or down and sideways.

The conductive ring has a cut or slit such that the ring cannot carry short circuit currents around the ring as a shorted turn. The slit of the ring advantageously provides division of the surfaces limiting current circulation to the sides in the direction facing the pulse burst generator coils. The slit also enables capsule rotational repulsive force control stabilizing the rotational forces from the static (DC) or quasi-static (quasi-DC) field generator.

The directionally controlled pulse-burst fields during guidance control induce currents in both at least one ring and in the at least one plate. The current loops are naturally distributed on the ring and plate surfaces in accord with the laws of induction and field generation resulting magnetic forces in all three directions of the capsule's x, y and z axis in reference to the pulse burst field generator coordinate system. The pulse-burst regulator activates and controls the multicoil field generator to obtain the desired magnitude and direction of stabilizing and controlling forces from the conducting rings and plates. The pulse bursts control results rapid, millisecond type corrections and can respond to the dynamic force requirements of stability and environmental disturbances, such as peristaltic forces. The main guidance control loop with its large coils assemblies cannot respond fast enough for such stability corrections. However, the main loop can ketch-up with the field requirements by changing the coil currents of the static (DC) or quasi-static (quasi-DC) field generator and thereby reducing the substitution of stabilizing forces obtained from the pulsed bursts generated in the coils of the pulse-burst regulator loop.

Two multicoil external magnetic field generators surround the capsule guidance region. One generator, comprised of eight independently controlled electromagnetic coils, generates a slow changing three-dimensional magnetic field-gradient lobe with the function of producing magnetic force gradients between the capsule's permanent magnets and the external magnetic field structure for capsule propulsion. The second magnetic field generator, also comprised of eight independently controlled coils installed on the same magnetic core structure, has the function of generating the magnetic pulse-busts to produce controlled repulsive forces for damping and reducing the Earnshaw instability effect and to contribute to the levitational and propulsion forces generated by the static (DC) or quasi-static (quasi-DC) field generator.

To obtain the desired capsule location and orientation the gradient lobe and the electromagnetic bursts are regulated by two closed loops. The outer loop is regulating the static (DC) or quasi-static (quasi-DC) field generator, and the inner loop is regulating the pulse-burst. The loops obtain their location and direction and dynamic feedbacks from magnetic and inertial sensors located in the capsule. The loops obtain the desired levitation and orientation commands from the operator Joystick or from a intra-lumen map containing the destination points the capsule need to be guided to. In case of diagnostic procedures visual and acoustic location-orientation sensing system can also be deployed.

The magnetic and electric rings, disks and/or plates of the capsule are preferably comprised of anisotropic ferrous and conductive materials such as high magnetization NdFeB compositions and silver or ultra-conductor conductive materials respectively. The material selection is not limited to the presently available magnetic and conductive materials whether anisotropic or isotropic. Similar materials exhibiting the magnetic and conductive properties exploited in the embodiments devised in the macroscopic or nano-structured meta-materials may also be used without departing from the original spirit and scope of the invention.

In one embodiment, a magnetic circuit is configured to generate a desired magnetic field in the region of a multicoil cluster of electromagnets.

In one embodiment, one or more poles of the cluster are modified to provide an anisotropic radiation with respect to other poles in the cluster, and to allow shaping of the magnetic field.

In one embodiment, one or more magnet poles can be modified and the pole face geometry altered, to shape the magnetic field.

In one embodiment, the MGCE system (magnetic cavity), with its cluster of electromagnets can be positioned to generate magnetic fields that exert a desired torque on the capsule, but without a translational force being applied to the capsule (e.g., the capsule will pivot without translation). This results in a rotational movement of the capsule's head toward a selected direction. The MGCE system accomplishes this by the use of the shape magnetic field.

In one embodiment, the multicoil cluster is configured to generate a relatively high gradient field region for exerting a translational force on the capsule (e.g., a push-pull movement), with little or no torque on the center axis relative to the field direction.

In one embodiment, the MGCE and its magnetic cavity forming the magnetic chamber includes a closed-loop servo feedback system.

In another embodiment of the MGCE magnetic chamber is configured as a magnetic field source (the generator) to create a magnetic field of sufficient strength and orientation to move a magnetically responsive surgical tool(s) such as a capsule endoscope, to enable the manipulation of the tool in a desired direction by a desired amount.

In one embodiment, the MGCE's detection system is configured as disclosed in Shachar, U.S. Pat. No. 7,280,863 by employing radar and other imaging modalities to identify the location and orientation of surgical tool(s) within a patient's body. The radar employs the principle of dielectric properties discrimination between biological tissue via its dielectric constant verses the dielectric properties of polymers, metals or other synthetic materials forming the medical tool, while further establishing the spatial as well as time domain differentiating signal due to conductivity and attenuation in mixed media. Position detection using impedance technique, a Hall Effect sensor, an inertial platform using an accelerometer or other means of magnetic positioning are detailed by Shachar et al. patents noted above.

Further embodiments of the scale rules guiding the construction of a scaled model include the tailoring of constants relating to the geometrical orientation of the pole faces to modify the anisotropic radiation of the electromagnetic generators and provide for optimization of flux density axis location relative to the location of the tool magnetic tip.

In one embodiment, the magnetic cavity multicoil cluster is configured to generate a magnetic field gradient for exerting an orthogonal force on the capsule (a sideways movement), with little or no rotating torque.

In one embodiment, the magnetic cavity multicoil cluster is configured to generate a mixed magnetic field to push/pull and/or turn/rotate the capsule.

In one embodiment, the magnetic cavity multicoil cluster is configured to move the location of the magnetic field in three dimensional space relative to a desired area. This magnetic shape control function provides efficient field shaping to produce desired magnetic fields.

One embodiment employs the magnetic cavity with its shaped magnetic regulator to position the tool (capsule) inside a patient's body, further maintaining the capsule's head in the correct position.

In one embodiment, the physical capsule includes a permanent magnet that responds to the magnetic field generated externally by the magnetic cavity. The external magnetic field pulls, pushes, turns, and holds the capsule in the desired position. One of ordinary skill in the art will recognize that the permanent magnet can be replaced or augmented by an electromagnet.

One embodiment includes the magnetic cavity and its regulating apparatus that is intuitive and simple to use, that displays the capsule's location in three dimensions, that applies force at the capsule to pull, push, turn, or hold the capsule as desired, and that is configured to producing a vibratory or pulsating motion of the capsule with adjustable frequency and amplitude to aid in advancing the capsule through obstructions. One embodiment provides tactile feedback at the operator control to indicate an obstruction encountered by capsule.

One embodiment of the magnetic cavity and its regulator to include a user input device called a "virtual capsule" (VC). The virtual capsule includes a physical assembly, similar to a joystick, which is manipulated by the surgeon/operator, which delivers tactile feedback to the surgeon in the appropriate axis or axes if the actual tip encounters an obstacle, and which allows the surgeon to guide actual surgical tool such as capsule through the patient's body.

In one embodiment, the magnetic cavity symmetry (eight coil clusters), enables a regulator to compute the desired field(s) under the doctrine of linear transformation of all matrices in the magnetic chamber to enable closure of all vector field operations (addition, subtraction, superposition etc.) without the need for tailoring the magnetic cavity-regulator linearity. Hence symmetry is preserved within the MGCE's magnetic chamber.

In one embodiment, the capsule includes a permanent magnet and or multiple articulated permanent magnets to enable manipulation of capsule or a surgical tool by the use of the magnetic cavity to generate mixed magnetic fields. The use of multiple permanent magnetic elements with different coercivity ($H_{cJ}$) values, will result in a "primary bending mode" and a "secondary bending mode" on the same axis (relative to the electromagnetic field axis), while using for example, sintered Nd—Fe—B with different values, e.g. N45, N50 and N52.

In one embodiment, the magnetic cavity electromagnetic circuit includes a circular-arm geometry using a ferromagnetic substance, such as parabolic antenna, (e.g., a ferrous, substance, nickel substance, etc.) further increasing the efficiency of the magnetic cavity as the electromagnetic field's energy is attenuated by the parabolic shielding antenna which forms an integral flux carrier and a containment of stray fields.

In one embodiment, the magnetic cavity regulator uses numerical transformations to compute the currents to be provided to various electromagnets to direct the field by further positioning one or more of the electromagnets to control the magnetic field used to push/pull and rotate and levitate the capsule in an efficient manner within the chamber.

In one embodiment, the magnetic cavity regulator includes a mechanism to allow the electromagnet poles faces to form a shaped magnetic based on a position and orientation of the capsule's travel between the AP to DP. This method further optimizes the necessary power requirements needed to push, pull, and rotate the surgical capsule. By employing "lensing" modes of the field with the use of magnetic aperture, the magnetic cavity is forming a shaped magnetic field relative to the minimal path between AP to DP.

In one embodiment, the MGCE system is fitted with sensory apparatus for real time detection of position and orientation to provide a command inputs to a servo system that controls the capsule location from AP to DP. The desired position, further generates a command which results in shaping the magnetic field geometry based on magneto-optical principles as shall be clear when reviewing the figures and the accompanying descriptions.

In one embodiment, the MGCE's servo system has a correction input that compensates for the dynamic position of a body part (peristaltic), thereby offsetting the response such that the capsule moves substantially in unison with the dynamic position (e.g., with the peristaltic motion).Further, synchronization of dynamic position of the capsule with the appropriate magnetic field force and direction is accomplished by the response of the MGCE's regulator and its resulting field's intensity and field's geometry.

In one embodiment of the magnetic cavity magnetic chamber, its regulator and a magnetically fitted capsule, form a system whereby: i) the operator adjusts the physical position of the virtual capsule (VC); ii) encodes a change in the virtual capsule position along with data from a position detection system; iii) generates servo system commands in the regulator that are sent to a servo system control circuitry; iv) operates the servo mechanisms using the servo system control apparatus to adjust the condition of one or more electromagnets from the cluster to vary the power relative to distance and/or angle of the electromagnet clusters vis-a-vis the capsule's permanent magnet position, further energizing the electromagnets to control the magnetic element (capsule) within the patient's body; v) sensing the new position of actual capsule by the position detection system, thereby allowing for example a synchronization of the capsule position on an image produced by a camera; vi) provides feedback to the servo system control apparatus and to the operator interface; and vii) updates the displayed image of the capsule position in relation to the patient's internal body structures.

In one embodiment, the operator can make further adjustments to the virtual catheter capsule (VC), position and the sequence of steps ii through vii above are repeated. In one embodiment, the feedback from the servo system and control apparatus (the regulator), deploys command logic (AI routine) when the actual capsule encounters an obstacle or resistance in its path. The command logic is further used to control stepper motors which are physically coupled to the virtual capsule. The stepper motors are engaged to create resistance in appropriate directions that can be felt by the operator, and tactile feedback is thus provided to the user.

In one embodiment, the coil current polarity and polarity rotation are configured to allow the coil cluster to generate torque on the capsule.

In one embodiment, the coil current polarity and rotation are configured to provide an axial and/or orthogonal force on the capsule.

In one embodiment, the magnetic cavity-eight coil (DC) symmetry enables an apparatus that generate the desired magnetic field in an optimized pattern.

In one embodiment, the magnetic cavity with its coil cluster is fitted with a parabolic shield (the magnetic shield antenna), which collects the magnetic flux from the effective space and creates a return path to decrease the need to shield the stray magnetic radiation emanating from the magnetic cavity's footprint.

In one embodiment a ferro-refraction technique for field magnification is obtained when a current segment is near a high magnetic permeable boundary. It is further shown that ferro-refraction may enhance the design and performance of magnets used for NMR or MRI by increasing the efficiency of these magnets. Ferro-refraction refers to the field magnification that may be obtained when a current segment is near a high magnetic permeability ($\mu$) boundary. Refraction occurs at any boundary surface between two materials of different permeability. At the surface, the normal components of the magnetic induction (B) are equal and the tangential components of the magnetic field (H) are equal.

In furthering the embodiment noted above, a ferro-refraction technique, and the novel architecture of the disclosed magnetic cavity. This invention enhance the magnetic cavity magnification of the field, by using the magnetic aperture pole face material permeability and its anisotropic behavior to form a suitable lens for establishing an efficient geometry and flux density for guiding and controlling the movement of the capsule from AP to DP. This enhancement is guided analytically by the Biot-Savart law and the inclusion of mirror image currents. (See: An Open Magnet Utilizing Ferro-Refraction Current Magnification, by, Yuly Pulyer and Mirko I. Hrovat, Journal of Magnetic Resonance 154, 298-302 (2002)).

Improving the energy efficiency of the MGCE system for the purpose of guiding, and controlling the capsule (an untethered capsule endoscope), during medical procedure, require that the capsule should be capable of operating under the regimen of three degrees of rotation and three degrees of translation in three dimensional space. These conditions are further supplemented by including the ability of the capsule (capsule endoscope) to be levitated within a body cavity such as the stomach or an open tubular organ such as the colon. The invention relies on the fundamental construct for generating a specific geometry of flux density of the magnetic field, (on demand), relative to a moving permanent magnetic target within the boundary of the disclosed MGCE system.

In the particular applications of using a magnetically guided capsule the MGCE-magnetic cavity principle and its embodiments forming this invention use a novel configuration of a magnetic cavity formed as a bounded, significantly sized electromagnetic chamber, within which controllable energy propagation can take place. In contrast to HF magnetic cavities the chamber of a spherically confined magnetic field generator requires not only directional field-power flow, but this flow needs to be three-dimensional. The formation of shaped magnetic field in guiding and controlling an untethered capsule for diagnostic and therapeutic purpose is one of the embodiments of the disclosed invention, providing for improved energy utilization in translating and rotating the capsule and by further improving the controllability.

Energy in the generated field is accomplished by transferring the electromagnetic radiation through the interaction between the field and the guided capsule, providing the work to move and propel a medical tool(s) such as capsule endoscope from actual position (AP) to desired position (DP) while negotiating such translational as well as rotational forces against: tissue forces, gravitational pull, peristaltic action and the capsule weight.

The magnetic field generator, having multiple core-coils located spherically around the operating area, (the effective space), shapes the chamber magnetic field to establish a three dimensional energy propagation wave front which can be stationary as well movable and shapeable to provide the necessary power flow into the capsule with its magnetic elements, to torque it and or push it in the direction of the power flow.

The field generator has two modes of operation. In one mode it generates a static magnetic field which stores the guidance energy in the operating region in accordance with the following equation:

$$U_{ststic} = \int_0^B H \cdot dB \ [J/cm^3]$$

This energy produces the work of transporting the permanent magnet from AP location to the DP. This work relates to the magnetic field as follows:

$$W = -f \int_a^b H \cdot dl$$

where k is a factor which combines magnetic and physical constants.

The static fields are generated as the result of the superposition of multiple static magnetic fields and are shaped and focused to produce the required field strength and gradient to hold the capsule in a static position and direction. The system satisfies the Maxwell's equations for static magnetic field.

However, once the capsule needs to move or change direction, the system operates in the dynamic mode which involves time varying transient field conditions. In this mode the time varying form of the Maxwell's equations need to be used in assessing the magnetic cavity capabilities for controlling the electromagnetic transient propagation of the EM (electromagnetic) energy in the chamber while using the multicoil magnetic radiator assembly (The magnetic cavity).

These transient dynamic conditions are described by the wave equations:

$$\nabla^2 E = k_2 \left( \frac{\sigma}{\varepsilon} \frac{\delta H}{\delta t} + \frac{\partial^2 H}{\partial t^2} \right)$$

$$\nabla E = 0$$

$$\nabla^2 = M = k_3 \left( \frac{\sigma}{\varepsilon} \frac{dH}{dt} + \frac{\partial^2 H}{\partial t^2} \right)$$

$$\nabla M = 0$$

In forming the preferred embodiments of this invention all field distributions must satisfy these field equations in addition to the Maxwell's formalism. During the dynamic regulations the linear superimposition entails the calculations of longitudinal propagation of waves generated from each source. The longitudinal components are extracted from the wave equation by solving the following differential equation:

$$\frac{\partial^2 H_z}{\partial x^2} + \frac{\partial^2 H_z}{\partial y^2} = -k_4^2 H_z$$

The energy in the dynamic field can then be calculated:

$$U_{dynamic} = \frac{\varepsilon}{2} \int E^2 d\tau + \frac{\mu}{2} \int H^2 d\tau$$

And the power in the propagated wave:

$$P_{wave} = \int (E \times H) \cdot ds$$

The electric field E component at the field regulation speeds required for capsule guidance is relatively small in comparison to the magnetic component. However, the superposition of the complementary electromagnetic fields generated by a pair of spherically symmetric core-coil pairs will generate a field which is essentially behaving as a standing wave, dynamically changing the three-dimensional magnetic landscape at and around the center of the operating region.

The disclosed magnetic cavity as a magnetic field generator with a spherical chamber within the operating region (the effective space) is described. The objective of the magnetic cavity structure is to generate about 0.10 Tesla field strength and about 1.3 Tesla/meter field gradient in this region exerting adequate torque and force on a permanent magnet installed in the capsule. Magnetic focusing technique in the disclosed apparatus is necessary to limit and keep field generator size, weight and power consumption to a minimum.

There are three methods used in the illustrated embodiment of the invention to concentrate the field in the center operating region:
a) Shaped and oriented magnetic pole faces,-magnetic aperture geometry,
b) Anisotropic permeability built into the pole faces, Magnetic aperture material, and
c) Magnetic containment using shield-like magnetic returns integrated into the outer surface of the magnetic field generator,-magnetic cavity parabolic antenna.

The first two methods combined exhibit and define the flux refractory behavior according to the rules governing an optical lens, while observing visible light transmission through different refractory index. Hence, the use of an apparatus and method in forming a magnetic aperture within the confinement of a magnetic cavity, is described to enable magnetic lensing.

In another embodiment the permeability of the magnetic material can be varied electronically, thus a dynamic aperture correction can be devised to produce the needed field parameters in the operating region with reduced field generator power.

In another embodiment the optical behavior of ferrous materials having negative permeability at or near permeability resonance can yield large field amplifications and can refract flux lines through negative angles. The illustrated embodiments of the invention employ all of these magnetic focusing enhancements.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and together with the detailed description of the invention, serve to explain the principles of the present invention.

FIG. 35 is an orthographic cross section of the apparatus forming the magnetic aperture and its EM radiator.

FIG. 36C is an orthographic graphic representation of the magnetic aperture with a hybrid permeability aperture.

FIG. 36D is a view depicting the magnetic aperture with a hybrid permeability values.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

A magnetically guided capsule is driven by a strong electromagnetic repulsion and levitation interaction between an external AC/DC magnetic gradient-lobe generator and a set of uniquely magnetized ferrous-conductive elements within the capsule. The capsule may be used in medical diagnostic examinations, delivery procedures, or other procedural operations requiring a capsule to be navigated through the lumens and cavities of the human body wirelessly and without any physical contact with the magnetically guiding field generator external to the human body. The capsule may be used in a variety of diverse fields common to medical devices including, but not limited to visual mapping, diagnostics, biopsy, and other therapeutic and drug delivery procedures.

The propulsion means within the capsule is equipped with at least two set of conductive-magnetic rings, disks or plates, each possessing anisotropic magnetic properties. A plurality of three-dimensional dynamically variable AC/DC magnetic gradient fields generated externally to the patient provide the gradient forces and rotational torques required to cause the capsule and the host capsule to translate and rotate within the cavities and lumens of the body according to the commands of a computer aided operator. The dynamics of the propulsion capsule are aided and stabilized by an external AC magnetic field system integrated into the DC field-gradient generator which produces eddy-current repulsive forces that are exerted onto the conductive elements within the propulsion capsule's structure. It must be understood throughout the disclosure that a DC magnetic field is meant to include a slowly varying magnetic field, e.g. 5-6 Hz,' and is not limited to a static magnetic field. In general the amplitude of the "DC magnetic field" will also be modulated in time according to the physician's control to move and orient the capsule. The AC magnetic field is generally meant to include a burst or pulsed magnetic field having a Fourier spectrum according to the pulse envelope.

Figure 1:
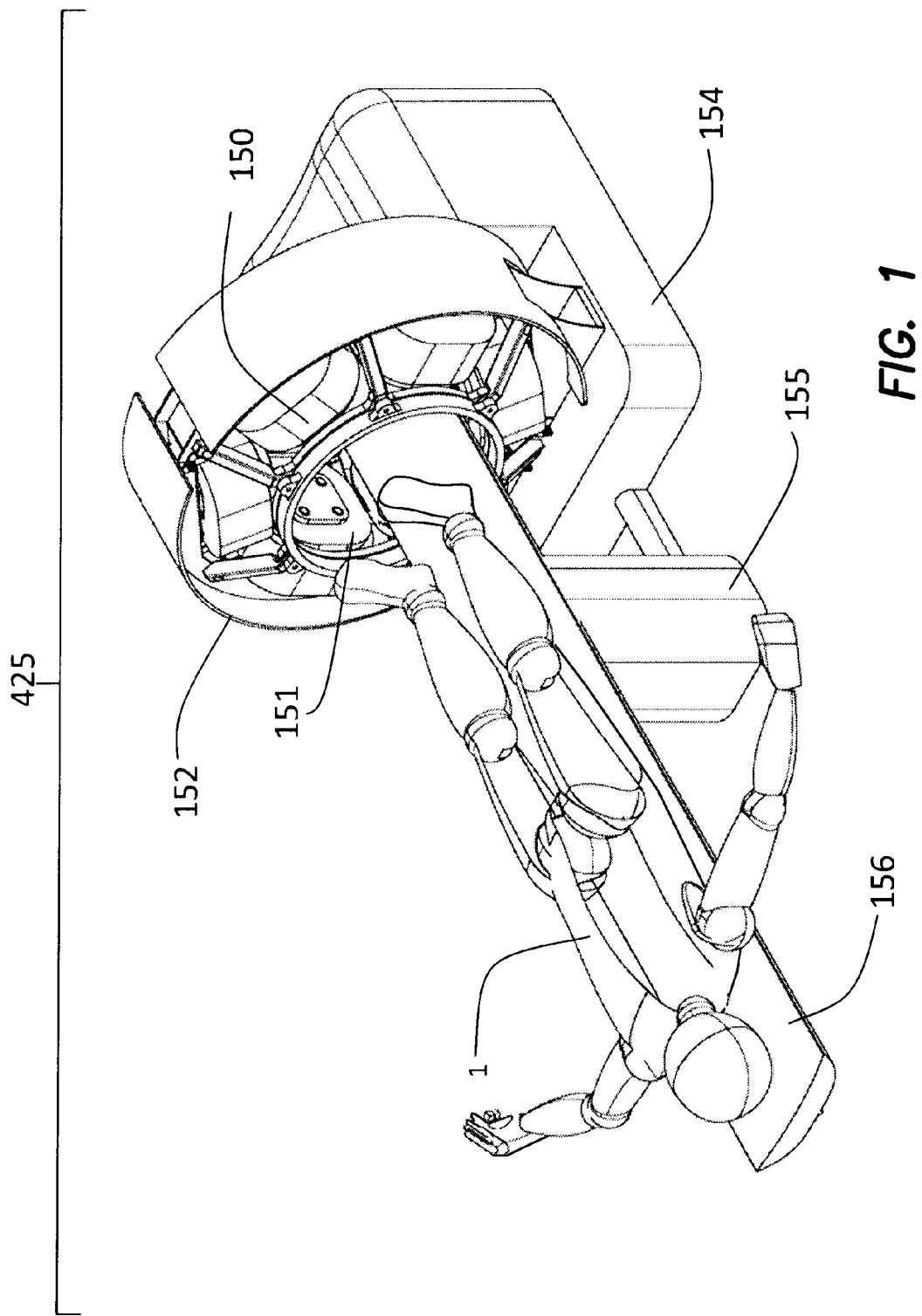
FIG. 1 is a perspective diagram which illustrates the MGCE apparatus showing a patient resting on horizontally movable bed with motorized bed moving assembly surrounded by the magnetic assembly.

FIG. 1 is an isometric illustration of the MGCE apparatus 425 showing patient 1 resting on horizontally movable bed 156 with motorized bed moving assembly 155 surrounded by the magnetic assembly 152. The magnetic assembly 152 includes both DC coils 150 and AC coils 151 on a common laminated core. The magnet power equipment is housed below the magnetic assembly in the base 154.

Figure 1A:
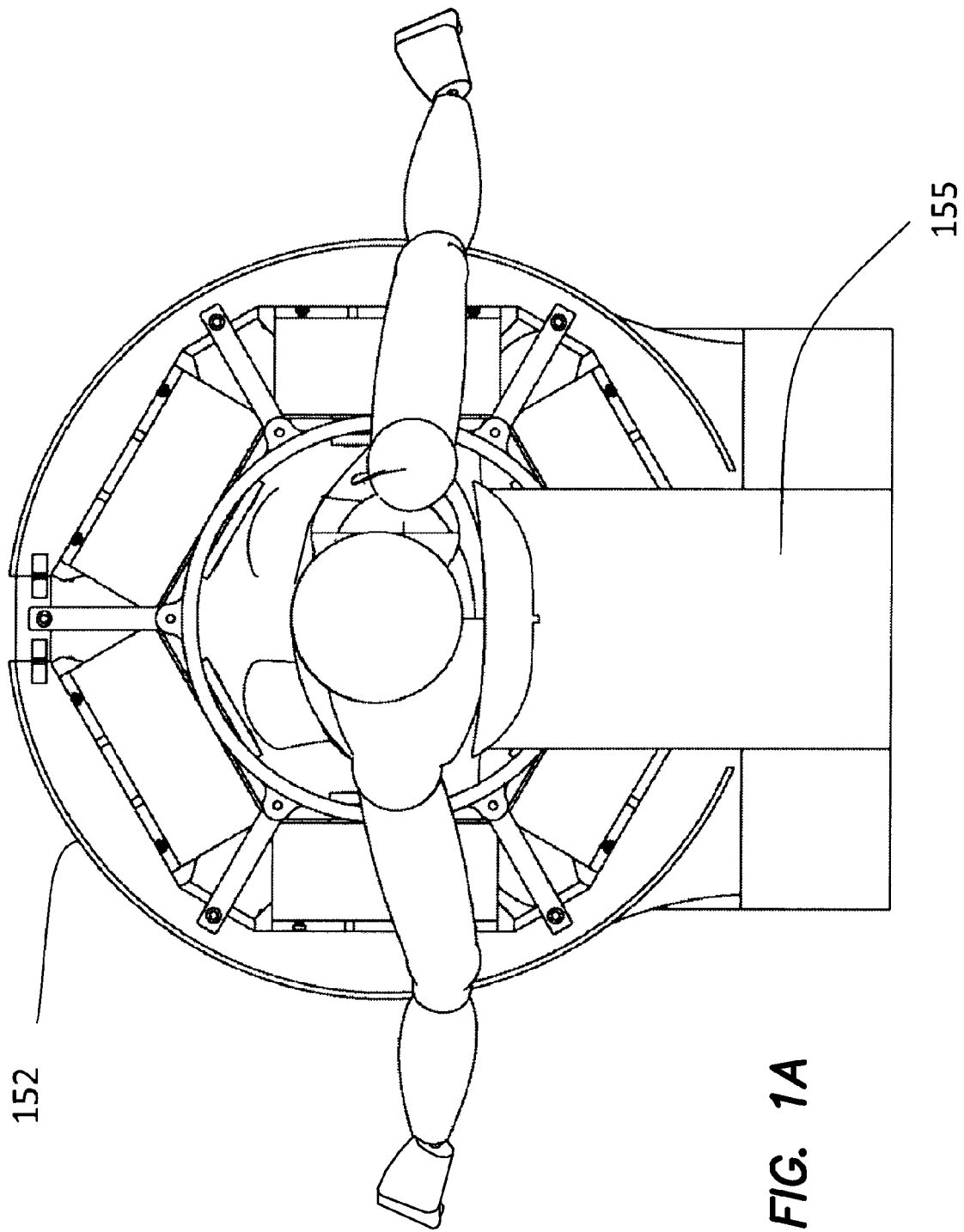
FIG. 1A is an end elevational view the MGCE apparatus in the direction of the patient's body axis as seen from the head.

FIG. 1A is an illustration showing the view along the patient's body axis as seen from the head and showing a different view of the magnetic chamber 152 and the bed control pedestal 155.

Figure 1B:
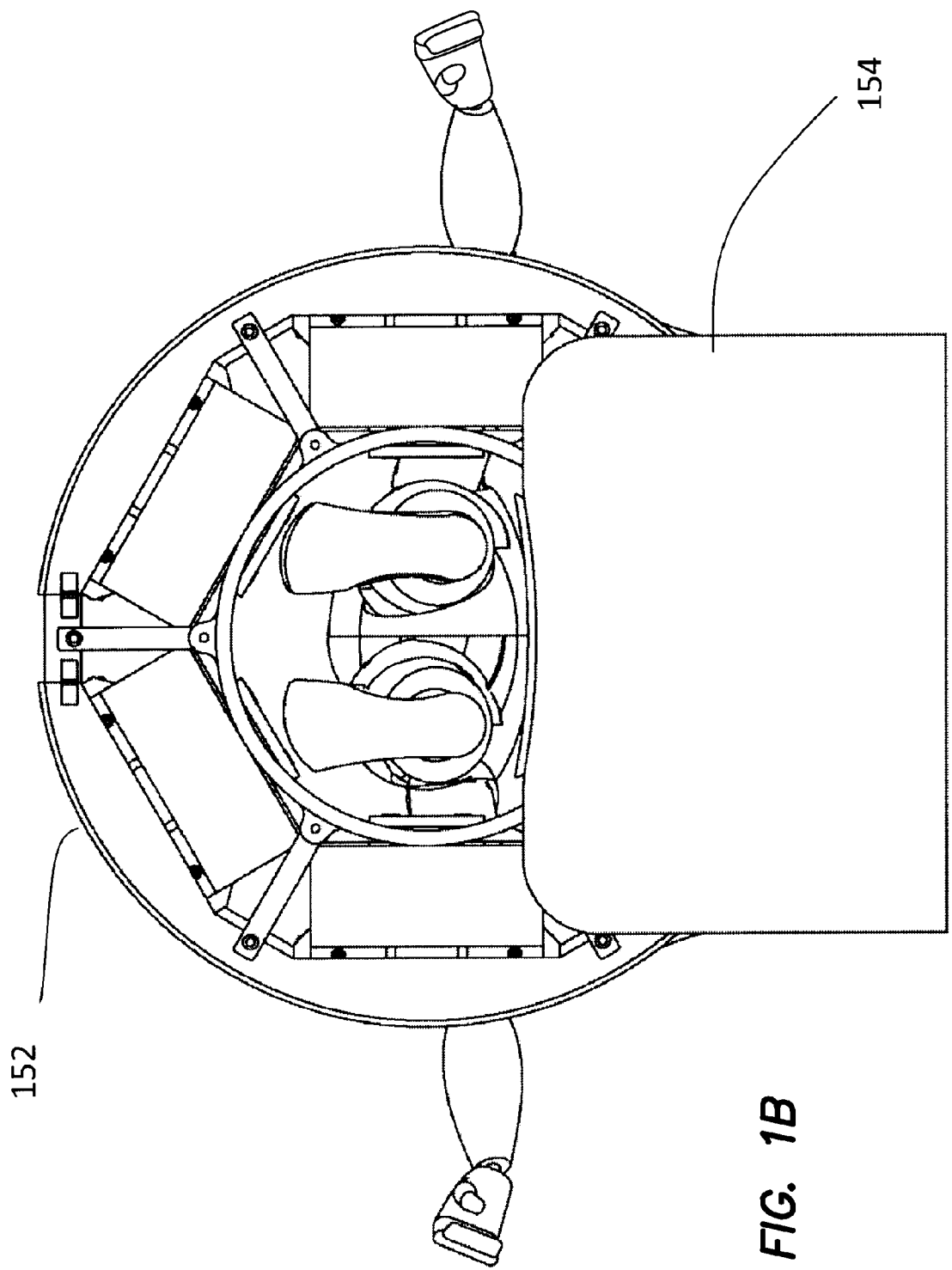
FIG. 1B is an end elevational view the MGCE apparatus in the direction of the patient's body axis as seen from the feet.

FIG. 1B is an illustration showing the view along the patient's body axis as seen from the feet and showing the magnetic chamber 152 and the power equipment base unit 154.

Figure 1C:
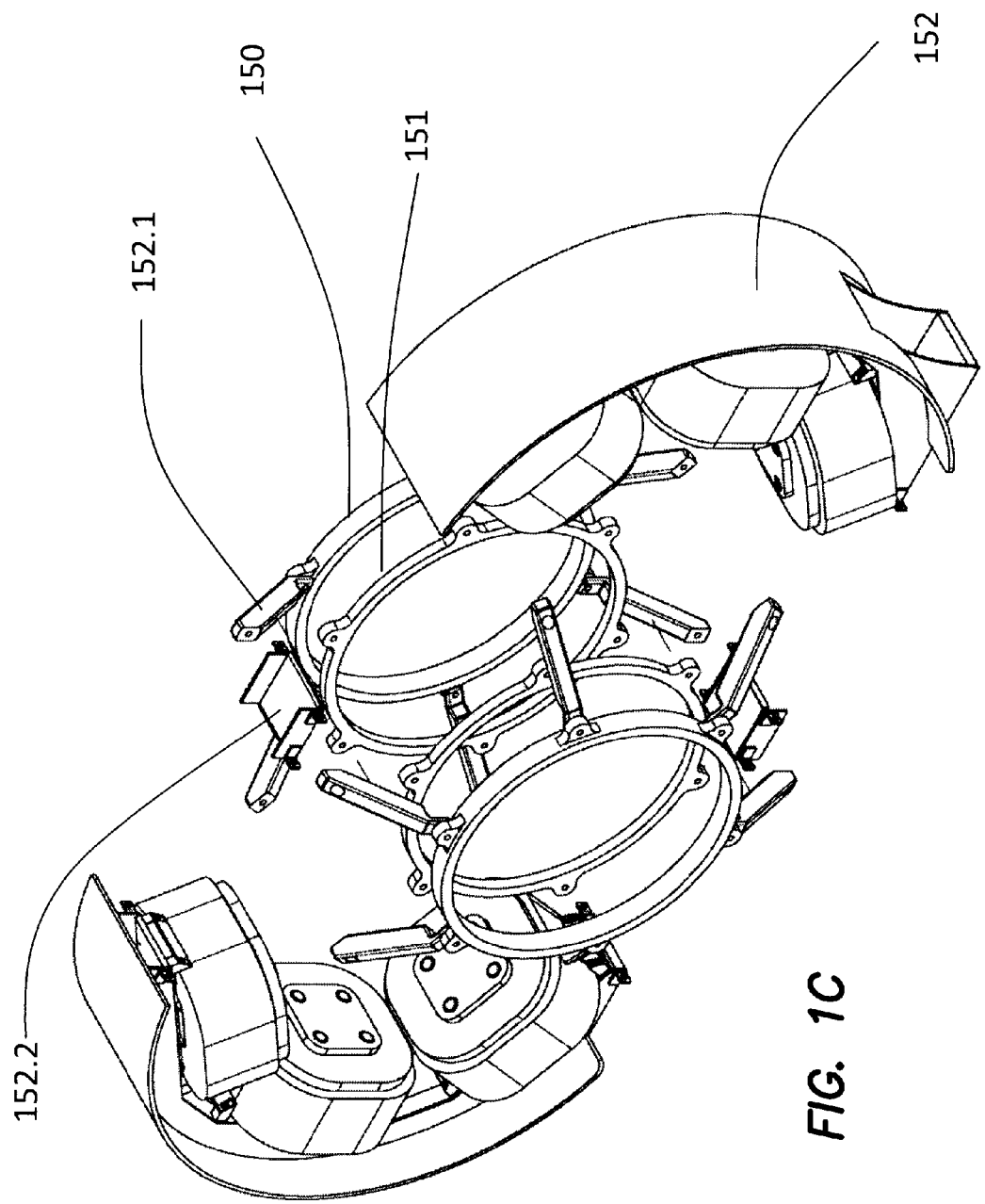
FIG. 1C is an exploded view of the magnetic structure.

FIG. 1C is exploded view of the magnetic structure. It is composed of two main half sections 152 joined together at the crown 152.2. Also shown are the lateral AC 151 and DC coil 150 rings, and the coil ring support bars 152.1. A fiberglass outer shell cover conceals all internal components. The outer shell can be any shape.

Figure 1D:
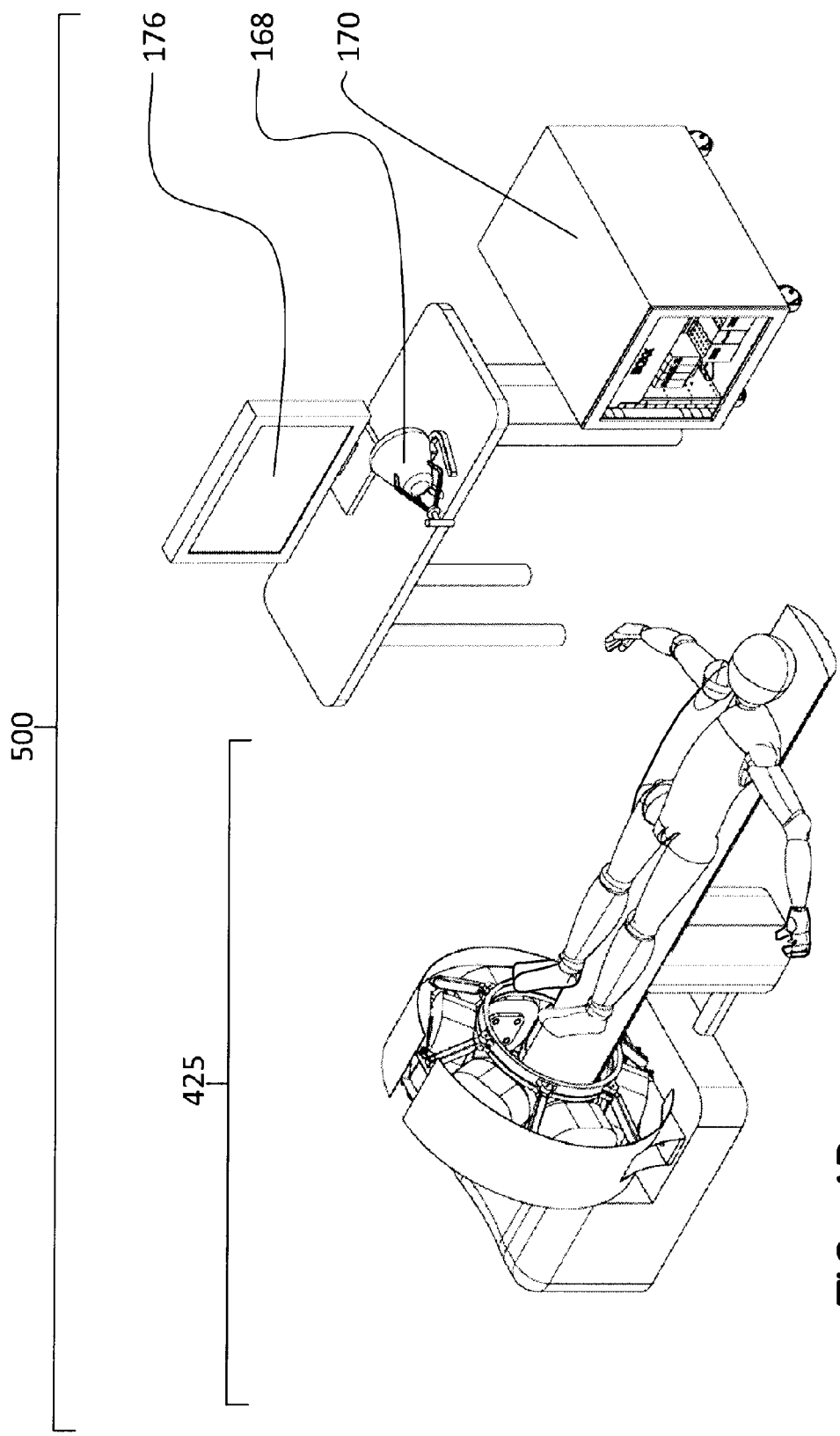
FIG. 1D is a perspective diagram of the entire MGCE system including the workstation and computer rack.

FIG. 1D is an illustration of the entire MGCE system including the workstation and computer rack. The MGCE system suite 500 includes the MGCE magnetic control assembly 425, control computer rack 170, user input joystick or three dimensional controller 168 and console display 176.

Figure 2:
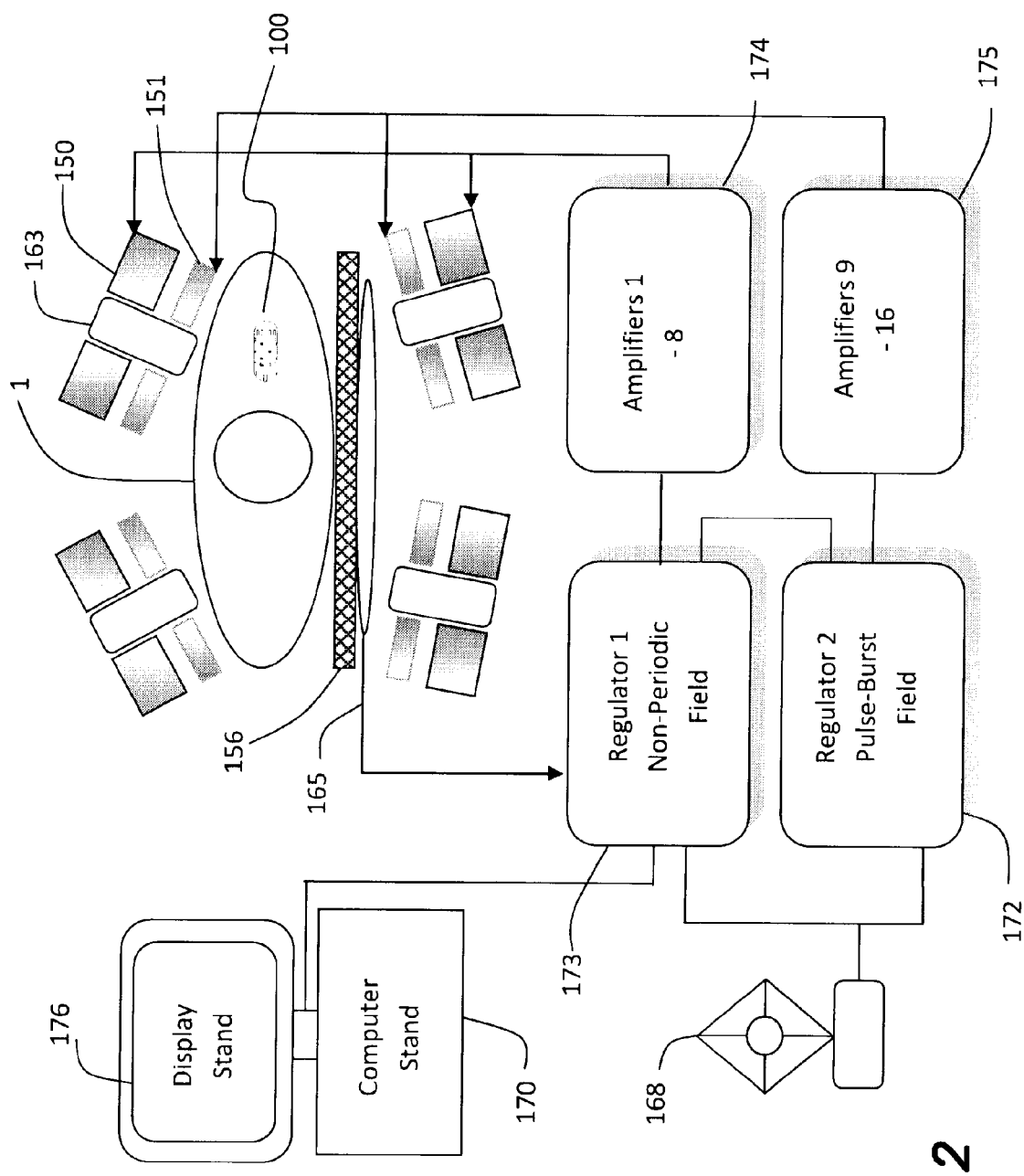
FIG. 2 is the MGCE system block diagram including the regulator, display and power components.

FIG. 2 is a MGCE system block diagram including the regulator, display and power components. The patient 1 is placed on the bed 156 and enters the system. The patient is surrounded by AC coils 151 and DC coils 150 which are mounted on a common laminate core 163. The capsule 100 is located by the position detection system 165 which interfaces with the DC regulator 173 which in turn interfaces with the AC pulse-burst regulator 172, which each control their respective DC and AC amplifiers 174, 175 to drive the DC and AC coils 150, 151 respectively. The user input is at the main console, which is comprised of a user input joystick or three dimensional controller 168, a computer console 170 and a display 176.

Figure 2A:
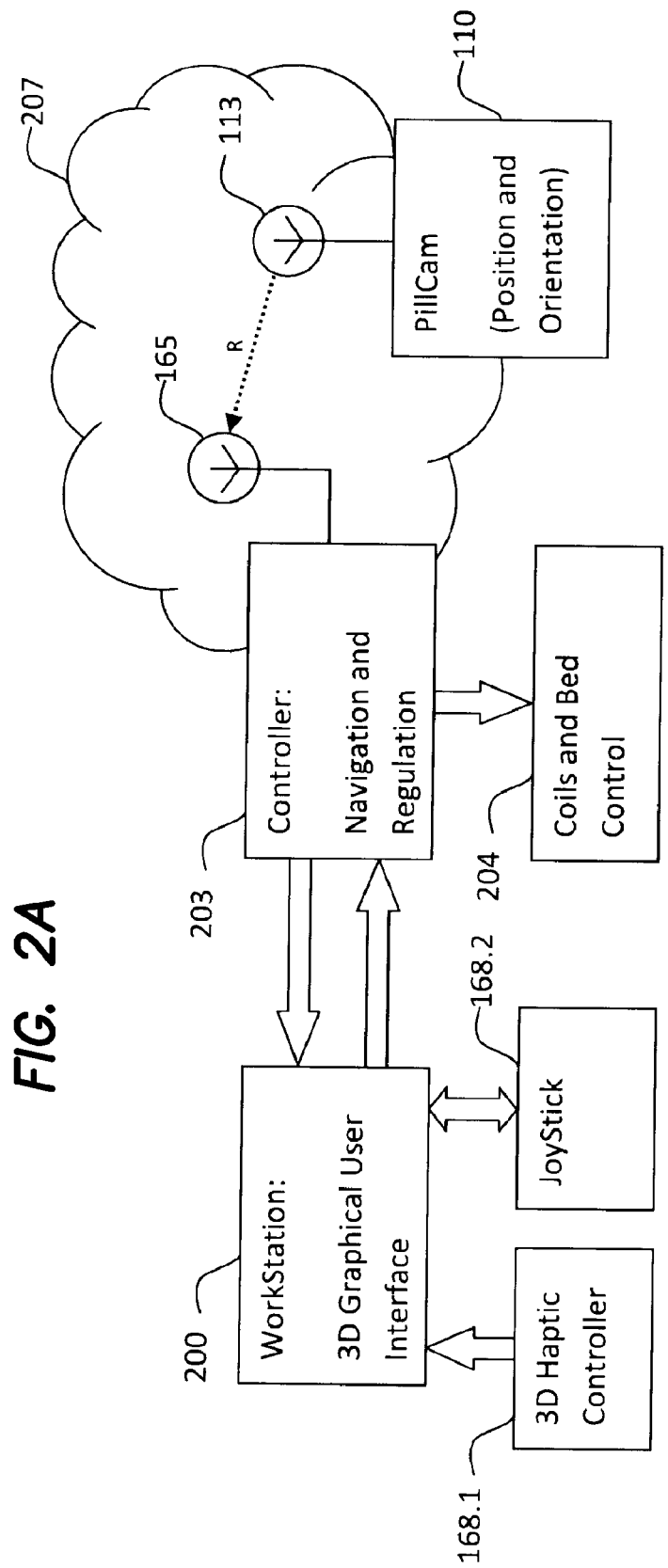
FIG. 2A is a diagram of the top level architectural components which constitute the untethered device navigation system.

FIG. 2A diagrams the hardware architecture of the MGCE navigation system. The work station 200 is the physician's interface to the capsule navigation system. The three dimensional haptic controller 168.1 and the joystick 168.2 are the physician's human interface devices (HIDs), which allow the physician to directly control the capsule using selectable ergonomic modalities of operation. The work station 200 and the controller 203 are connected via an ethernet cable for the bidirectional transmission of real-time parameters and commands using a custom fixed packet protocol, devised according to well understood conventional design principles. The controller contains the regulation system which adjusts the currents in the coil system and the position of the bed 204 in response to navigation commands received from the work station 200. The coil currents and bed position are adjusted to magnetically position the capsule 100 to the desired location. The controller receives position and orientation information from the capsule 100 via a wireless communication protocol through antennas 113, 165 connected to the controller and the capsule 100 respectively. The wireless communication range of the untethered capsule 100 is depicted symbolically with the cloud 207.

Figure 2B:
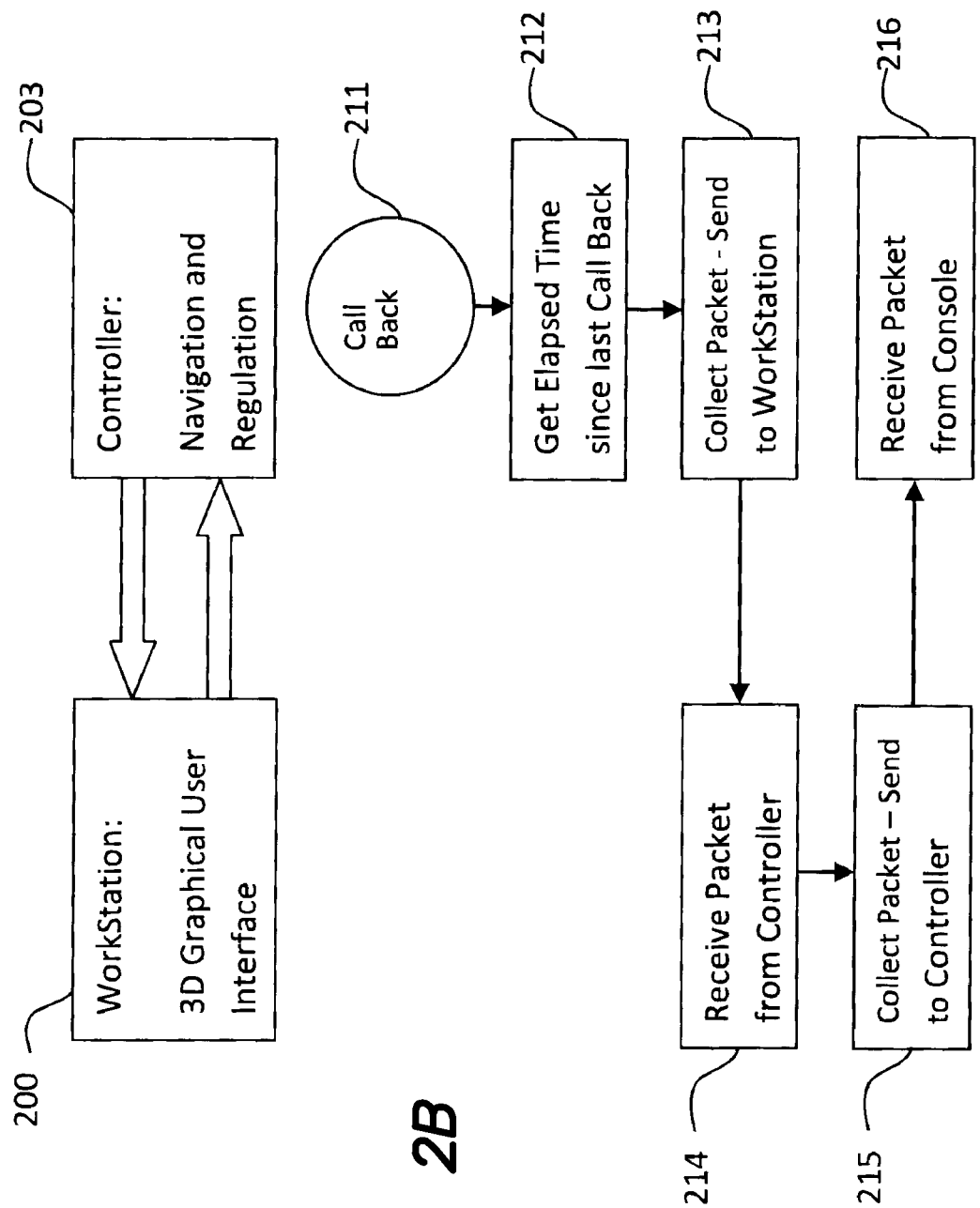
FIG. 2B a flow diagram which illustrates the communication sequence between the controller and the workstation.
Figure 3A:
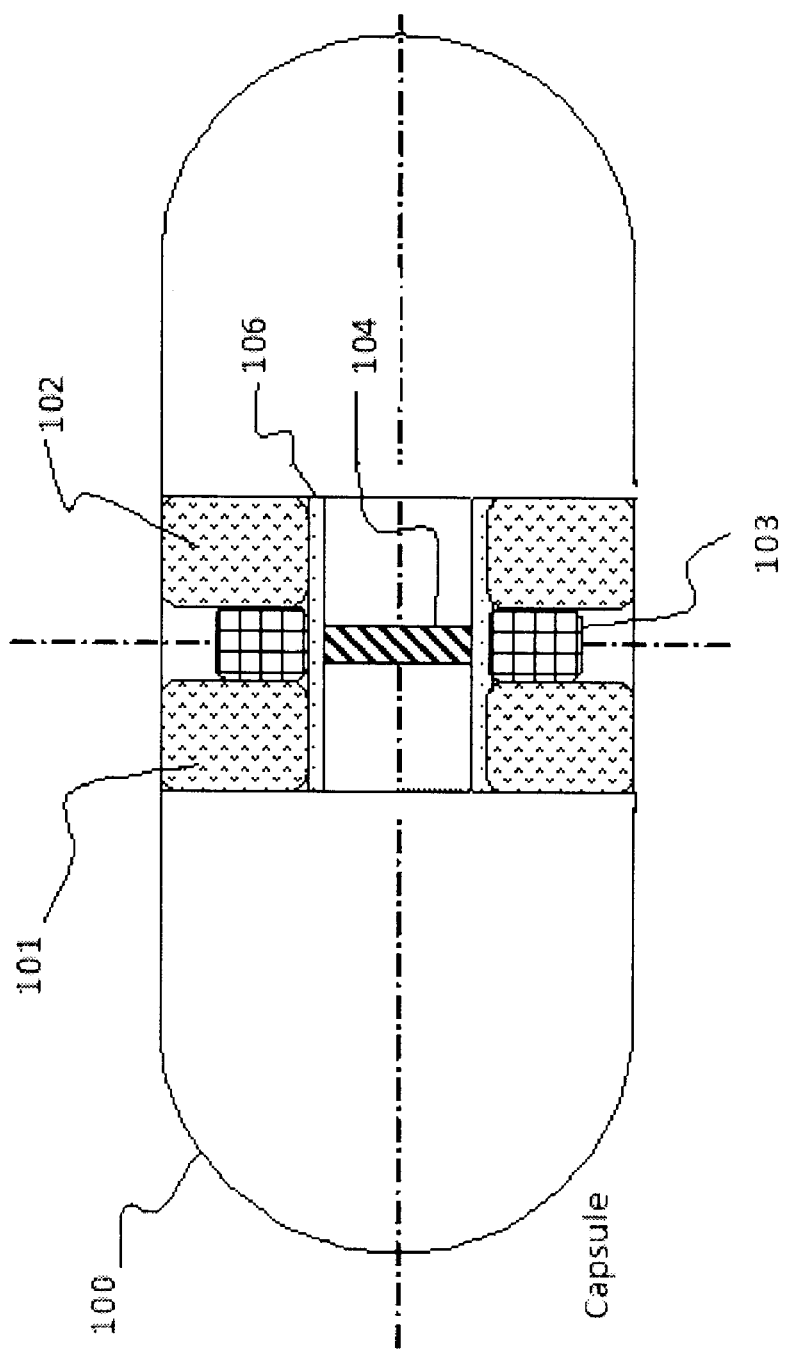
FIG. 3A is a side cross sectional view which illustrates the capsule with the basic embodiment of the electromagnetic capsule housed in the capsule.

FIG. 2B diagrams the real-time software communication system which allows the physician to seamlessly operate the navigation of the capsule 100 with minimal latency. The work station 200 and the controller 203 are connected via the fixed packet protocol. Communication is initiated on the controller 203 through a software CallBack step 211 or interrupt which occurs every five milliseconds. In order to compensate for any variation of elapsed time between sequential CallBack steps 211, a precision performance timer is used to determine the precise elapsed time from the previous call step 212. The packet to be sent to the work station 200 is then assembled at step 213. Information in this packet includes the elapsed time since the last CallBack 212, the position and orientation of the untethered capsule 100 and system health fields which will be displayed to the physician on the work station 200. The receive thread on the work station 200 receives the packet sent from the controller at step 214. The information received is parsed and interpreted by the appropriate work station subsystems. Position and orientation information is sent to the haptic controller handler which computes force feedback (FFB) direction and magnitude. The haptic controller is then updated to reflect these FFB settings. The packet is then processed by the user interface (UI) handler which updates the appropriate UI elements to reflect current navigation system settings and states. The receive thread on the work station 200 then collects the information needed on the controller at step 215. This packet is then returned to the controller at step 216. FIG. 3A is a cross-sectional illustration of the capsule 100 with its permanent ring magnets 101, 102, radially magnetized permanent ring magnet 103. Capsule 100 includes a conductive elements as part of, in or on either its surface or disposed internally within the capsule 100 in which element eddy currents are induced by an external AC magnetic field. The capsule 100 as disclosed herein includes various conductive or magnetic rings, cylinders 106, disks 104 or plates in which eddy currents can be induced. The eddy currents interact with an applied external DC or quasi-DC magnetic field to give rise to a net levitating force exerted on the capsule 100 under Lenz' law. The assembly shown on this cross section represents the propulsion elements of the capsule. Other elements have been omitted for the sake of ease of explanation. The ability of the capsule 100 to rotate, translate, and levitate within a body cavity is due to the principles associated with the formulation of Maxwell's, Faraday's, and Lenz' Laws as practiced by the illustrated embodiments of the invention, and should be apparent to a practitioner familiar with the art of magnetic guidance and control using permanent as well as electromagnetic radiation.

Figure 3B:
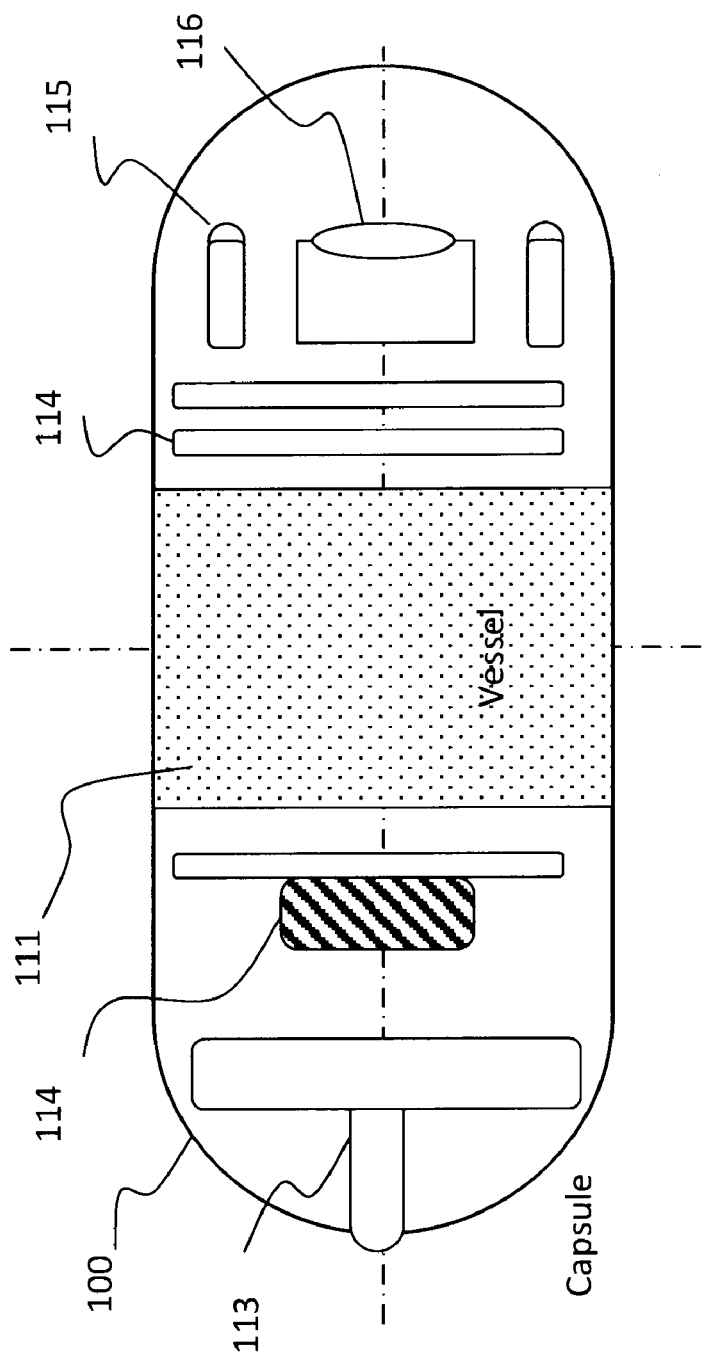
FIG. 3B is a side cross sectional view which illustrates a typical placement of medical devices within the capsule.

FIG. 3B is an orthographic cross section of one embodiment employing the capsule 100 to transport diagnostic as well as therapeutic devices, for example, a camera with lens 116, a LED 115, PCB's 114 for circuit conditioning and processing, an antenna 159 for bidirectional communication, and auxiliary medical equipment such as biopsy needle and other instruments 113. The above illustration indicates the possibility of employing the capsule 100 as a transport platform for other medical equipment to be performed by using an untethered device controlled by an electromagnetic field under the scheme noted by this invention. The central portion of capsule 100 is termed the vessel 111 and contains the propulsion elements of FIG. 3A.

Figure 4:
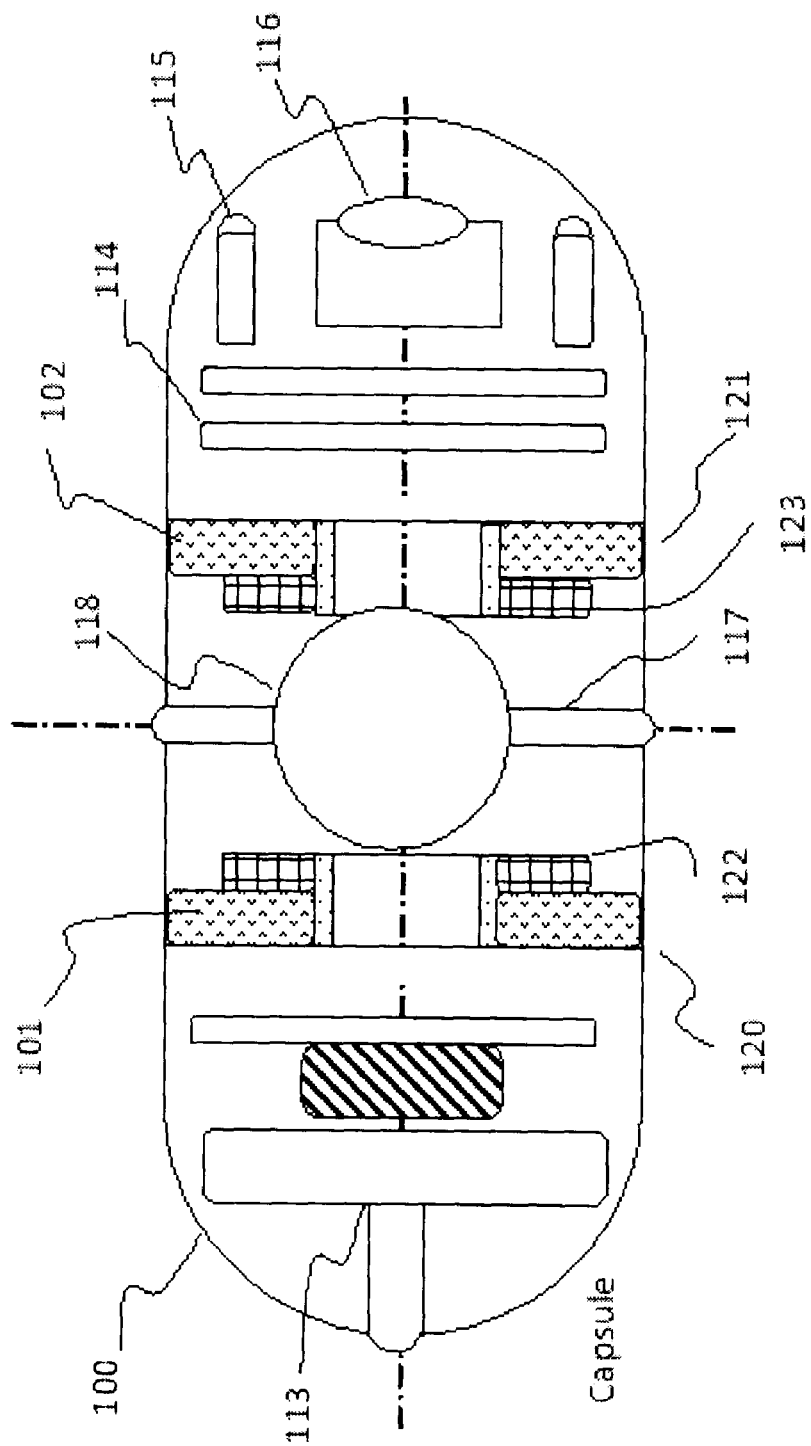
FIG. 4 is a side cross sectional view which illustrates a dual-capsule configuration with a suite of different medical devices placed in the capsule.

FIG. 4 further illustrates the embodiment of the invention noted in FIG. 3B. FIG. 4 shows the combination of a camera 116 with lens, LED 115, PCB's 114, permanent magnets 101, 102, a pump for delivering medication 118 and biopsy needle 113. FIG. 4 illustrates an embodiment of the capsule 100 constructed out of two symmetrical portions 120,121, enabling the insertion of a variety of medical instruments. An important detail of the propulsion scheme using radial inductive winding coils 122, 123 is also illustrated.

Figure 5:
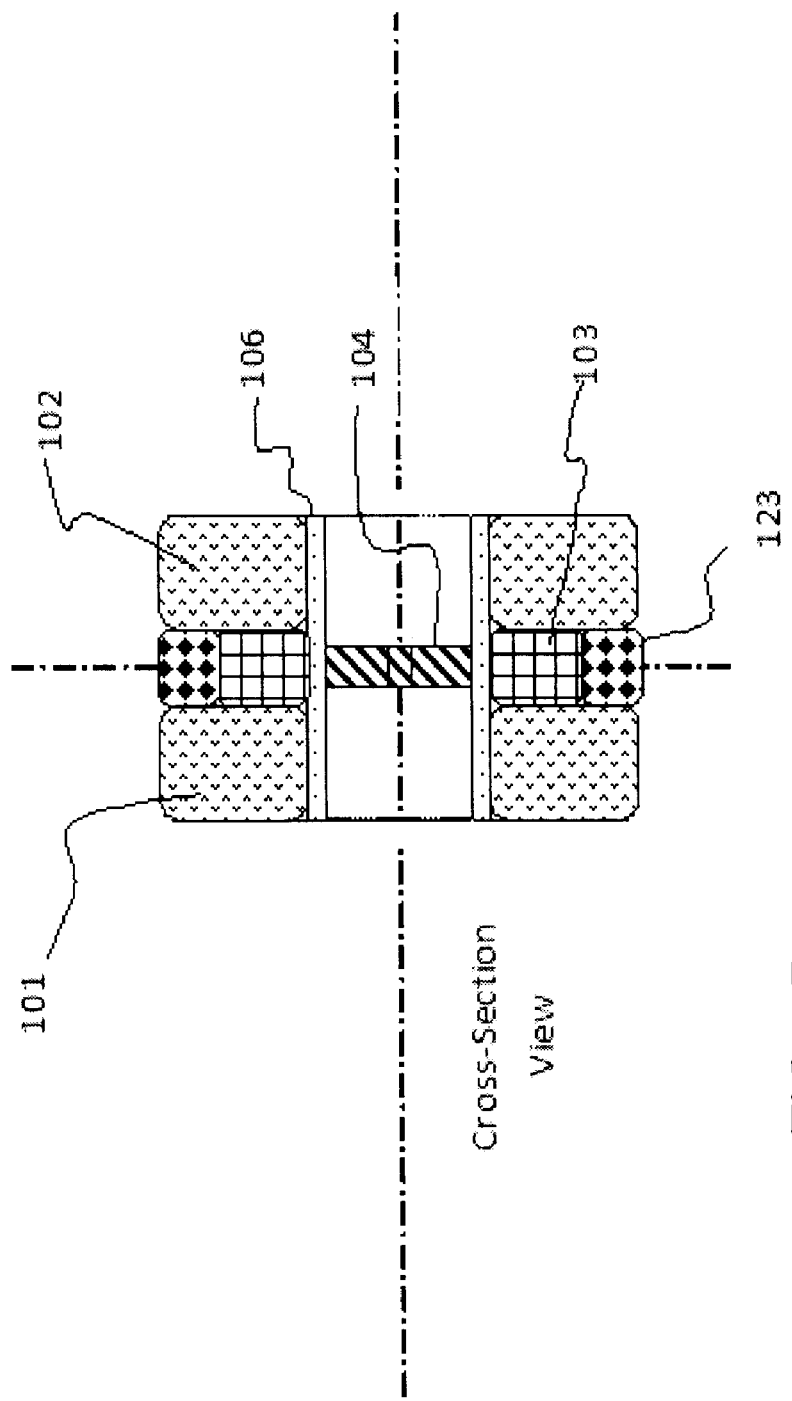
FIG. 5 is a side cross sectional view which shows the basic capsule constituents as one single unit comprised of two axially magnetized permanent magnets, a radially magnetized permanent magnet and three differently shaped conductor elements. A winding is inserted between the axially magnetized magnets for induced auxiliary power pick-up providing power for the capsule's internal electronics.

FIG. 5 is a cross-section view of the propulsion elements of the capsule 100, comprised of permanent magnets 101, 102, silver cylindrical holder (any other type of conductor or conductive material than silver may be substituted) 106, and a radially magnetized permanent magnet 103 with a vectorial oriented north pole 90 degrees relative to the long axis of magnetization of permanent magnet 101, 102. Additionally illustrated is silver disk 104 and winding coil 123. This illustration further illustrates an aspect of the capsule functionality by the locations of the permanent magnets 101, 102, radially magnetized permanent magnet 103 and two differently shaped conductive elements 104, and 106. Winding 123 is inserted between the axially magnetized 101 and 102 magnets for induced auxiliary power pick-up or battery charging providing power for the capsule's internal electronics.

Figure 6A:
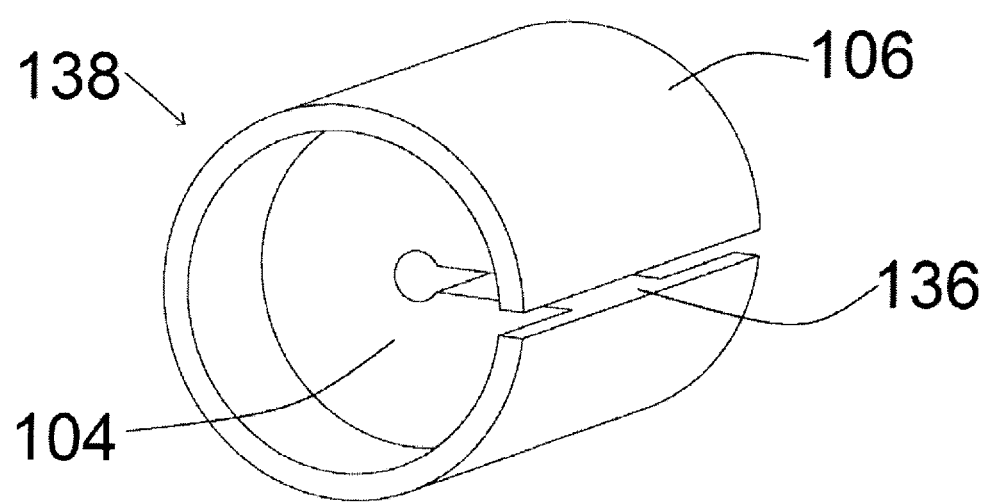
FIG. 6A is a perspective view which shows the unique slit feature of the cylindrical conductive elements in FIG. 5. The cut disconnects conductive halves of the elements reducing parasitic circulating currents.

FIG. 6A illustrates the silver-coated fully-split cylindrical assembly 138, in one of the embodiments of the invention. The assembly 138 is comprised of slotted cylinder 106 with a longitudinally defined slot defined through it and an internal silver element 104, with a connected radial slot or gap 136 defined in cylinder 106 and disk 104. The cylinder 106 carries adjacent ring magnets 101 and 102 and coil 103 as shown in FIG. 3A. The AC magnetic generator, comprising of eight coils (not shown) 162, generates an alternating field inducing eddy currents which flow on the surface of the elements 106 and 104. The slot 136 functions to electrically disconnect conductive the upper and lower halves of these elements as shown in FIG. 6A, reducing the parasitic circulating currents. If the embodiment did not comprise a separation slot 136 along the radial dimension of the cylinder 106 and disk 104, the eddy currents generated from eight AC coils would induce circulating eddy currents in opposite directions, reducing the efficiency of the assembly as it is being levitated under the Lenz Law principle.

Figure 6B:
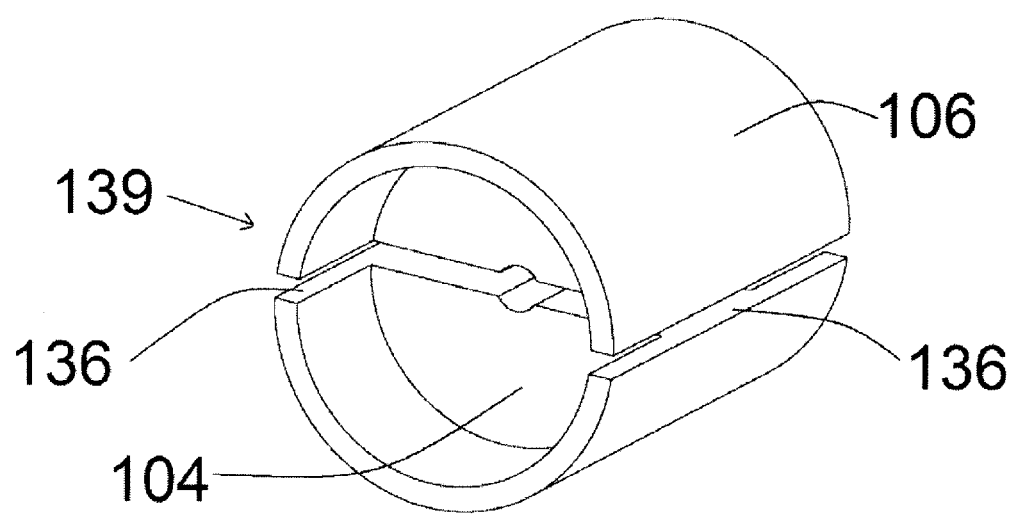
FIG. 6B is a perspective view which is an alternative embodiment of the conductive elements of FIG. 5. In this embodiment the elements are cut only partially directing the capsule induced currents differently from the fully cut elements of FIG. 6A.

FIG. 6B embodies an example of an alternative formulation of the conductive elements previously explained in FIG. 5. FIG. 6B illustrates an embodiment of the silver-coated half-split cylindrical assembly 139, and shows the slit feature of the cylindrical conductive elements 106 in FIG. 5, where assembly 139 is seen in side cross section showing one half of the split cylinder. As a functional unit, the silver-coated full-split cylindrical assembly 139 enables the capsule 100 to function by performing the task of the conductor element for this invention. In this embodiment the elements are fully cut via the slot 136, thereby directing the induced currents in a manner that differs from the partially cut elements of FIG. 6A. Each of the divided portions of the cylinder 106 and disk 104 are coupled or bonded to ring magnets 101, 102 and/or coil 103 and are thus held apart in position. However, it is also possible that an insulator could be disposed between the divided portions to independently space the portions apart without necessarily being bonded to ring magnets 101, 102 and/or coil 103. The illustrated embodiment shows cylinder 106 and disk 104 being divided by slot 136 into two equal halves. However, it is also within the scope of the invention that slot 136 could divide cylinder 106 and disk 104 into two unequal portions.

Figure 7:
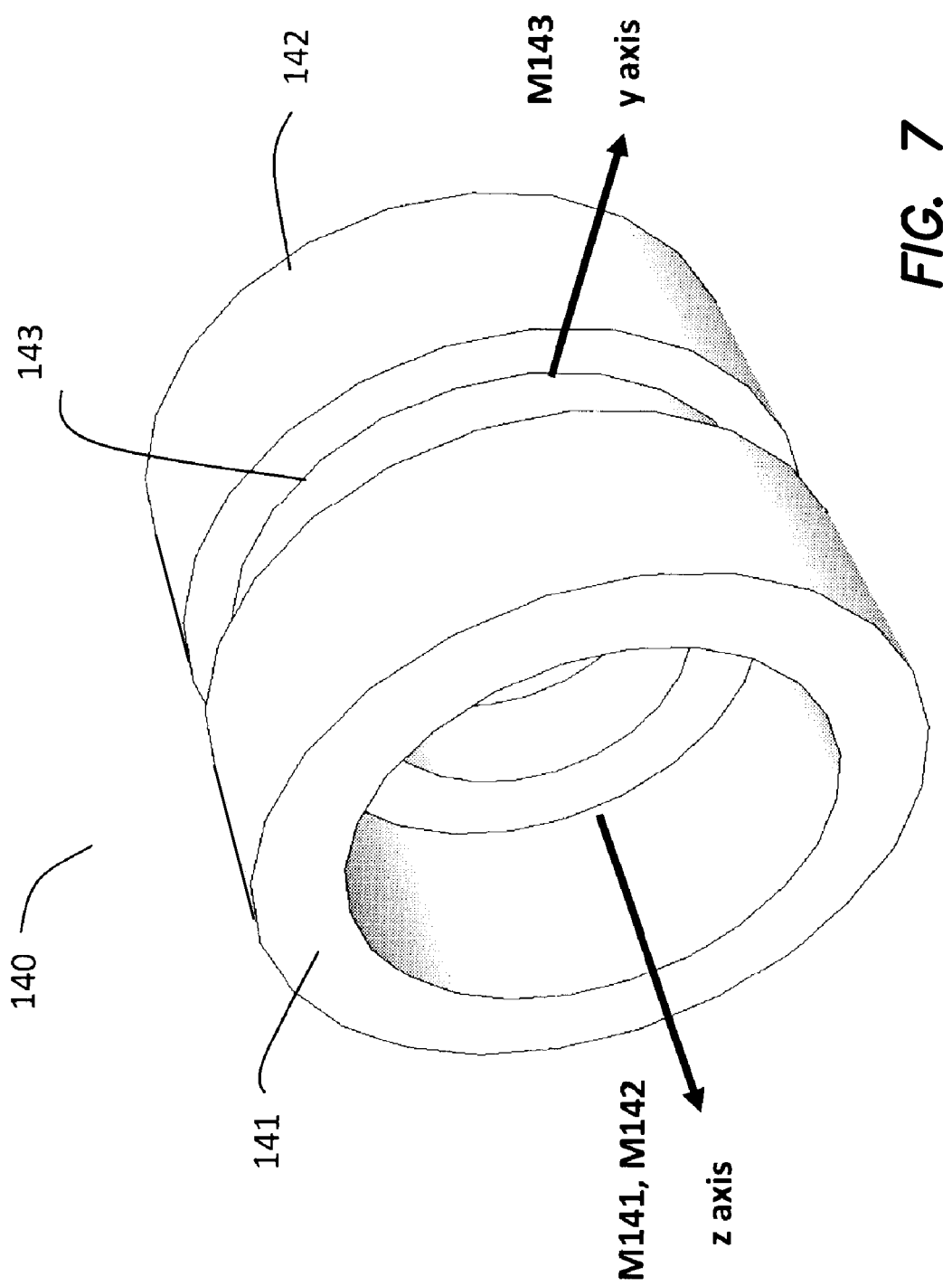
FIG. 7 is a perspective view which shows the capsule magnetization directions for axially magnetized permanent magnets, and the radial magnetization direction.

FIG. 7 provides an orthographic illustration of a preferred embodiment of the invention using permanent magnet assembly 140 comprised of permanent magnets 141, 142, while the magnetization direction shown along the Y axis is noted by M143 and the magnetization Z axis is shown by M141 and M142. The magnetizations along the axes are essential elements forming the propulsion mechanism induced by the electromagnet (not shown). Further figures and descriptions will illustrate the importance of such an embodiment and the relevance of the physical groove separation 143 between said permanent magnets 141, 142, furthering their function as described below. The magnetization directions (not shown) for axially magnetized permanent magnets 141, 142 and the radial magnetization direction for magnet 143 is generated along an anisotropic axis along Z direction to enable rotation, translation, pivoting, and levitating the assembly 140.

Figure 8:
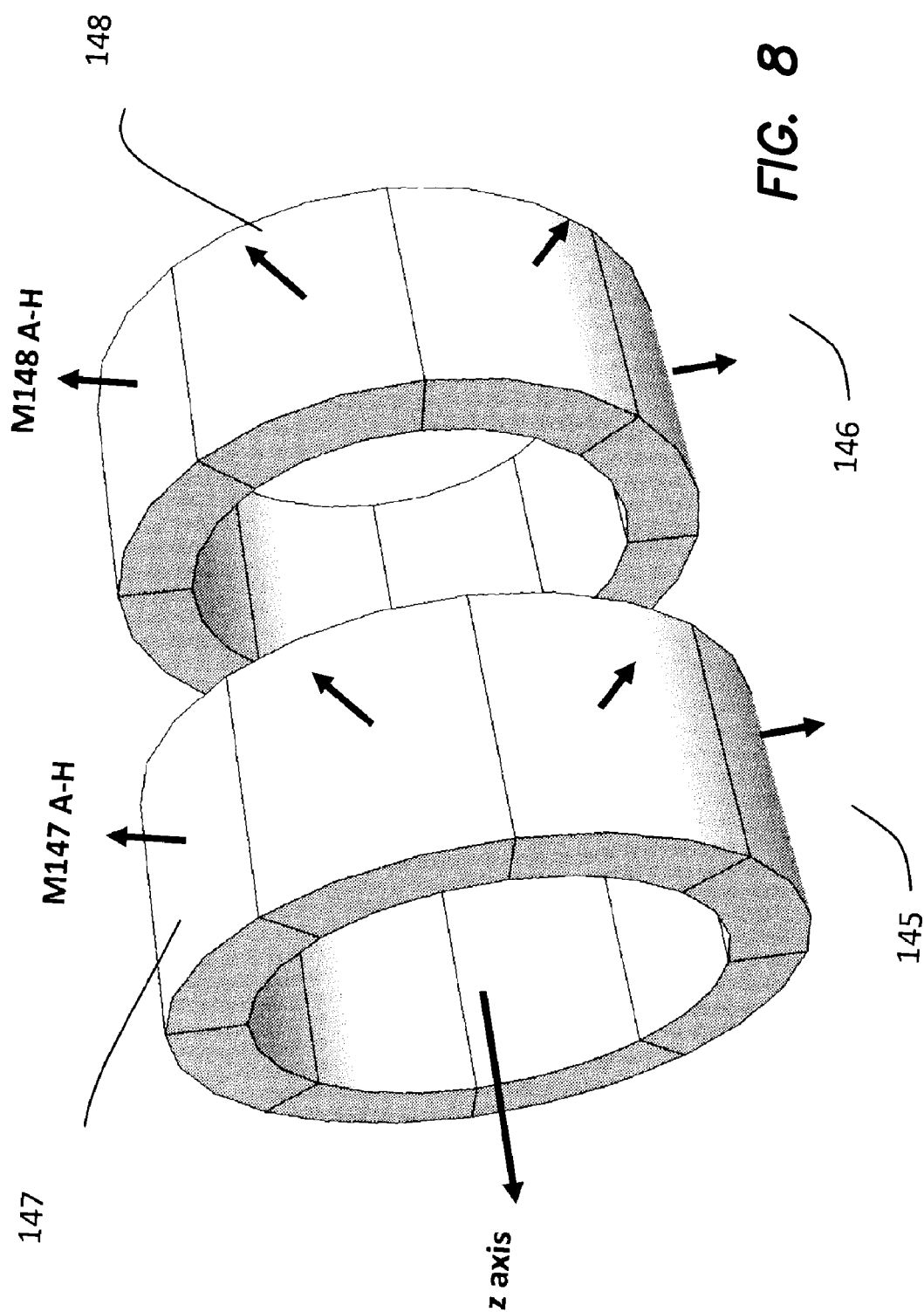
FIG. 8 is a perspective view which shows another embodiment of the permanent magnets using radially magnetized segments assembled into rings having the same size as the corresponding magnets in FIG. 5.

FIG. 8 orthographically illustrates a further embodiment of the permanent magnets 147 with its permanent magnets individually magnetized to generate polarization along the lines noted by reference numeral 145, namely having opposing permanent magnetic pole faces centered on the inner and outer radial surfaces of a cylindrical segment. Magnet assembly 148 is similarly formed out of eight permanent magnets, each magnetized along the main axis, as noted by reference numeral 146. The resultant assembly of eight M147 elements will generate a resulting vector along the Z main long axis to enable efficient navigation of the propulsion capsule. Using radially magnetized segments M147 and M148 assembled into magnetic assembly rings 147, 148 having the same size as the ring magnets in other embodiments enabled performance according to the invention as intended by resulting in a magnetic moment isotropically along the Z axis.

Figure 9:
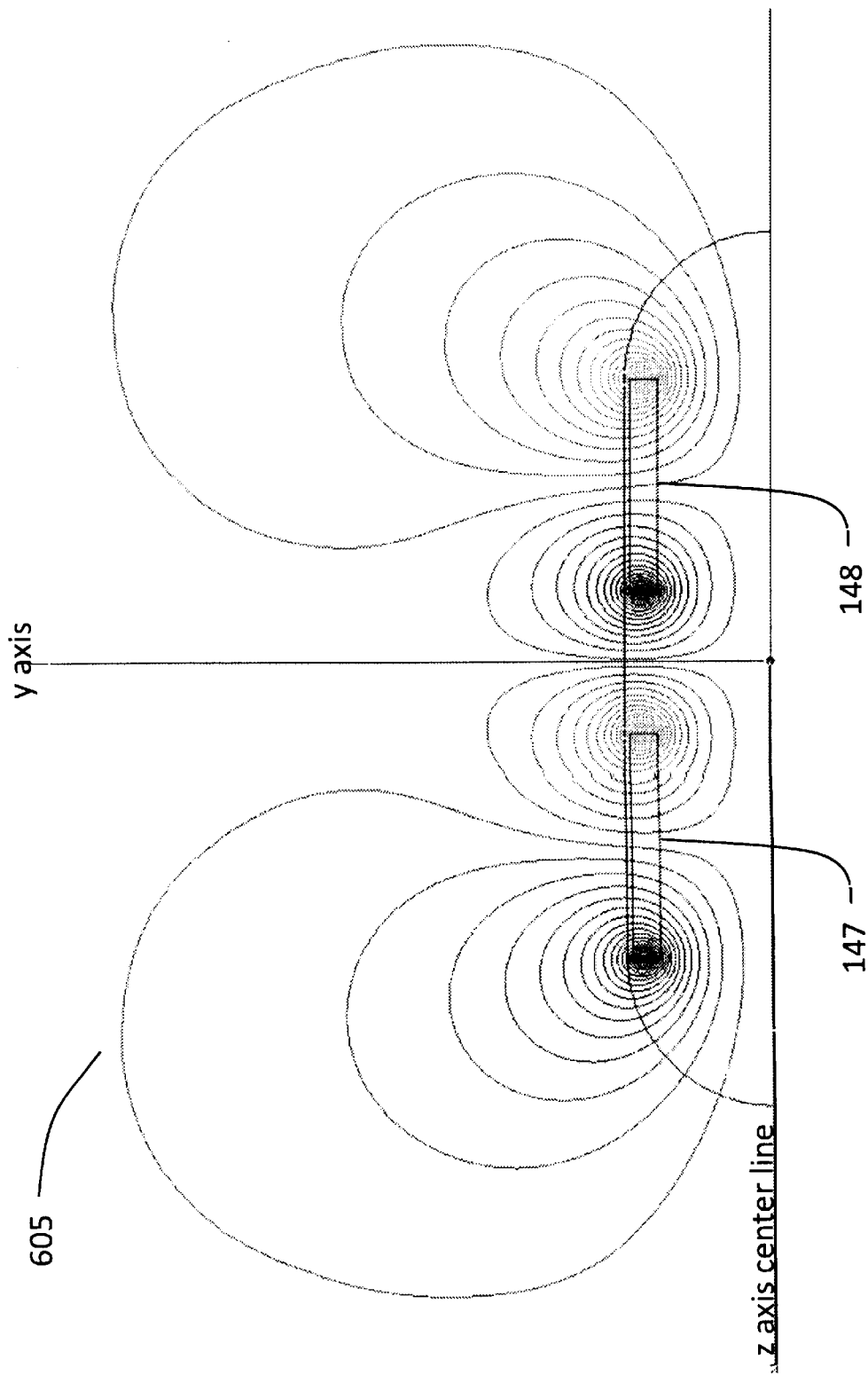
FIG. 9 is a half side cross sectional view which provides a representation of the magnetic flux lines for the segmented radial magnetization shown in FIG. 8 at the top cross section of the rings.

FIG. 9 illustrates a representation of the magnetic flux lines 605 for the segmented radial magnetization shown in FIG. 8 at the top cross section of the rings 147, 148. Magnetic flux lines generated by radial magnetization formed using assemblies such as shown in FIG. 9 allow the magnetic assembly rings 147, 148 to develop isotropy, or vector direction independence, due to the shaped magnetic geometry resulting from the magnetic flux lines 605, as noted by the illustration.

Figure 10:
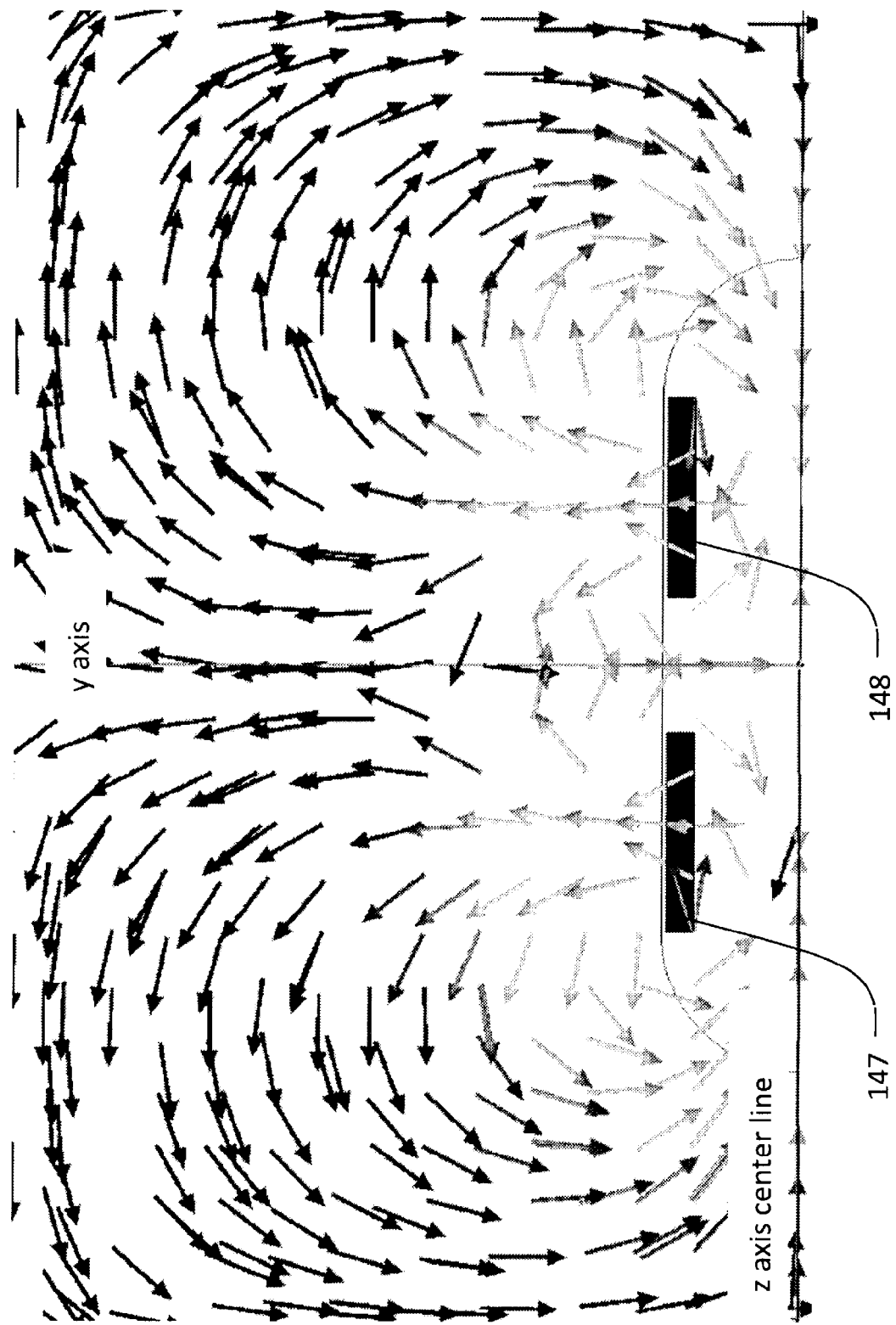
FIG. 10 is a half side cross sectional view which is a graphic representation of the magnetic field vector distribution for the segmented radial magnetization shown in FIG. 8 at the top cross section of the rings. The field distribution capsule is cylindrically symmetrical around the capsule.

FIG. 10 is a representation of the magnetic field vector distribution for the segmented radial magnetization also illustrated in FIG. 9 at the top cross section of the magnetic assembly rings 147, 148. The said field distribution is cylindrically symmetrical around the capsule 100.

Figure 11:
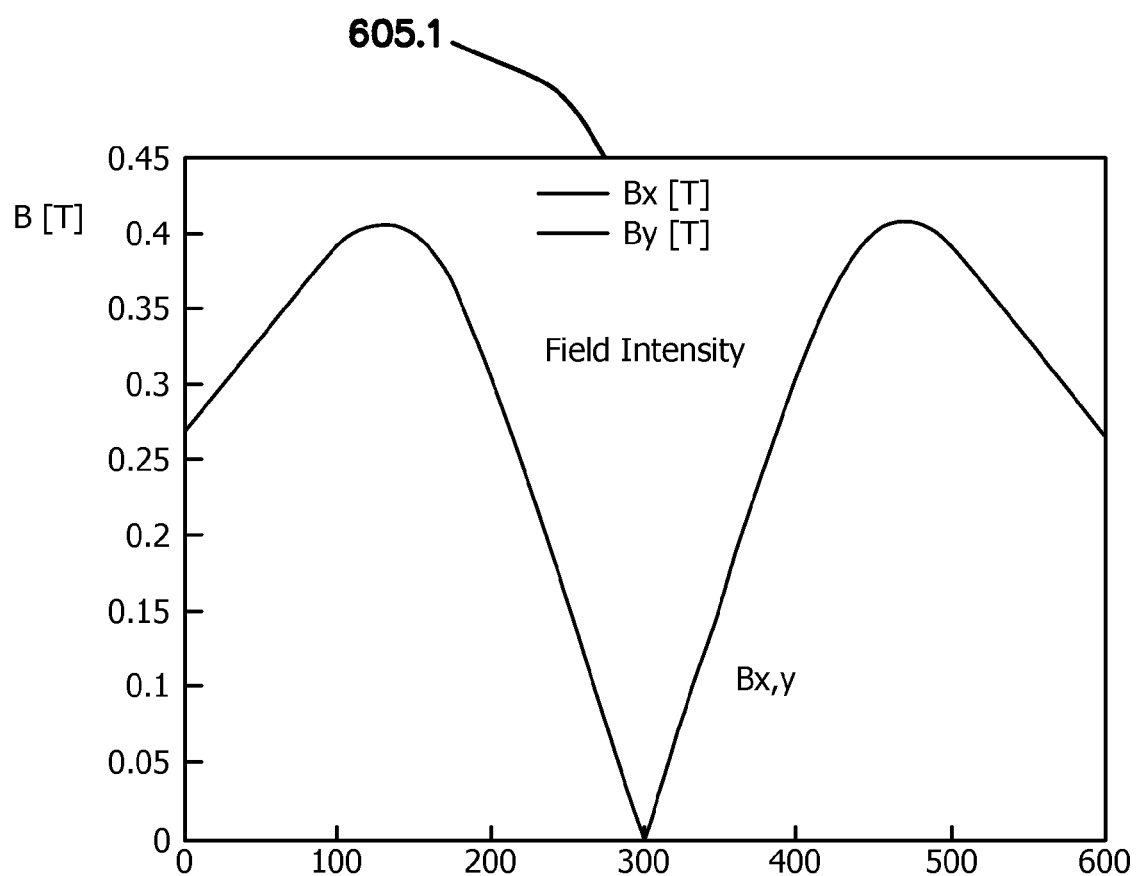
FIG. 11 is a graph of magnetic field strength verses distance of the x and y components of the magnetic field B illustrating the magnetic vortex generated by the capsule nonperiodic field generator of FIG. 13.
Figure 13:
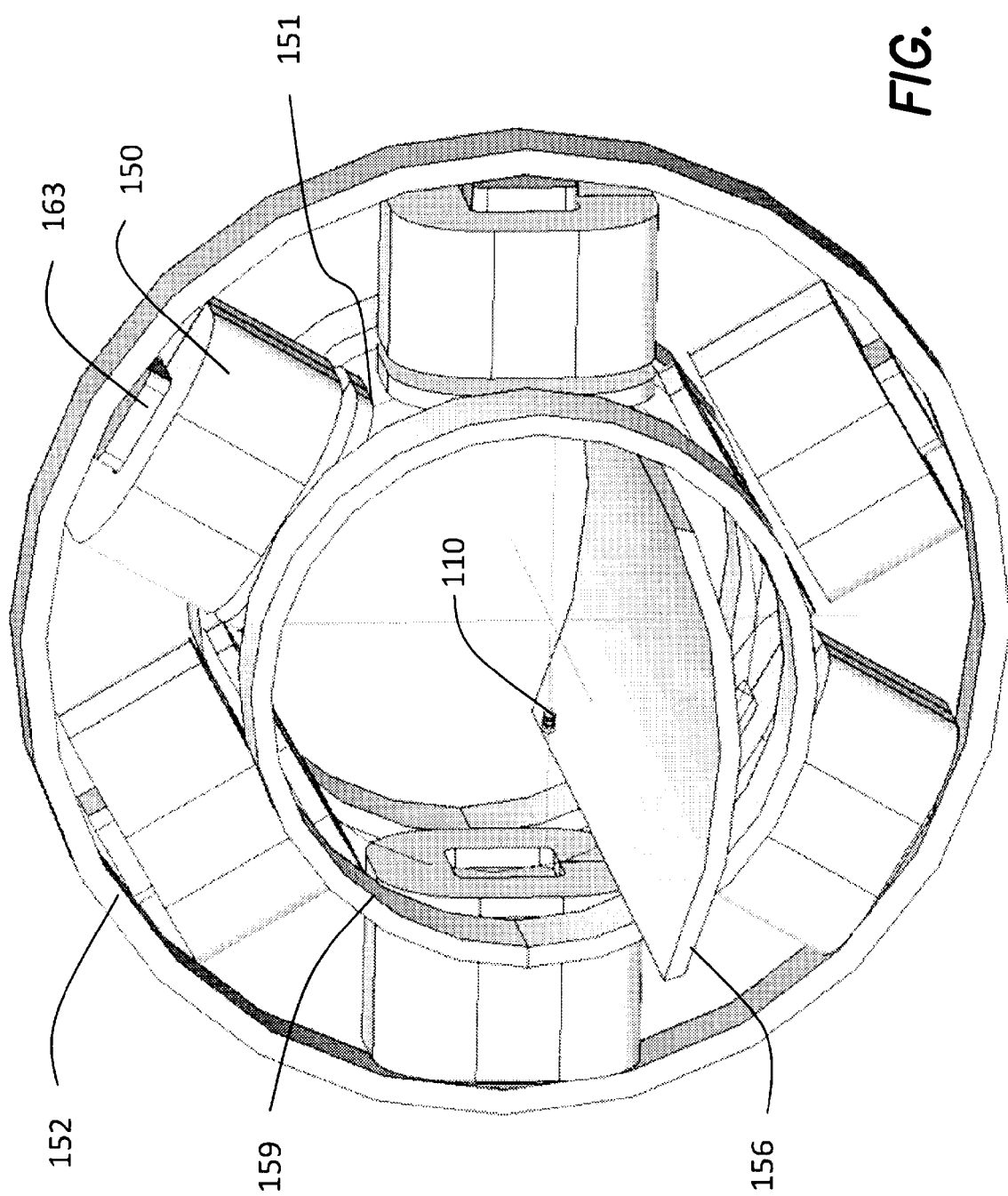
FIG. 13 is a perspective diagram of the field generator and also a magnetic simulation model of the capsule complete nonperiodic and pulsed-burst field generators with eight and eight coils for each type of field respectively.

FIG. 11 provides a graph of the magnetic gradient generation of field intensity with centered magnetic vortex 605.1 generated by the nonperiodic field generator of FIG. 13.

Figure 12:
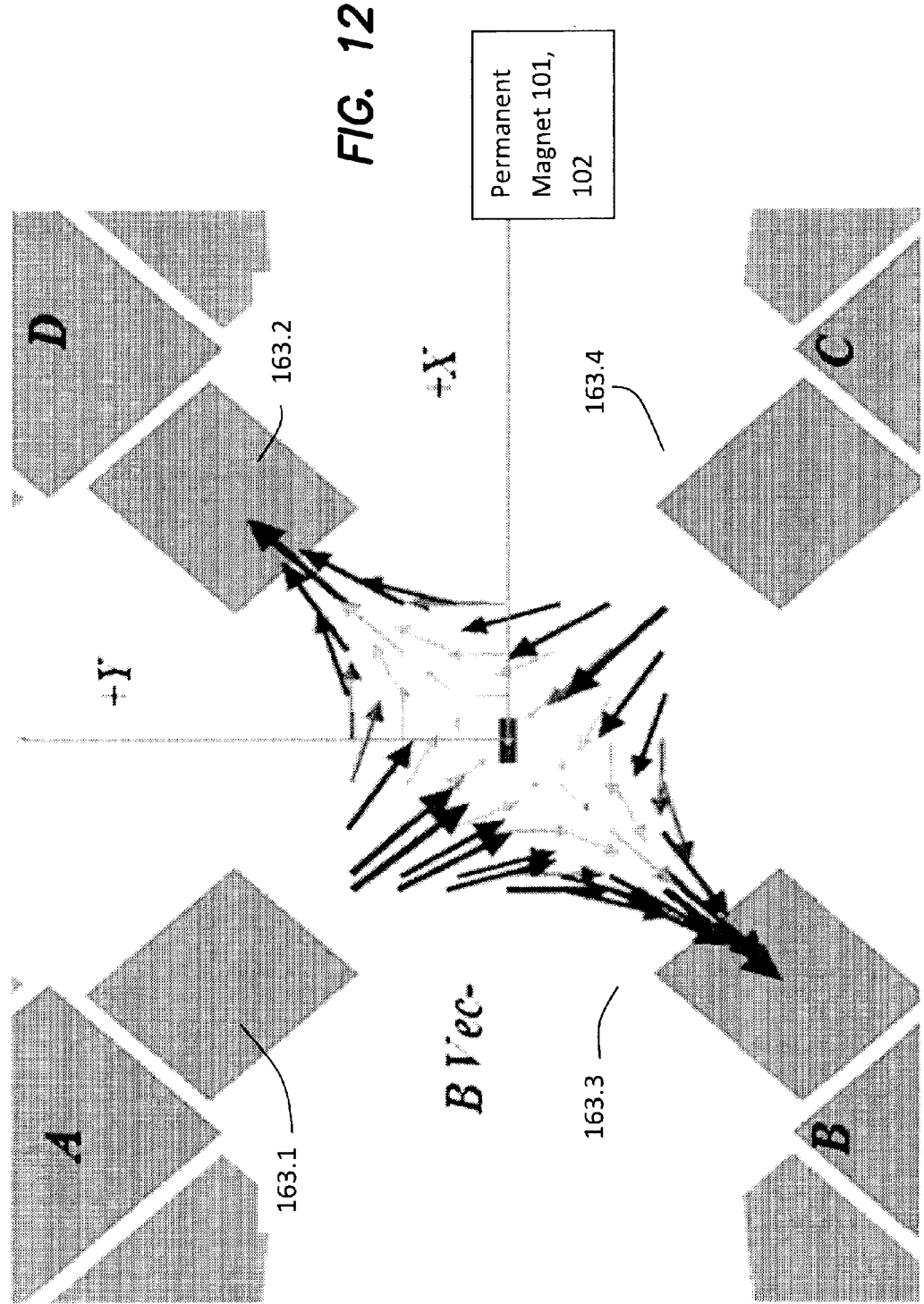
FIG. 12 is a vector field graph of an inverted magnetic vortex generated by the nonperiodic field generator of FIG. 13.

FIG. 12 is a graph of an inverted magnetic gradient vortex generated by the nonperiodic field generator of FIG. 13. The permanent magnet segments 101, 102 are visible in the center of the vortex, while the magnetic gradient vortex is generated through electromagnetic DC pole faces 163.1, 163.2, 163.3, 163.4. Electromagnetic currents generated by DC pole faces 163.1, 163.2, 163.3, 163.4 create a boundary condition enabling the capsule 100 to lie along the +X axis, perpendicular to the +Y axis representing one of multiple singularities of the preferred embodiment. A person familiar with the art could alter the magnetic direction of any of the DC pole faces 163.1, 163.2, 163.3, 163.4 to rotate the capsule 100 in any one of the directions between +X, −X, +Y, −Y, and any combination thereof to navigate the capsule 100 along a body cavity with full six degrees of freedom. FIG. 12 illustrates a simplified model in two dimensional space, whereas the full embodiment of this invention envisions a total of sixteen electromagnets of both AC and DC type, enabling a full six degrees of freedom of movement of the capsule 100 within a body cavity in three dimensional space.

FIG. 13 is a schematic of the field generator and also a magnetic simulation model of the complete non-periodic and pulsed-burst field generators with eight DC and eight AC coils for each type of field respectively. The embodiment of the assembly shown is comprised of the circular armature 152 forming the return path of the stray magnetic fields from the electromagnet DC coils 150, AC coils 151, with its common laminated core 163. The assembly further is formed by cylindrical coil 159 and the patient bed 164, illustrating possible location of the capsule 100 within the chamber. The geometry and topological layout of the spherical chamber represents one of the embodiments of this invention as it enables the magnetic field emanating from the eight DC coils 150 combined with the eight AC coils 151 to form a homogeneous field within the effective space of the chamber, hence provide for a linear computational model without the complexity of a nonlinear field generated other than this spherical arrangement.

Figure 14:
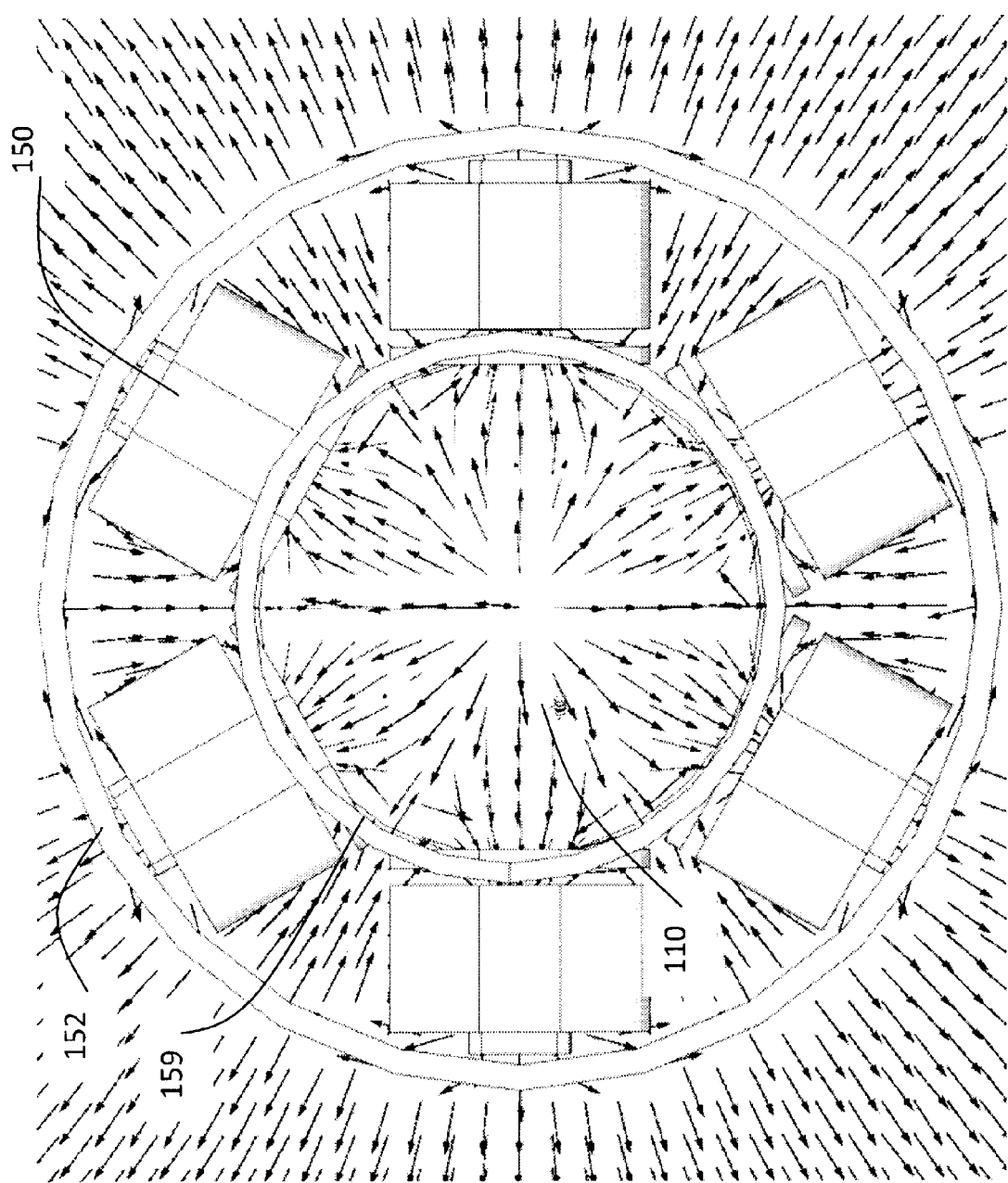
FIG. 14 is a vector graph representing the fields generated by all coils of the field generator of FIG. 13. The magnetic vortex is at the center from which the field-vectors originate and fan out symmetrically into each of the coils. This center is moved and shaped by independently controlling the coil currents.

FIG. 14 is a vector graph representing the field vortex 110 generated by all coils of the field generator of FIG. 13. The magnetic vortex is at the center from which the field-vectors originate and fans out symmetrically into each of the coils. This center is moved and shaped by independently controlling the coil currents. The apparatus noted by FIG. 14 is a further illustration for the embodiment of forming a homogeneous field, dynamically shaped to enable the movement of the capsule 100 without loss of linearity. FIG. 14 further illustrates the location of the armature 152, the circular coil 159, and the DC coils 150.

Figure 15:
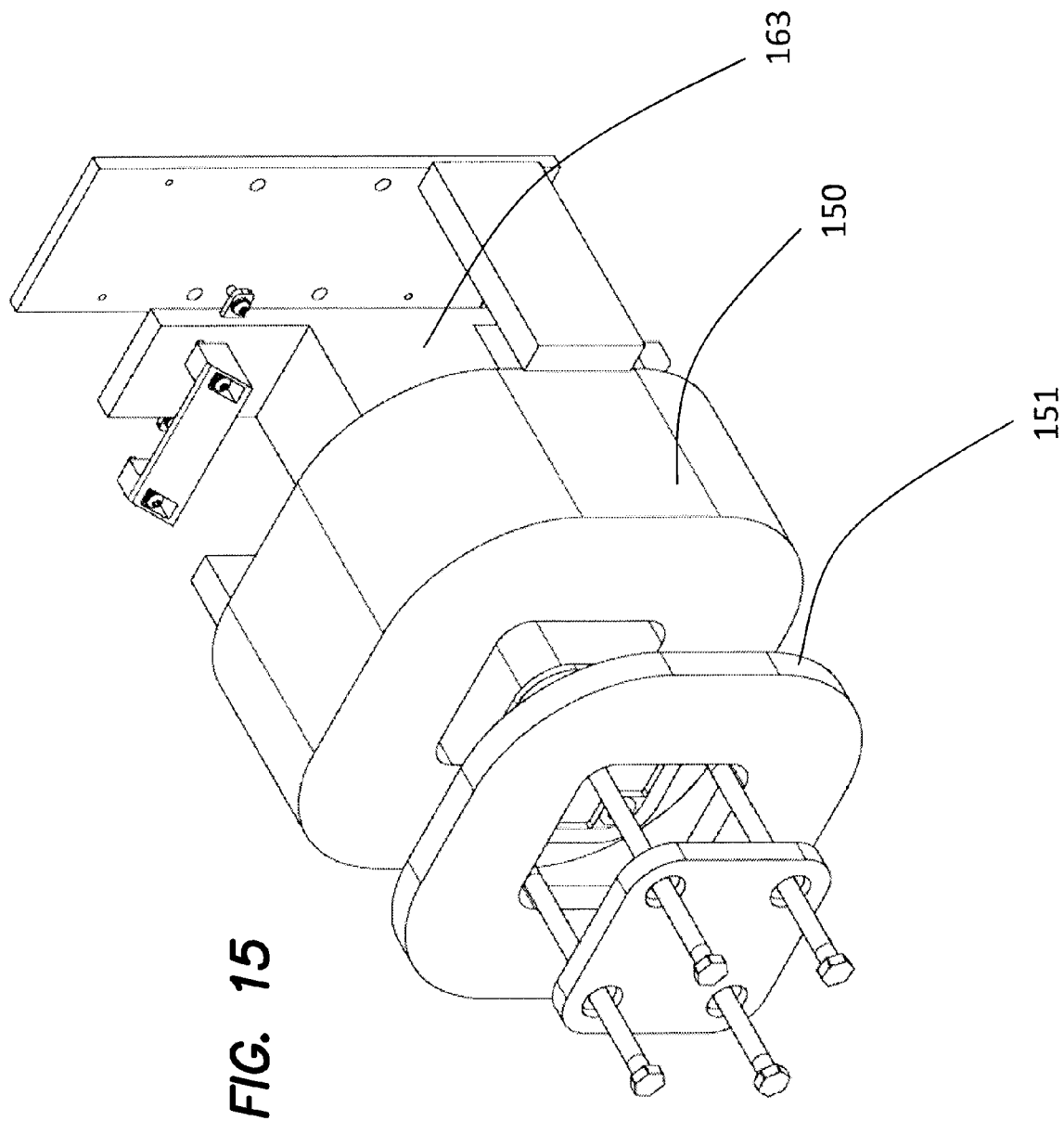
FIG. 15 is an exploded perspective view of the coil assembly.

FIG. 15 is an exploded view of the coil assembly. There are three coil assemblies on each of the half sections. The DC 150 and AC 151 coils are both shown with their mounting mechanism. The core 163 is made out of laminate transformer steel.

Figure 16:
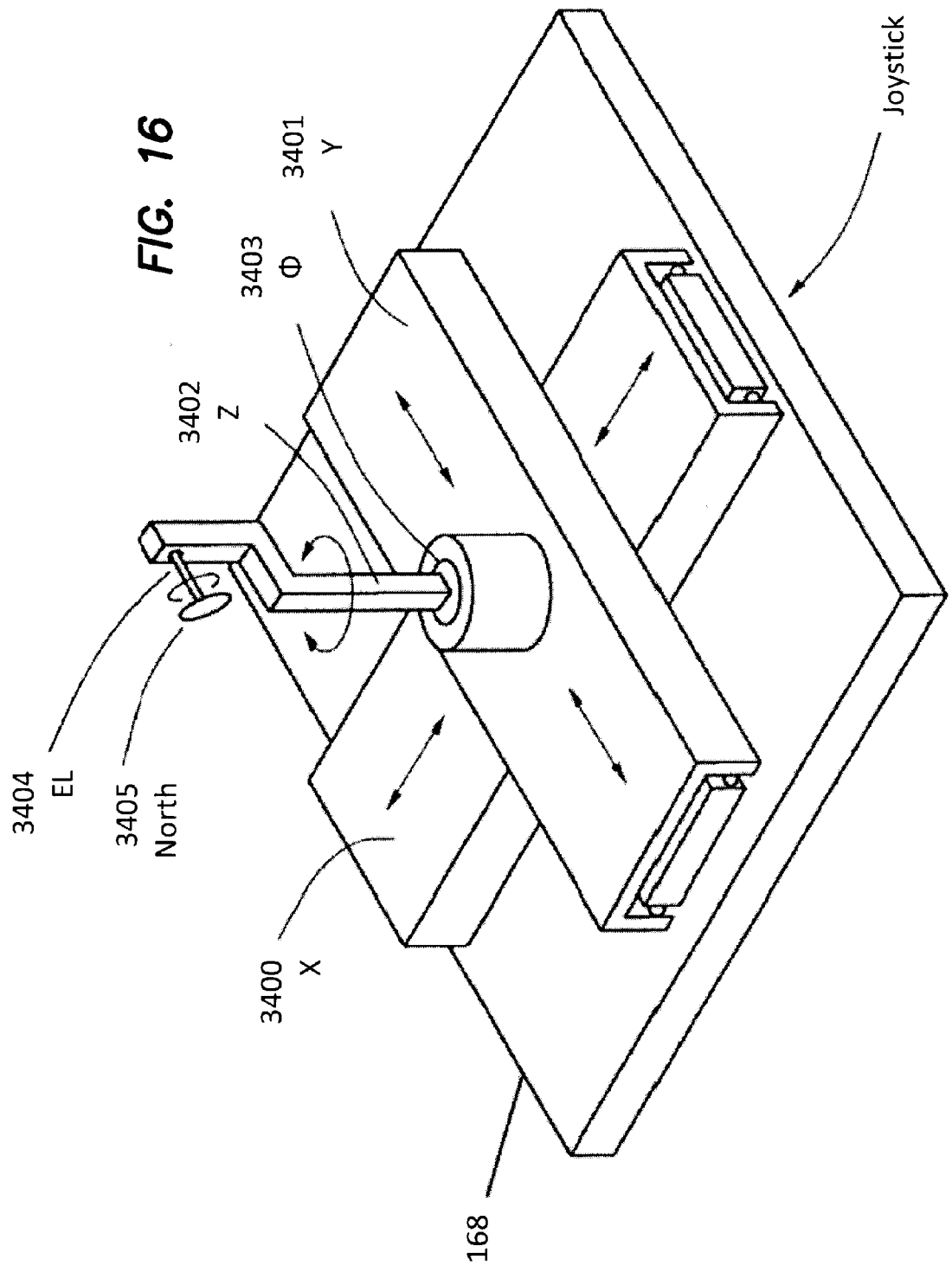
FIG. 16 is a perspective view showing one embodiment of the virtual capsule joystick.

FIG. 16 is a perspective view showing one embodiment of the virtual capsule user input device 168. The virtual capsule 168 is a multi-axis joystick-type device, which allows the surgeon to provide inputs to control the position, orientation, and rotation of the capsule 100, within the magnetic cavity. In one embodiment, the virtual capsule 168.1 includes an X input 3400, a Y input 3404, Z Input 3402, and a φ rotation input 3403 for controlling the position of the capsule 100. The virtual capsule 168.1 further includes a rotation 3405 and an elevation input 3404. As described above, the surgeon manipulates the joystick 168 and the virtual capsule 168.1 communicates the surgeon's movements to the computer stand 170 and its regulator for non-periodic field (DC) 173 and pulse-burst field regulator (AC) 172. The computer stand 170 then generates currents in the coils 150 (eight each) and 151 (eight each), to effect motion of actual capsule 100, to cause permanent magnet 101, 102, to follow the motions of the virtual capsule 168.1. In one embodiment, the virtual capsule 168.1, includes various motors and/or actuators (e.g., permanent-magnet motors/actuators, stepper motors, linear motors, piezoelectric motors, linear actuators, etc.) to provide force feedback 165, to the operator to provide tactile indications that the capsule 100, has encountered an obstruction of obstacle.

Figure 17:
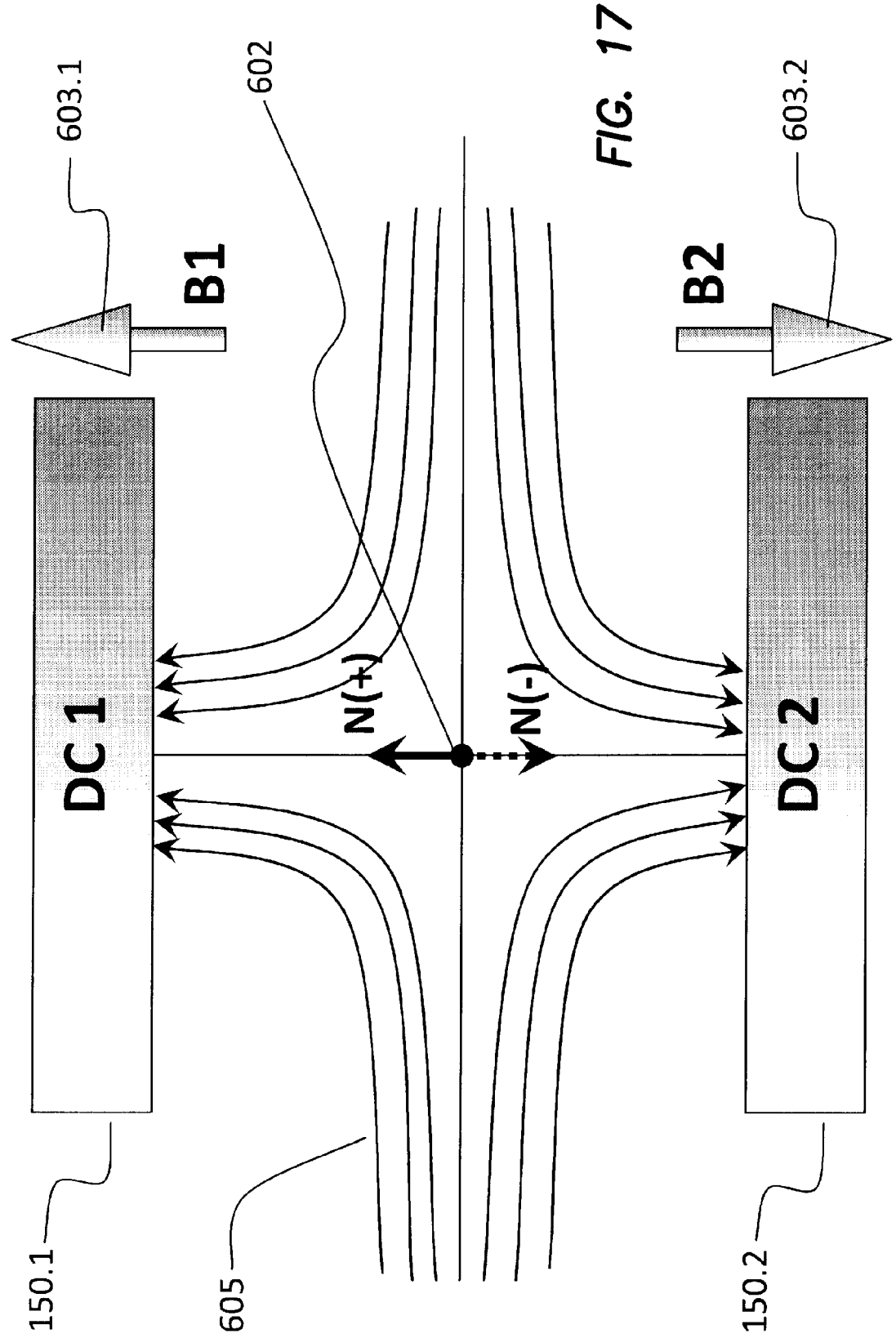
FIG. 17 is a diagrammatic illustration of the cross-section of a magnetic null generated by two opposing DC magnetic fields.

Consider now some magnetic static and dynamic principles. FIG. 17 is an illustration of the cross-section of a magnetic null generated by two opposing DC magnetic fields. DC magnetic coils DCI 150.1 and DC2 150.2 generate magnetic fields B1 603.1 and B2 603.2, respectively. The magnetic flux lines 605 diverge and form the magnetic null N 602. The magnetic null location and orientation is a function of B1 and B2. For our convention, the positive direction of the magnetic null will be in the same hemisphere as the desired capsule location. For our capsule, the null will always be below the capsule location, give an opposing gradient to the gravitational pull.

Figure 18:
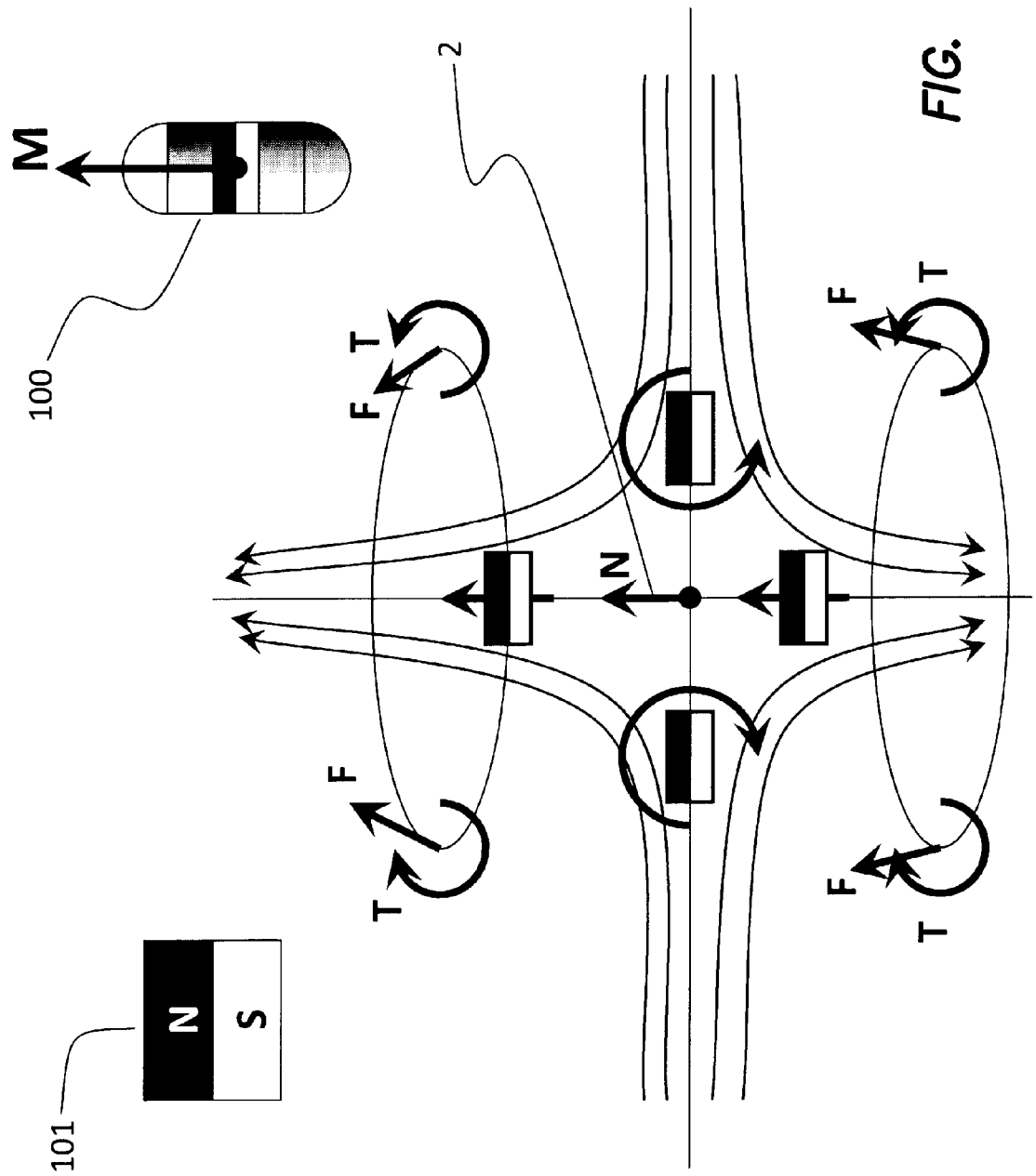
FIG. 18 is a diagrammatic illustration of the torques and forces created in a magnetic dipole dependent upon its position with respect to a positive magnetic null.

FIG. 18 is an illustration of the torques and forces created in a magnetic dipole dependent upon its position with respect to a positive magnetic null. The capsule 100 has an embedded magnetic dipole 101 which is oriented with the magnetic null 602. When the capsule location is in front of the magnetic null, the positive magnetic gradient pulls it in the direction of the coil. When the capsule is behind the magnetic null, the opposing coil's field gradient repels the dipole in the direction of the magnetic null. When the capsule is at the magnetic null but angularly inclined with respect to the null N 2, a torque is induced in the dipole that rotates it toward the direction of the magnetic null. Elsewhere, the dipole experiences a combination of torque and force.

Figure 19:
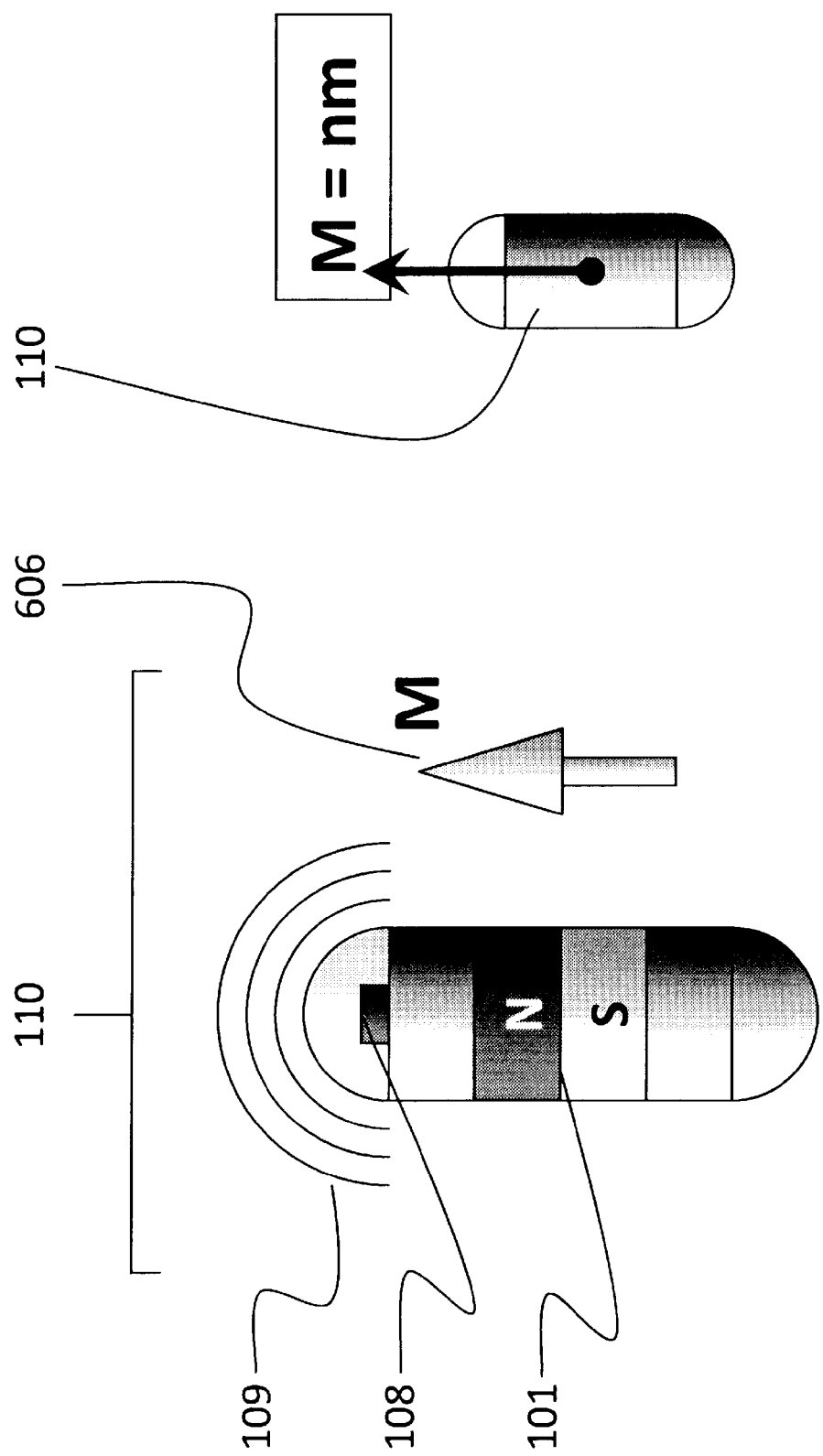
FIG. 19 is a diagrammatic illustration of the magnetic components of the capsule.

FIG. 19 is an illustration of the major components of the capsule 100. The camera lens 108 is provided illumination by light emitting diodes109. The magnetic dipole 101 has a total magnetization, M 606, in the direction of the camera lens. FIG. 19 further depicts a simplified graphical depiction of the magnetic moment M of capsule 100.

Figure 20:
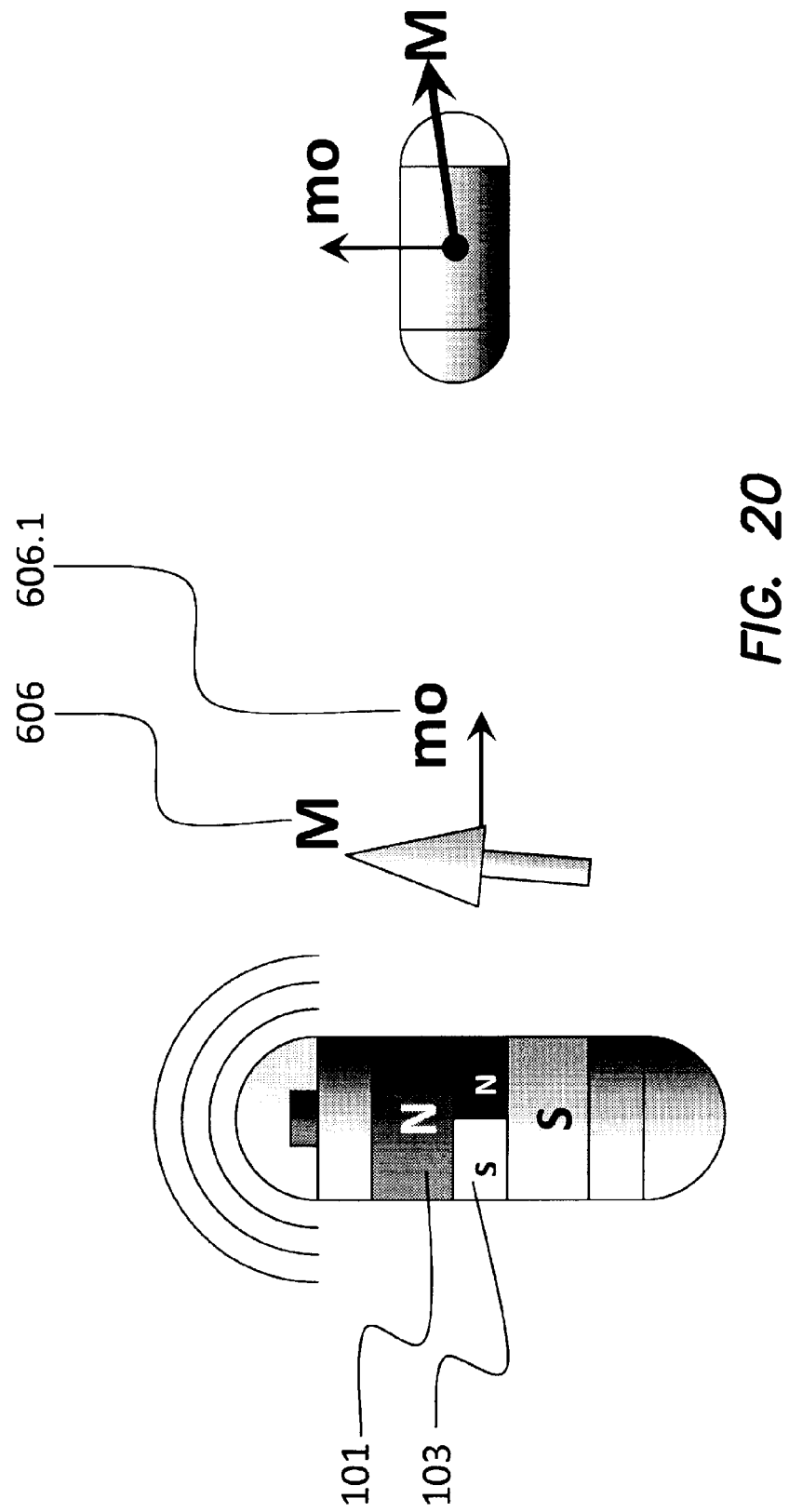
FIG. 20 is a diagrammatic illustration of an alternate embodiment of the capsule's magnetic configuration using a supplemental magnet to give axial rotation control and additional levitation.

FIG. 20 is an illustration of an alternate embodiment of the capsule's magnetic configuration using a supplemental magnet to give axial rotation control and additional levitation. The magnetic dipole 101 contains a secondary perpendicular dipole 103. This creates a secondary alignment vector, mo 606.1, which allows for orientation control and additional levitation forces when the capsule is near a horizontal orientation.

Figure 21:
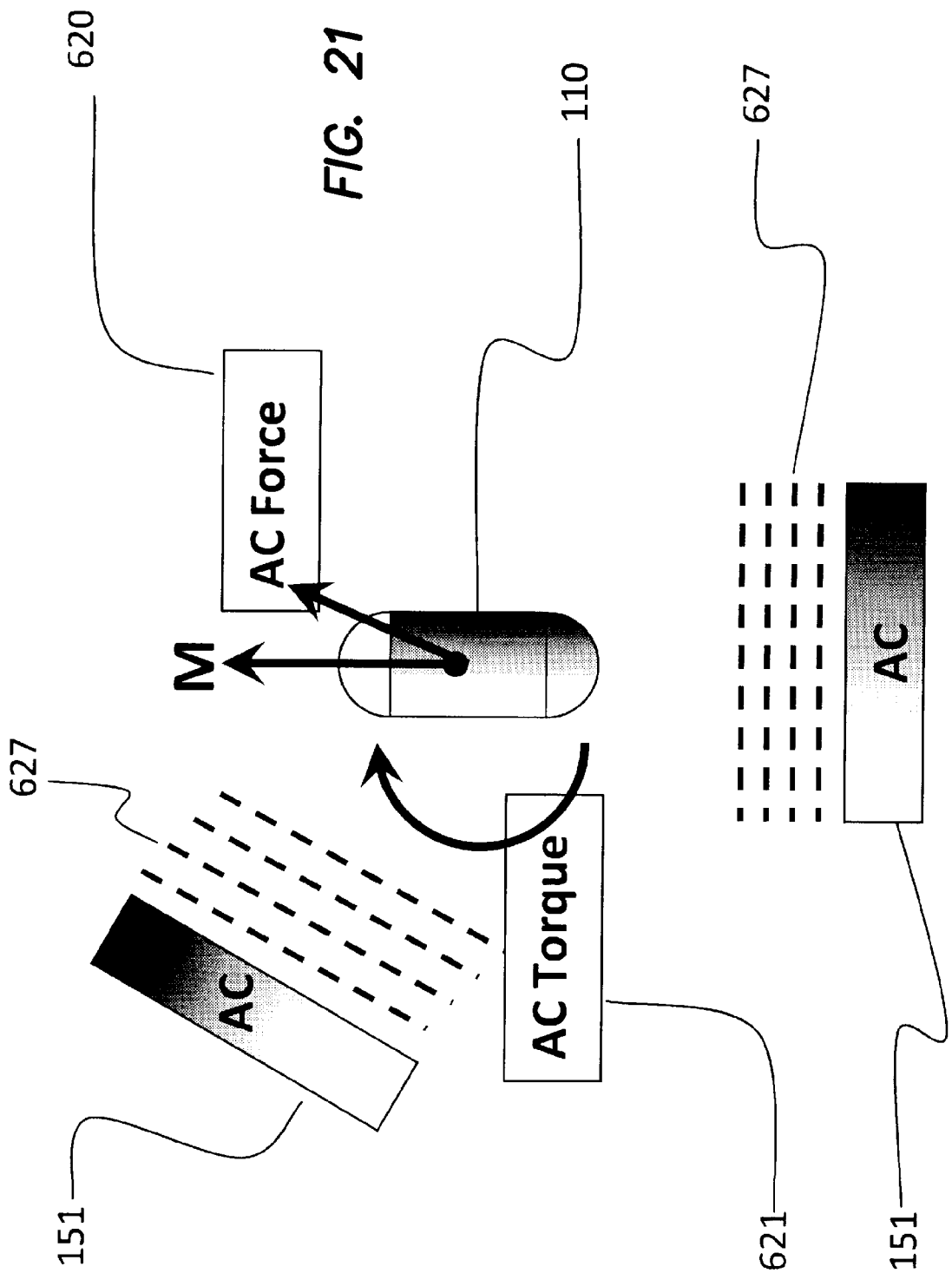
FIG. 21 is a diagrammatic illustration of the AC magnetic field repulsive forces and resultant torque on a capsule.

FIG. 21 is an illustration of the AC magnetic field repulsive forces and resultant torque on a capsule 100. The capsule 100 is subject to AC magnetic fields 627 from the AC magnetic coils 151. The net resultant AC force 620 is the sum of the forces from each AC field. The AC magnetic fields also induce an AC torque 621 in the capsule, which must be accounted for in the position control scheme.

Figure 22:
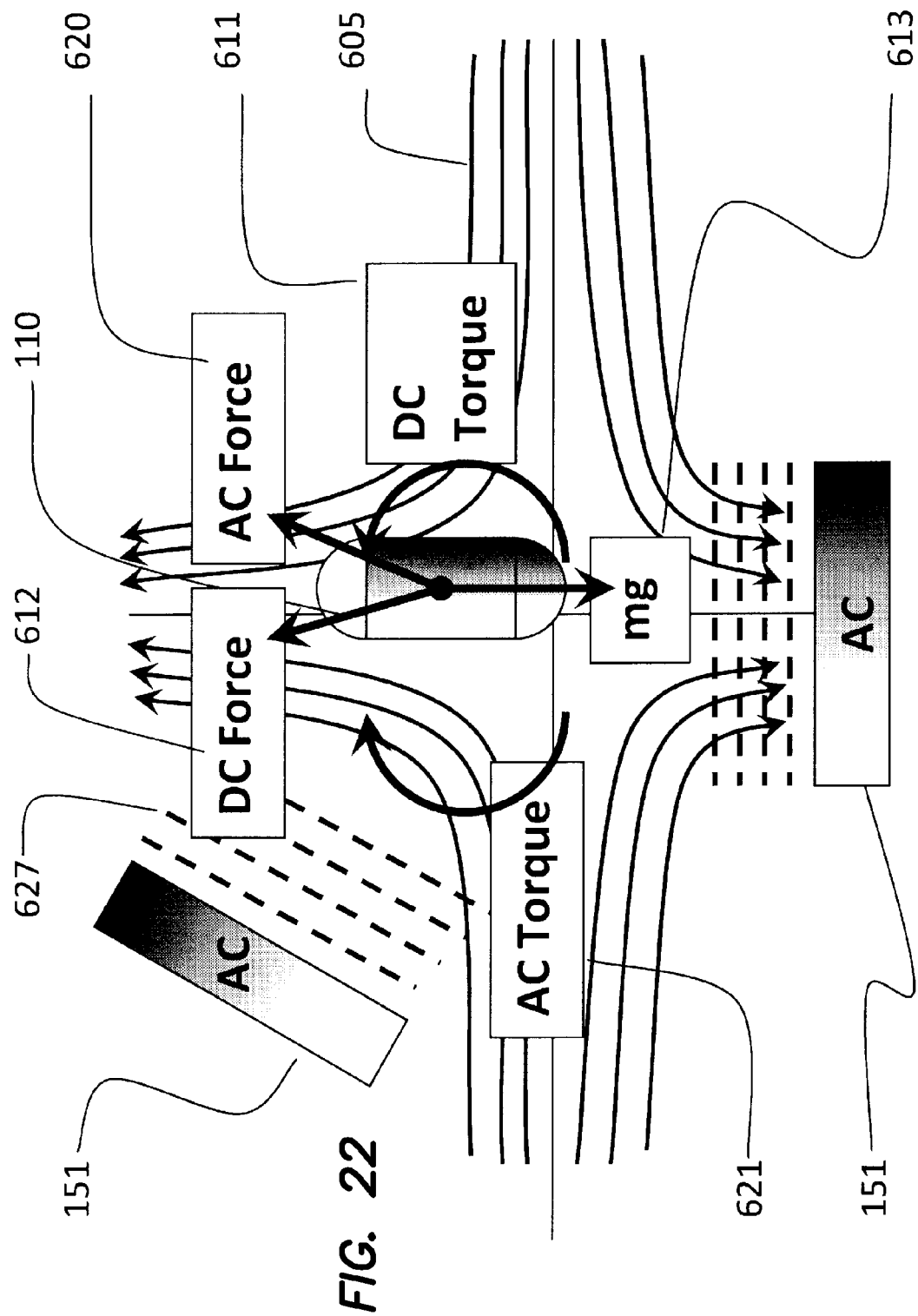
FIG. 22 is a diagrammatic illustration of the torques and forces acting upon a capsule in an AC/DC closed-loop control scheme.

FIG. 22 is an illustration of the torques and forces acting upon a capsule in an AC/DC closed-loop control scheme. To maintain position within a magnetic null, the closed-loop control system must maintain a balance between the torques and forces. To move the capsule 100, the closed-loop control system must generate, or allow a net torque or force to exist. The DC magnetic field 605 is generated as to place the magnetic null at the desired capsule position. The direction of the DC magnetic field null specifies the desired orientation of the capsule. The position of the capsule in the DC magnetic field generates a net DC force 612 and DC torque 611. The force of gravity adds a downward force, mg 613. The AC coils 151 are used in combination with each other to add a repulsive AC force 620 and net AC torque 621 to generate the desired net force and torque on the capsule 100.

Figure 23:
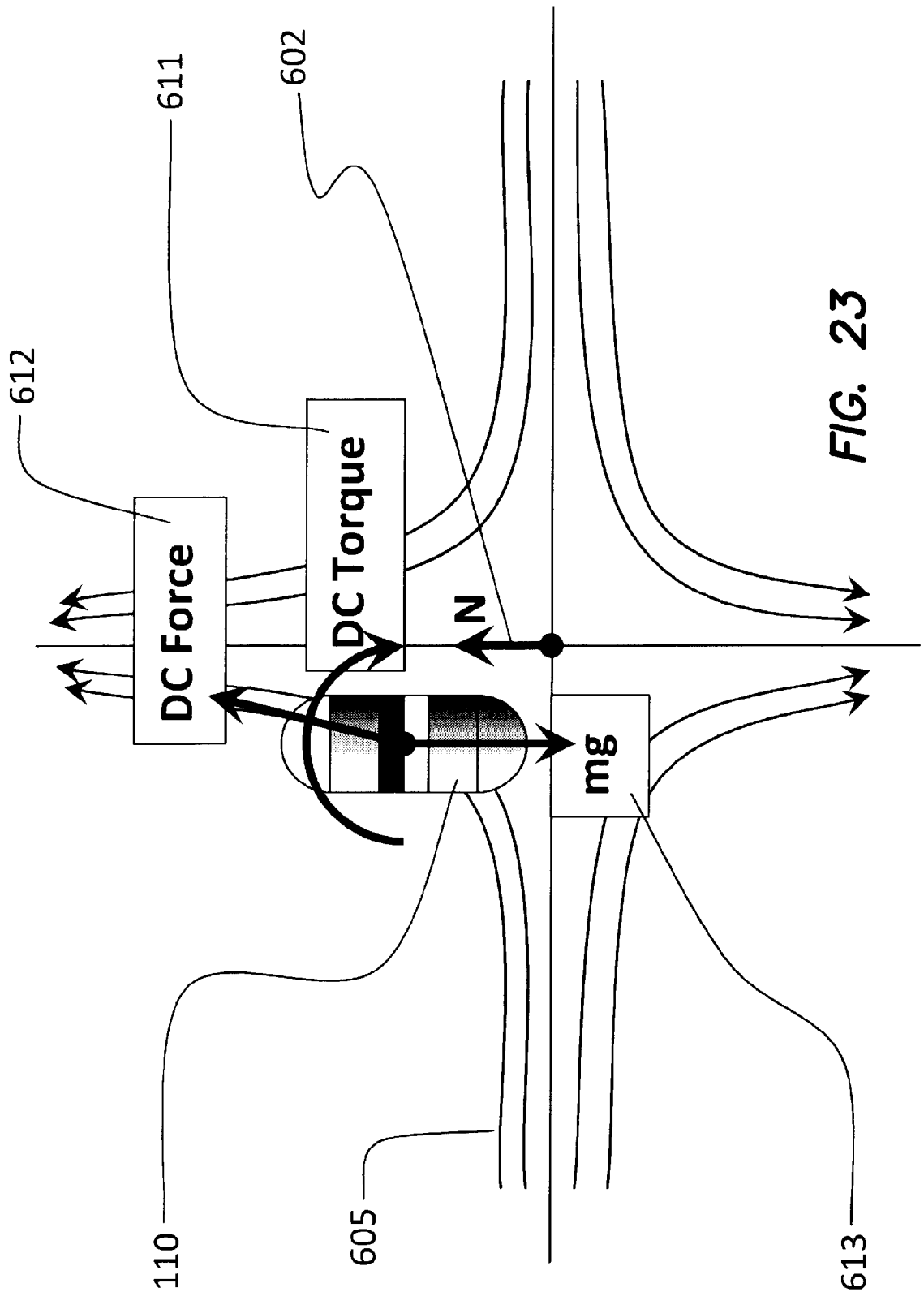
FIG. 23 is a diagrammatic illustration of the forces and torques on a capsule held vertically in a pure DC magnetic field control scheme.

FIG. 23 is an illustration of the forces and torques on a capsule held vertically in a pure DC magnetic field control scheme. The direction of the magnetic null 602 still specifies the desired orientation of the capsule 100, but the location of the null is shifted as to vary the force and torque placed on the capsule which allows for the control of both its position and orientation. The force of gravity, mg 613, is balanced by the DC force 612 component acting in the vertical direction. The net DC force 605 acting in the horizontal direction is used to adjust the capsule horizontal position. The DC torque 611 adjusts the capsule orientation with respect to the magnetic field, which also alters the forces acting upon its dipole.

Figure 24:
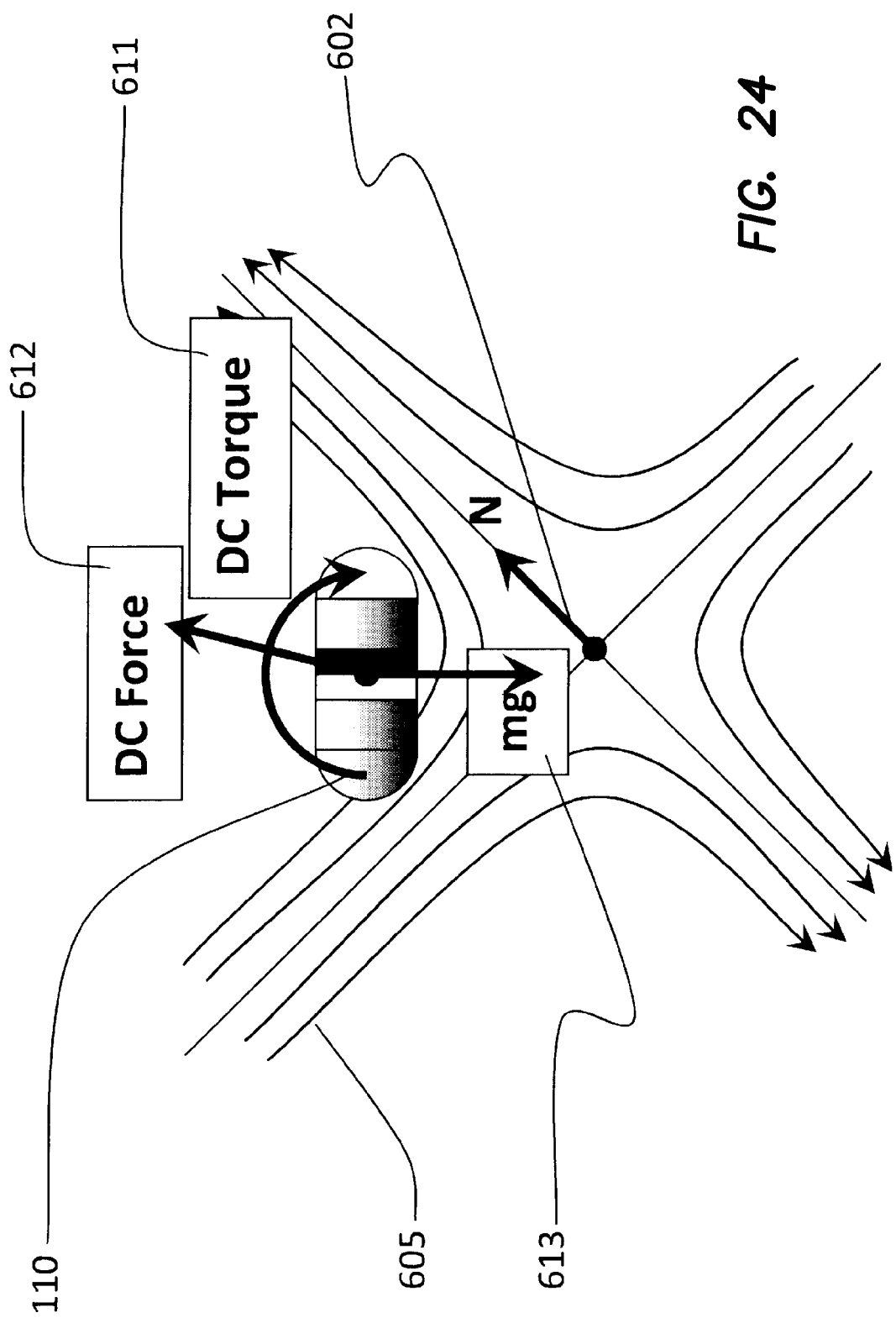
FIG. 24 is a diagrammatic illustration of the magnetic control torques and force used to control a capsule in the horizontal orientation using a pure DC magnetic control scheme.

FIG. 24 is an illustration of the magnetic control torques and force used to control a capsule in the horizontal orientation using a pure DC magnetic control scheme. A 90-degree rotation of the capsule 100 is controlled in reference to a 45-degree rotation of the magnetic null 602. The DC magnetic field 605 generates a gradient above the null that exerts a vertical DC Force 612 on the horizontal dipole to counteract the force of gravity, mg 613. The location of the magnetic null 602 is shifted to give net imbalances in the DC force 612 and DC torque 611 as to adjust the position and orientation of the capsule.

Figure 25:
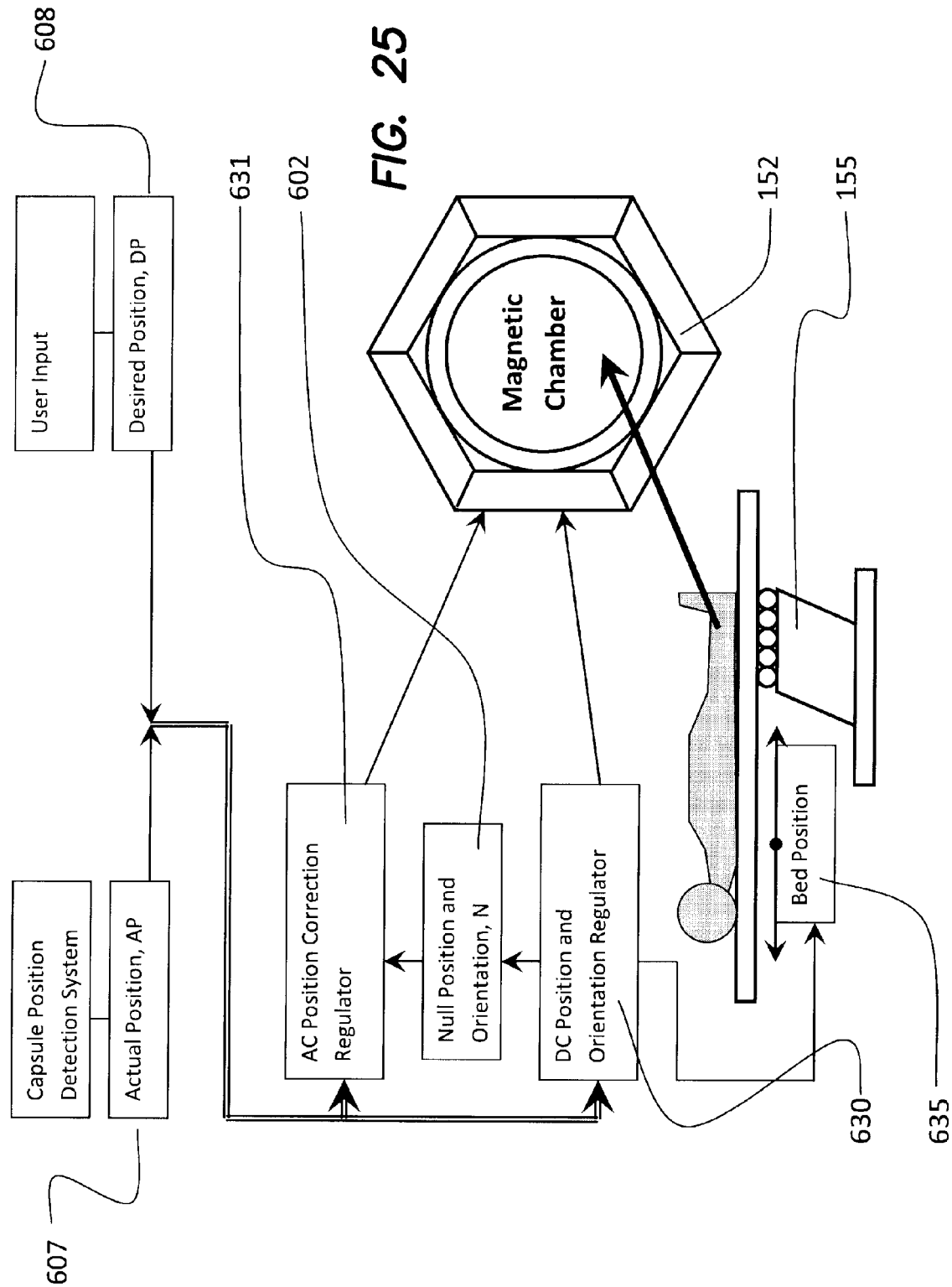
FIG. 25 is a block diagram of the major control components of the capsule position control system.

FIG. 25 is a block diagram of the major control components of the capsule position control system. User input specifies the desired position and orientation, DP 608, of the capsule. The actual position and orientation of the capsule, AP 607, is determined by the capsule position detection system. The DC position and orientation regulator controls the currents to the DC coils within the magnetic chamber 152. The bed 155 is within the magnetic chamber 152, and the bed position 635 within the magnetic chamber is controlled by the DC position and orientation regulator 630. The AC coils are controlled by the AC position correction regulator 631, which uses the position of the magnetic null, N 602, and the actual position of the capsule, AP 607, to determine whether AC force is necessary to correct the capsule position.

Figure 26:
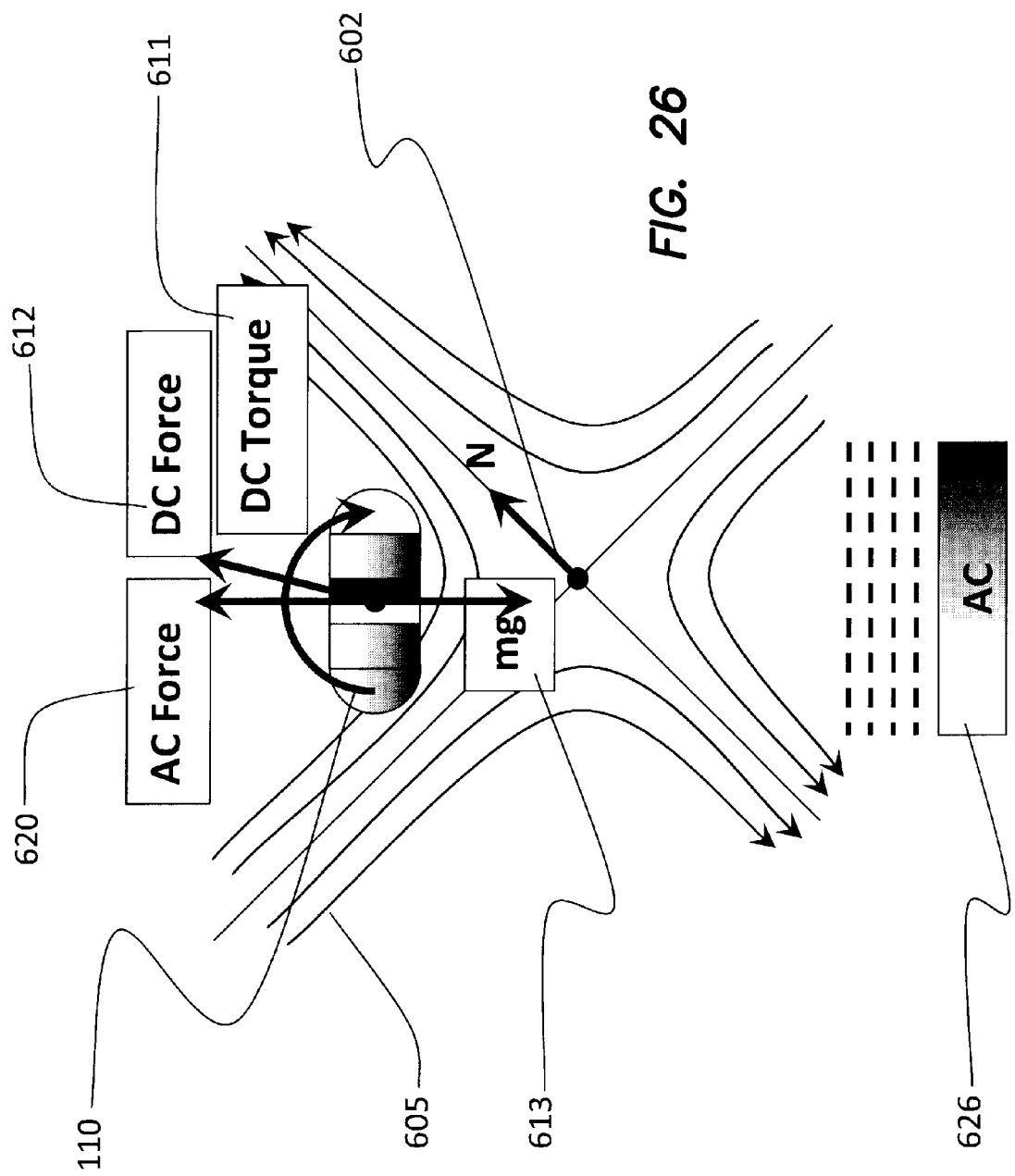
FIG. 26 is a diagrammatic illustration of the DC-dominant regulator scheme.

FIG. 26 is an illustration of the DC-dominant regulator scheme. In this position and orientation regulation scheme, the DC magnetic field 605 is used as the primary method of controlling the capsule 100 position and orientation. The AC coils 626 are only activated when the DC field is unable to keep the capsule 100 within the maximum range from the magnetic null 602. The force of gravity, mg 613, and other external forces create imbalances that cannot be overcome by corrections to the DC force 612 and DC torque 611.

Figure 27:
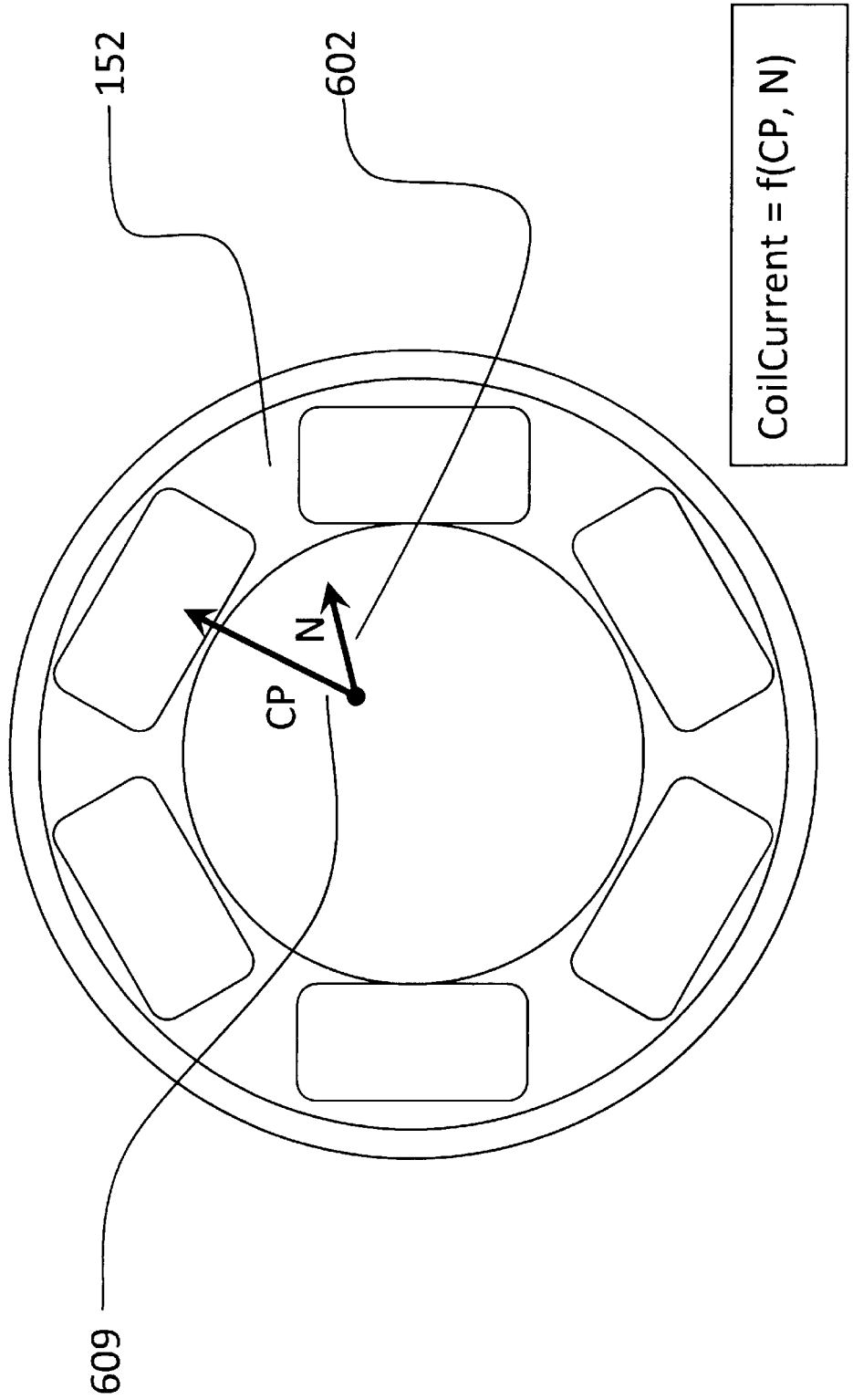
FIG. 27 is a diagrammatic illustration of the vectors used to calculate coil currents.

FIG. 27 is an illustration of the vectors used to calculate coil currents. The coil position vector, CP 609, is defined as the distance and direction from the magnetic null position and orientation vector 602 to the center of the coil's influence, which is just inside the inner surface of the coil's core. The coil current for each coil in the magnetic chamber 152 is calculated as a function of the distance and orientation of the coil's CP vector with respect to the magnetic null, N 602.

Figure 28:
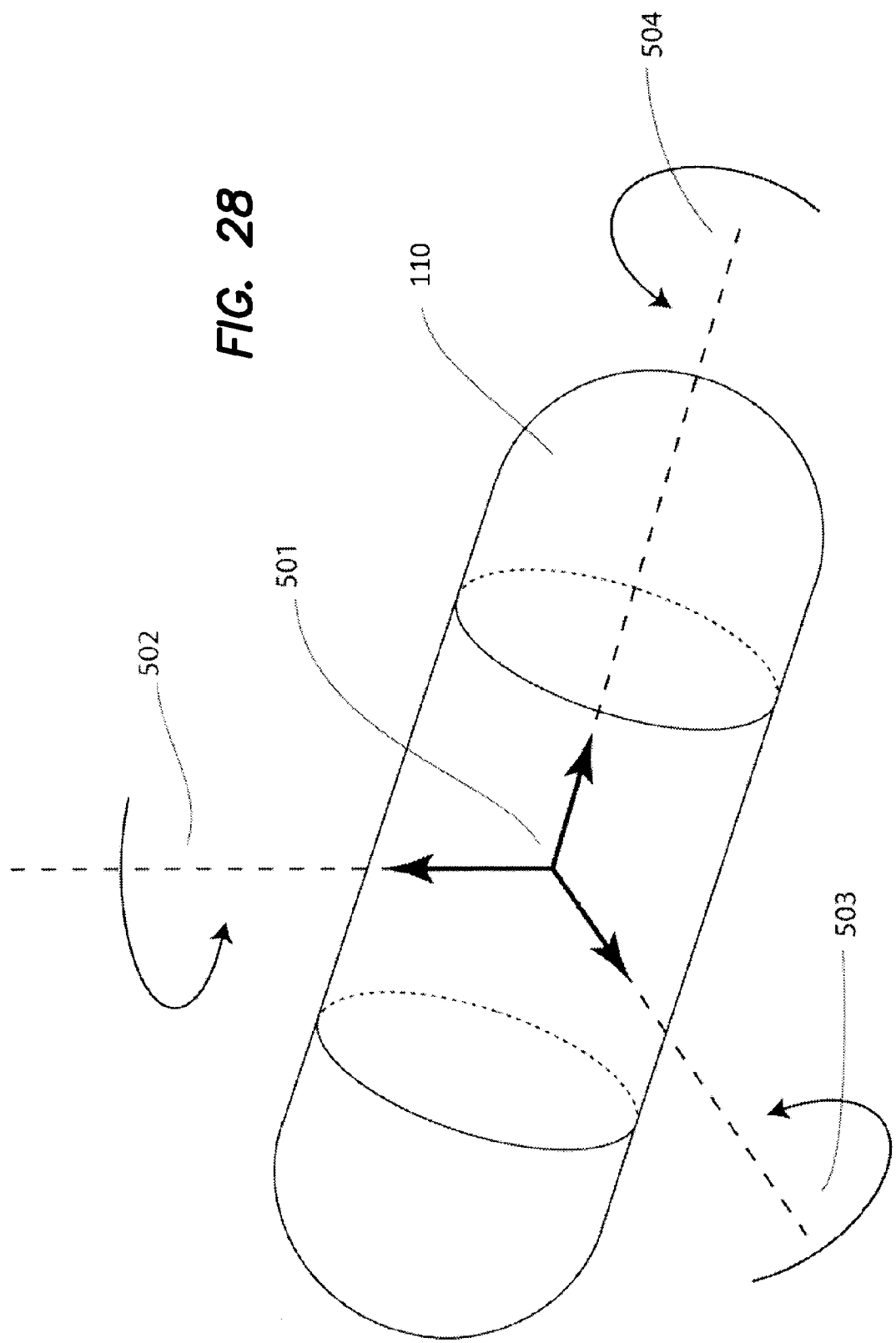
FIG. 28 is a diagrammatic illustration of the capsule coordinate system.

FIG. 28 is an illustration of the capsule coordinate system. The capsule 100 has a sensor coordinate system 501 that is specified by yaw 502, pitch 503 and roll 504.

Figure 29:
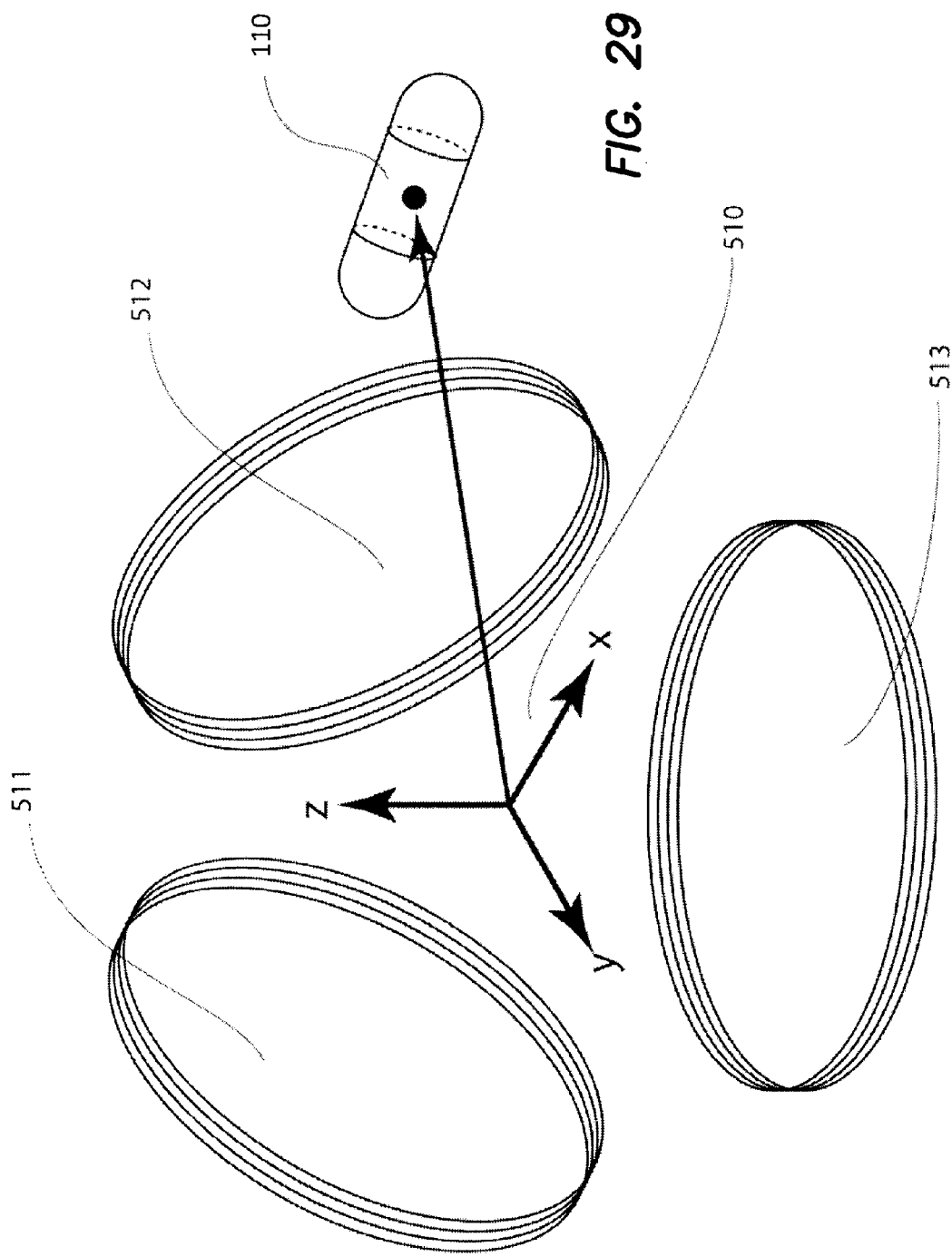
FIG. 29 is a diagrammatic illustration of the external sensor coils relative to the capsule.

FIG. 29 is an illustration of the external sensor coils relative to the capsule. The capsule 100 is detected with respect to the three external coils 511, 512, and 513 and their coordinate reference system 510.

Figure 30:
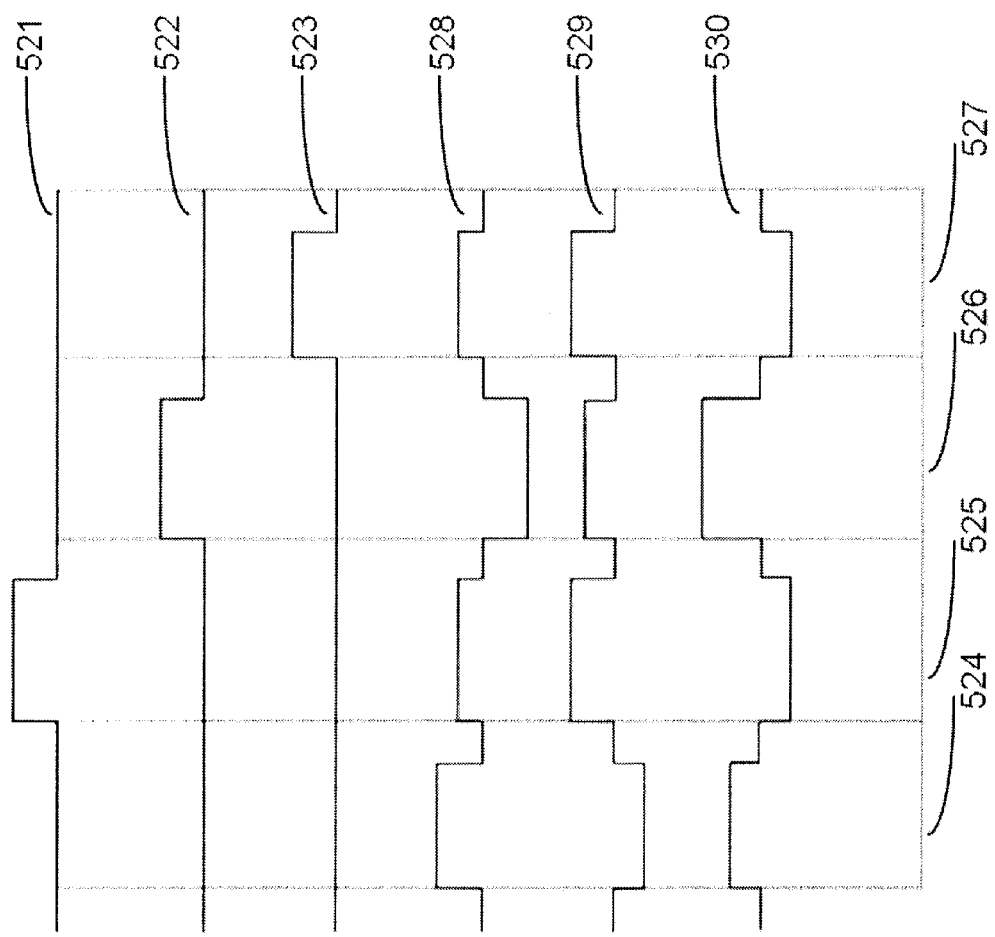
FIG. 30 is a signal timing diagram of the capsule position detection system.

FIG. 30 is a signal timing diagram of the capsule position detection system. The position vector $[p_x, p_y, p_z]$, 514 relative to a reference point and the orientation vector [Yaw($\Psi$), Pitch ($\phi$), Roll($\theta$)] are detected using a 6-axis geomagnetic sensor, which has 3-axis acceleration and 3-axis magnetic field sensors.

Orientation Vector

The 3-axis accelerometer or gravity detector provides an acceleration vector $\vec{a} = [a_x, a_y, a_z]$, which includes to the motion acceleration of the sensor superimposed by the acceleration due to gravity. Assuming the sensor is at constant velocity, the acceleration vector obtained is due to the gravity with reference to the coordinate system on the sensor, 501. This acceleration due to gravity vector directly gives the pitch($\phi$), 503 and roll($\theta$), 504 of the orientation vector.

$$\phi = \tan^{-1}\left(\frac{-a_x}{\sqrt{a_z^2 + a_y^2}}\right) \quad [11]$$

$$\theta = \tan^{-1}\left(\frac{a_y}{a_z}\right) \quad [12]$$

By using an external coil as a magnetic marker, yaw($\Psi$), 502 can be calculated by combining both accelerometer and magnetometer readings.

$$\psi = \psi(m_x, m_y, m_z, \phi, \theta) = \tan^{-1}\left(\frac{-B_y}{B_z}\right) \quad [13]$$

$$B_y = m_x \cos\theta + m_y \sin\theta \sin\phi + m_z \sin\theta \cos\phi \quad [14]$$

$$B_z = m_y \cos\phi - m_z \sin\phi \quad [15]$$

Where $\vec{B} = [B_x, B_y, B_z]$ is the magnetic field vector of the external magnetic marker.

Position Vector

The 3-axis magnetic sensor provides the magnetic vector $\vec{m} = [m_x, m_y, m_z]$ relative to external coils. The goal is to obtain three dimensional position $[p_x, p_y, p_z]$ vector, 514 of the sensor relative to the 3 external coils 511, 512, 513 in reference coordinate system 510. The external coils generate magnetic field $[B_x, B_y, B_z]$ of known strength by using this set of equations.

$$\vec{B}_m = \frac{\mu_0}{4\pi}\left(\frac{3(\vec{m}\cdot\vec{p})\vec{p}}{p^5} - \frac{\vec{m}}{p^3}\right) \quad [16]$$

$$\begin{bmatrix} B_x + B_{x(ambient)} \\ B_y + B_{y(ambient)} \\ B_z + B_{z(ambient)} \end{bmatrix} = \frac{\mu_0}{4\pi}\left(\frac{3(m_x p_x + m_y p_y + m_z p_z)}{p^5}\begin{bmatrix} p_x \\ p_y \\ p_z \end{bmatrix} - \frac{1}{r^3}\begin{bmatrix} m_x \\ m_y \\ m_z \end{bmatrix}\right) \quad [17]$$

Given $\vec{B}$, $\vec{B}_{(ambient)}$, and the measured magnetic moment $\vec{m}$, the position vector $\vec{p}$ can be solved by using a nonlinear optimization method (for example, the one described in Powell 1964)

Since the value of m given by the sensor is not relative to the external coils, a magnetic localization technique is used to solve this equation [Blood et al. 1989]. This localization technique requires the external coils to generate 4 pulses of known magnetic field strength as shown in FIG. 30. In one of the pulses, 524, the reference magnetic fields are off which is used to calibrate against the ambient magnetic field such as Earth's magnetic field. The other three pulses 525, 526, 527 are against each axis of the external field. The amplitudes of the external fields are assumed to be in the same order of magnitude as the Earth's magnetic field (~0.5 gauss). The pulse width can be as small as the sensor response (~1 ms). The signals 528, 529, 530 shown in FIG. 30 are the three components $[m_x, m_y, m_z]$ of the sensor output $\vec{m}$ during these external magnetic field excitation sequences and are used to solve Equation 17.

Figure 31:
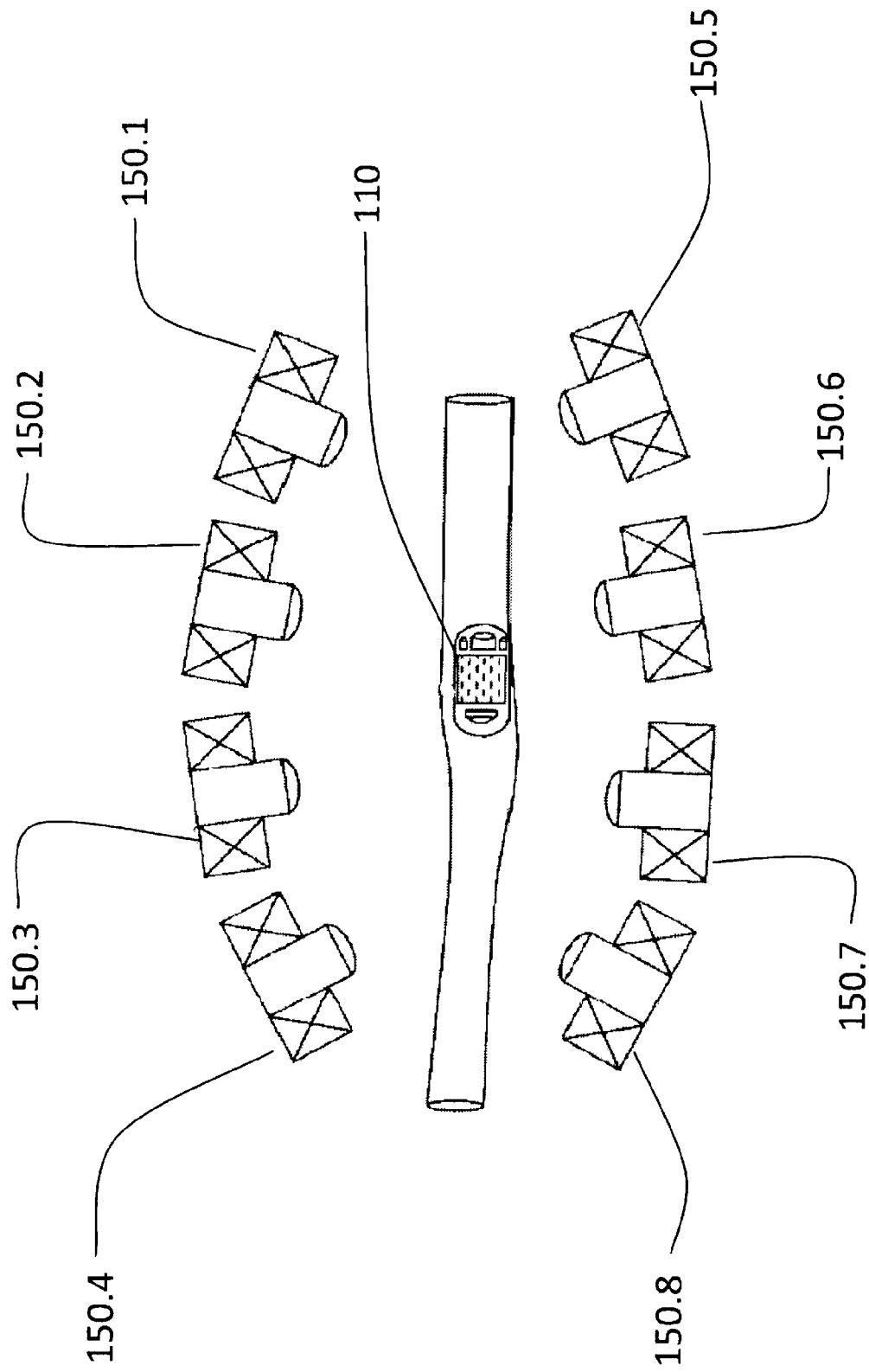
FIG. 31 is a schematic diagram of how the magnetic fields of the MFG cooperate to overcome or negate the peristalsis effect as the capsule is guided through the patient.

FIG. 31 is a schematic diagram of how the magnetic fields of the MFG cooperate to overcome or negate the peristalsis effect as the capsule is guided through the patient. The DC Coils 150.1-150.8 are cooperatively controlled to pull or push the capsule 100 through the body lumen.

Figure 32:
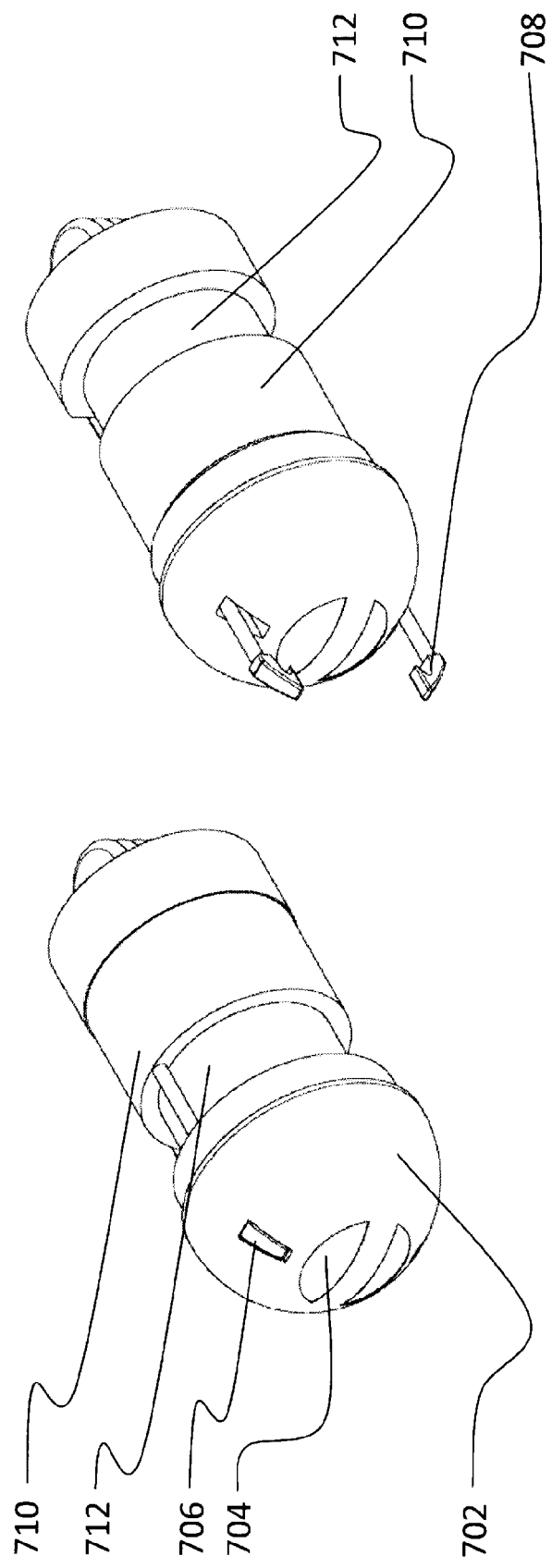
FIG. 32 is a perspective illustration of the capsule major components comprising the biopsy needle embodiment shown on the left portion of the figure in an extended configuration and on the right portion of the figure in an retracted configuration.

FIG. 32 is an illustration of the major components comprising the biopsy needle embodiment. In yet another embodiment, the capsule 100 may be used for tissue sample collection within the GI tract of the patient. One of the domes 702 comprises a contact sensor 704 and a pair of apertures 706 defined within the dome 702. Disposed within the apertures 706 is a pair biopsy needles 708. The biopsy needles 708 are shaped such that when they are in a retracted position, their outer surfaces conform to the curvature of the dome 702 to provide a smooth, continuous surface to the capsule 100. The opposing ends of the biopsy needles 708 are coupled to a coil ring 710 disposed about a core 712. The coil ring 710 is a solid ring comprised of a plurality of turns or loops of wire. The core 712 is a permanent magnet, preferably comprised of NdFeB, however other highly magnetized materials may be used within the spirit and scope of the invention. The coil ring 710 and core 712 together form a solenoid as is well known in the art.

When the capsule 100 is guided towards a tumor or other biological target by the means described above, the dome 702 comprising the contact sensor 704 and biopsy needles 708 is orientated towards the tumor. The capsule 100 is continually brought towards the surface of the tumor by the MFG until contact is achieved as determined by the contact sensor 704 by means known in the art. An additional magnetic flux is then sent by the MFG 425, causing a corresponding flux within the magnetic core 712 of the capsule 100. In response to the change in flux within the magnetic core 712, the coil ring 710 is pushed distally through the capsule 100 by the actuating solenoid which in turn pushes the biopsy needles 708 out of the dome 702 and into the tumor. The biopsy needles 708 extend into the tumor until the coil ring 710 reaches the distal end of the capsule 100. After a predetermined time, the MFG 425 stops sending its additional magnetic flux, returning the configuration of surrounding magnetic fields to their original orientation and strength before the capsule 100 was activated. This change in external flux brings the coil ring 710 back in the proximal direction about the magnetic core 712. The biopsy needles 708 coupled to the coil ring 710 in turn are also brought back proximally into the dome 702 of the capsule 100. Due to the substantially hooked shape of the needles 708, a sample of the tumor is also brought back into the dome 702 through each of the respective apertures 706. Each of the apertures 706 are large enough to accommodate both a sample of the tumor 714 and the biopsy needle 708 such that the distal portion of the biopsy needle 708 is once again flush with the surface of the dome 702 once the coil ring 710 is fully retracted within the capsule 100 to its original starting position:

With the capsule 100 now containing a sample of the tumor or other biotarget, the capsule 100 may be left to continue its path through the patient's GI tract naturally. When the patient passes the capsule 100, it may be opened by the patient's physician and the sample of the tumor removed. Traditional biopsy techniques as are well known in the art may then be performed on the sample tissue, thus giving the physician and patient invaluable and timely diagnostic information on the metabolic or physiological state of the tumor.

Figure 33:
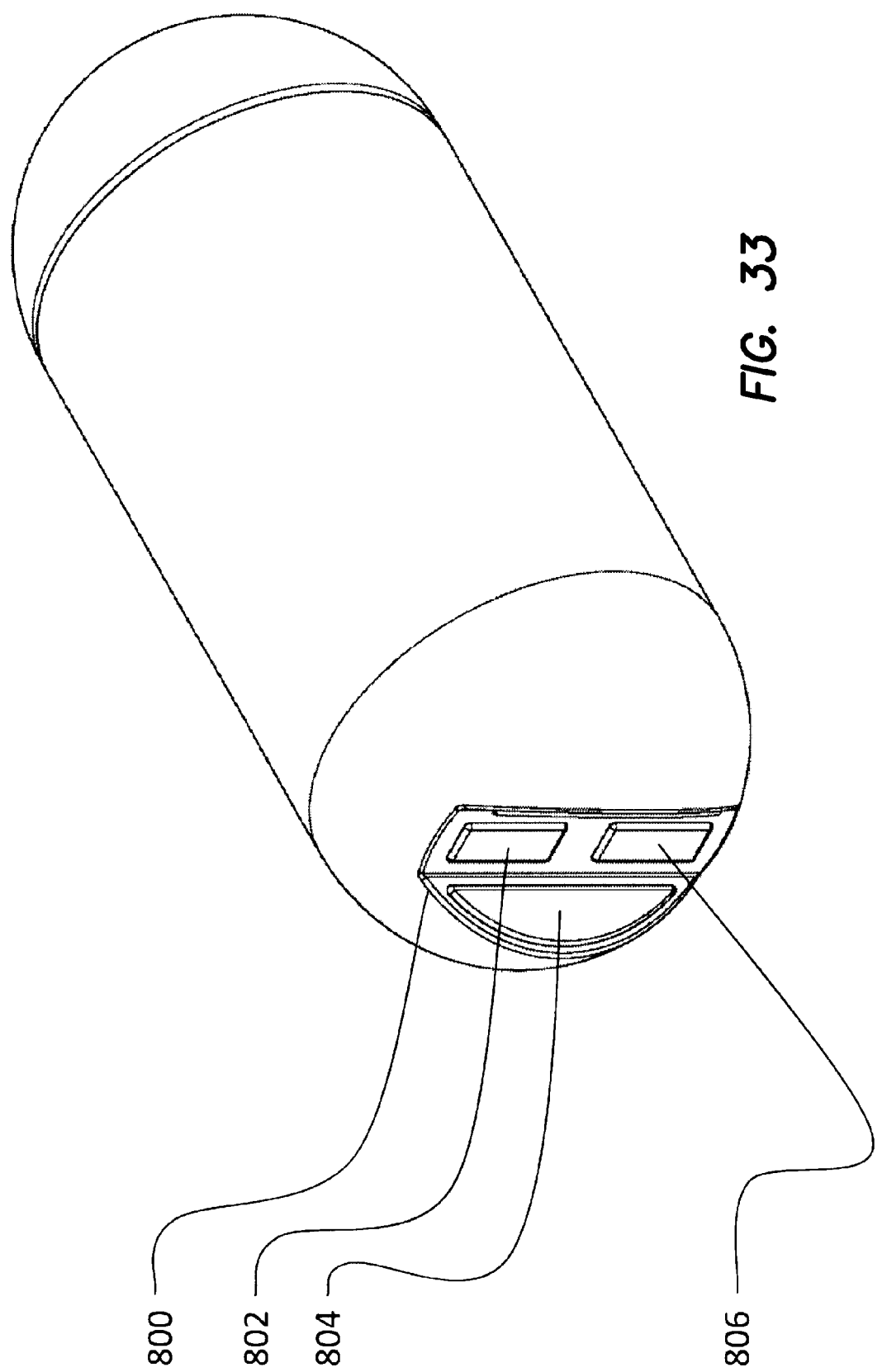
FIG. 33 is a perspective illustration of the major components comprising the PH sensor and multi-spectrum UV analyzer embodiment.

FIG. 33 is an illustration of the major components comprising the PH sensor and multi-spectrum UV analyzer embodiment. In yet another embodiment, the capsule 100 comprises an enhanced spectrum analyzer. In addition to a camera disposed in one end of the capsule 100 as discussed above, the opposing end of the capsule 100 comprises a tissue cavity. The tissue cavity 800 is a substantially wedge shaped cavity defined into one of the domes, however other shapes which allow close tissue contact may also be used without departing from the original spirit and scope of the invention. The tissue cavity 800 itself comprises of suite of analysis components including but not limited to a multi-spectrum UV LED 802, a pH sensor and/or a contact sensor 804, and a multi-spectrum photo detector 806.

When the capsule 100 is guided towards a tumor or other biological target by the means described above, the dome comprising the tissue cavity 800 is orientated towards the tumor. The capsule 100 is continually brought towards the surface of the tumor by the MFG until contact is achieved as determined by the contact sensor 804 by means known in the art. Preferably the capsule 100 is orientated about the tumor or biological target so that at least a portion of the tumor or biological target is disposed within the tissue cavity 800 and in close proximity to the UV LED 802, pH sensor 804, and the photo detector 806. With the capsule 100 in the correct position or orientation with respect to the tumor, the operating physician at the control center may then activate the suite of electronics contained within the tissue cavity 800. For example, the UV LED 802 may transit a spectrum of light in the ultra violet range through the tumor which is then detected by the photo detector 806 as an absorption spectrum. Meanwhile the pH sensor 804 may be contemporaneously obtaining acidity measurements of the tumor by means currently known in the art. Both the pH level and absorption spectrum obtained by the pH sensor 804 and photo detector 806 respectively may then be recorded on a memory storage device, such as a ROM chip, internally disposed within the capsule 100. When the patient passes the capsule 100, it may be opened by the patient's physician and the data from contained on the memory storage device downloaded or otherwise extracted. Traditional data analysis techniques as are well known in the art may then be performed on the sample data, thus giving the physician and patient invaluable and timely diagnostic information on the metabolic or physiological state of the tumor.

Figure 34:
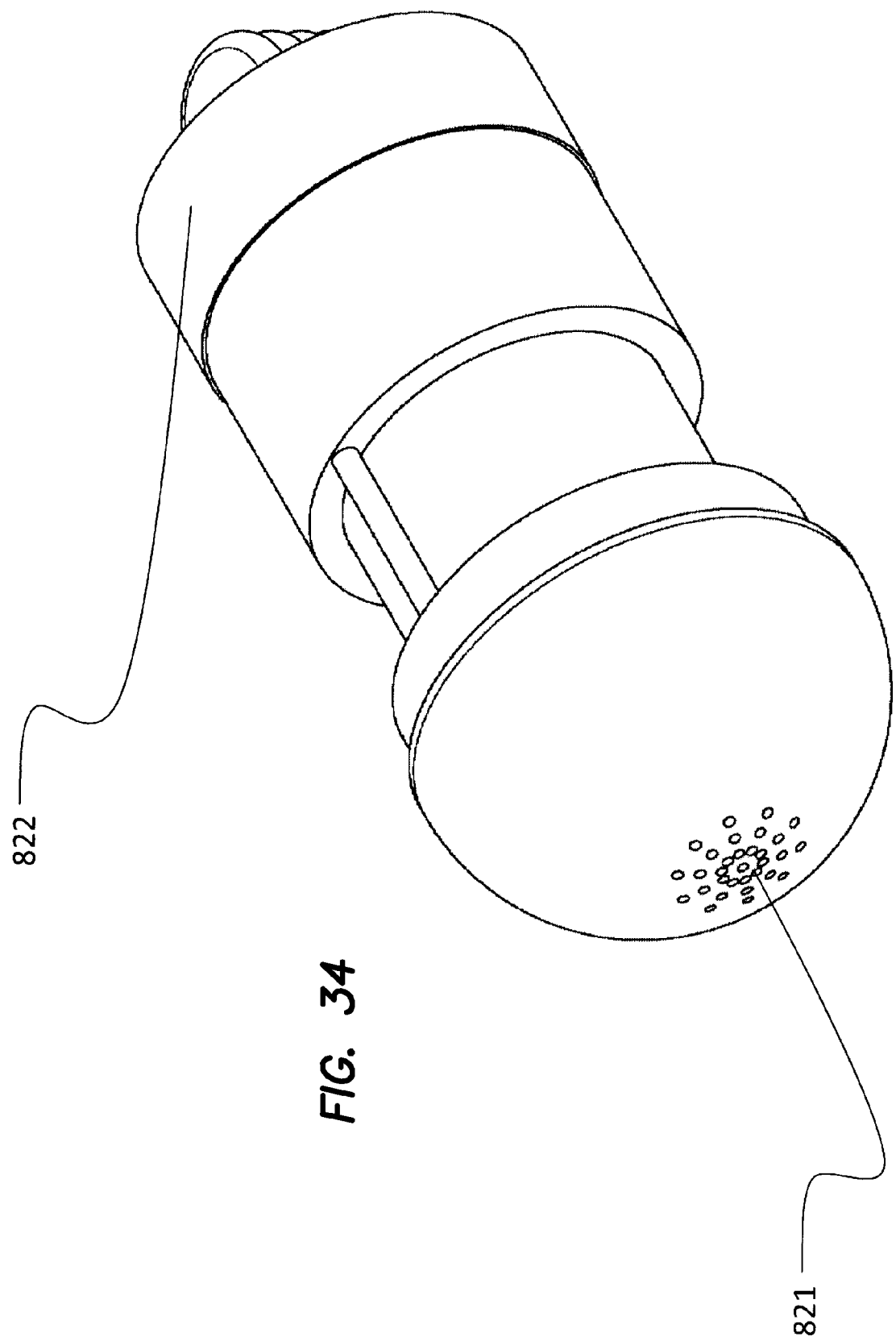
FIG. 34 is a perspective illustration of the major components comprising the injector/spray nozzle embodiment.

FIG. 34 is an illustration of the major components comprising the injector/spray nozzle embodiment. Fluid is transferred from the reservoir 822 and ejected through the dome nozzles 821.

FIG. 35 is an orthographic cross section of the apparatus forming the magnetic aperture 950, and its EM radiator comprising of a coil 911.$x$, a core 912.$x$ with material permeability value of 905.$x$, a pole face 904.$x$, with permeability value 905.$y$, and a pole face insert 904.3$x_y$, with permeability 905.$z$, where x, y and z represent dummy indices to denote various ones of the magnet positions.

The construction of the magnetic aperture 950, is the apparatus producing the geometry and orientation of the shaped magnetic field. The theory and principle of operation of the magnetic cavity 1000, with its EM radiators 917.1-917.8, is articulated articulated by the use of magnetic aperture with suitable geometry and material permeability so as to generate a magnetic flux density axis appropriate for translating, rotating and levitating an untethered medical device within a body cavity.

Figure 35A:
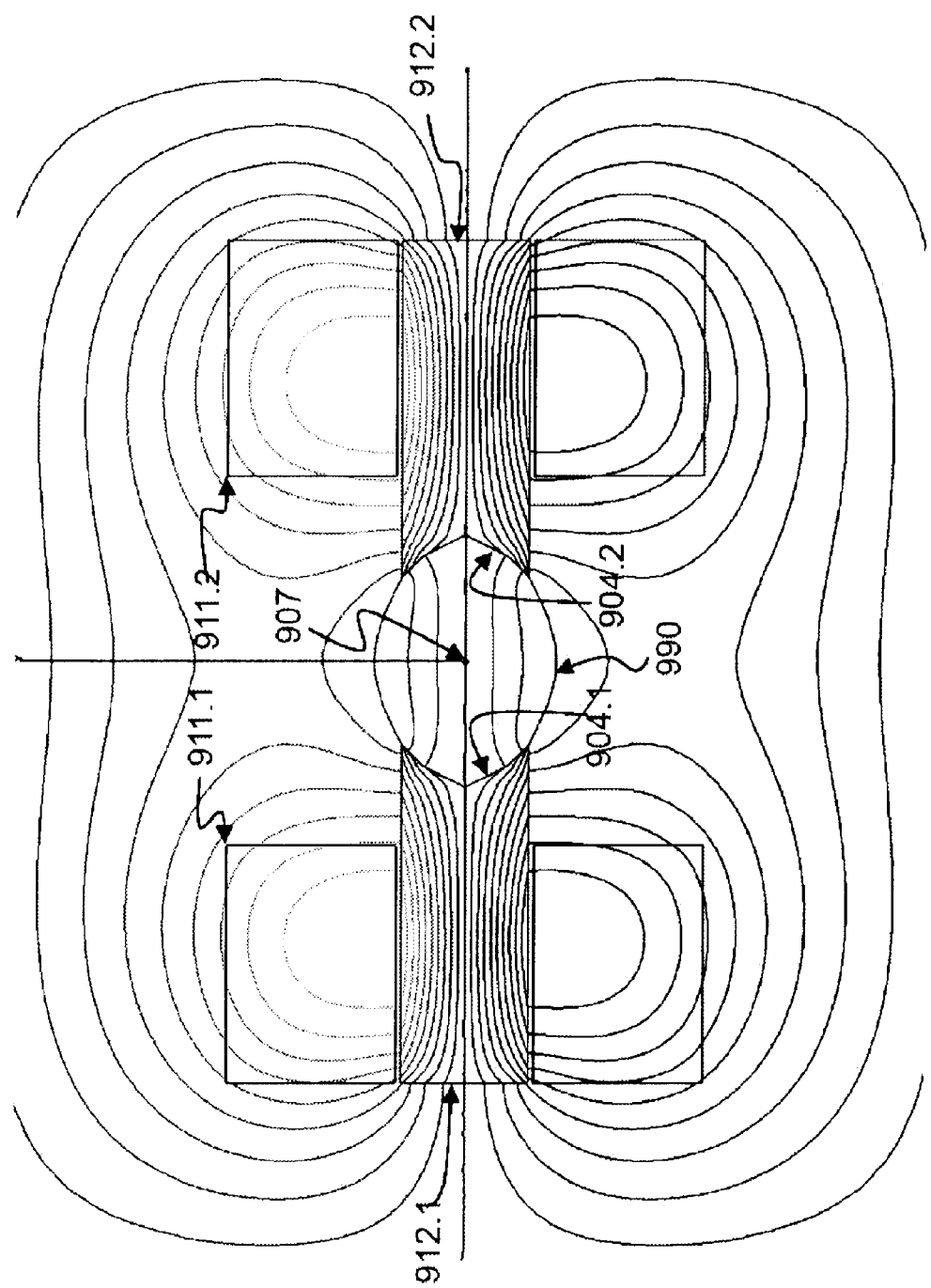
FIG. 35A is an orthographic representation of a magnetic aperture and the resultant flux line geometry.
Figure 35B:
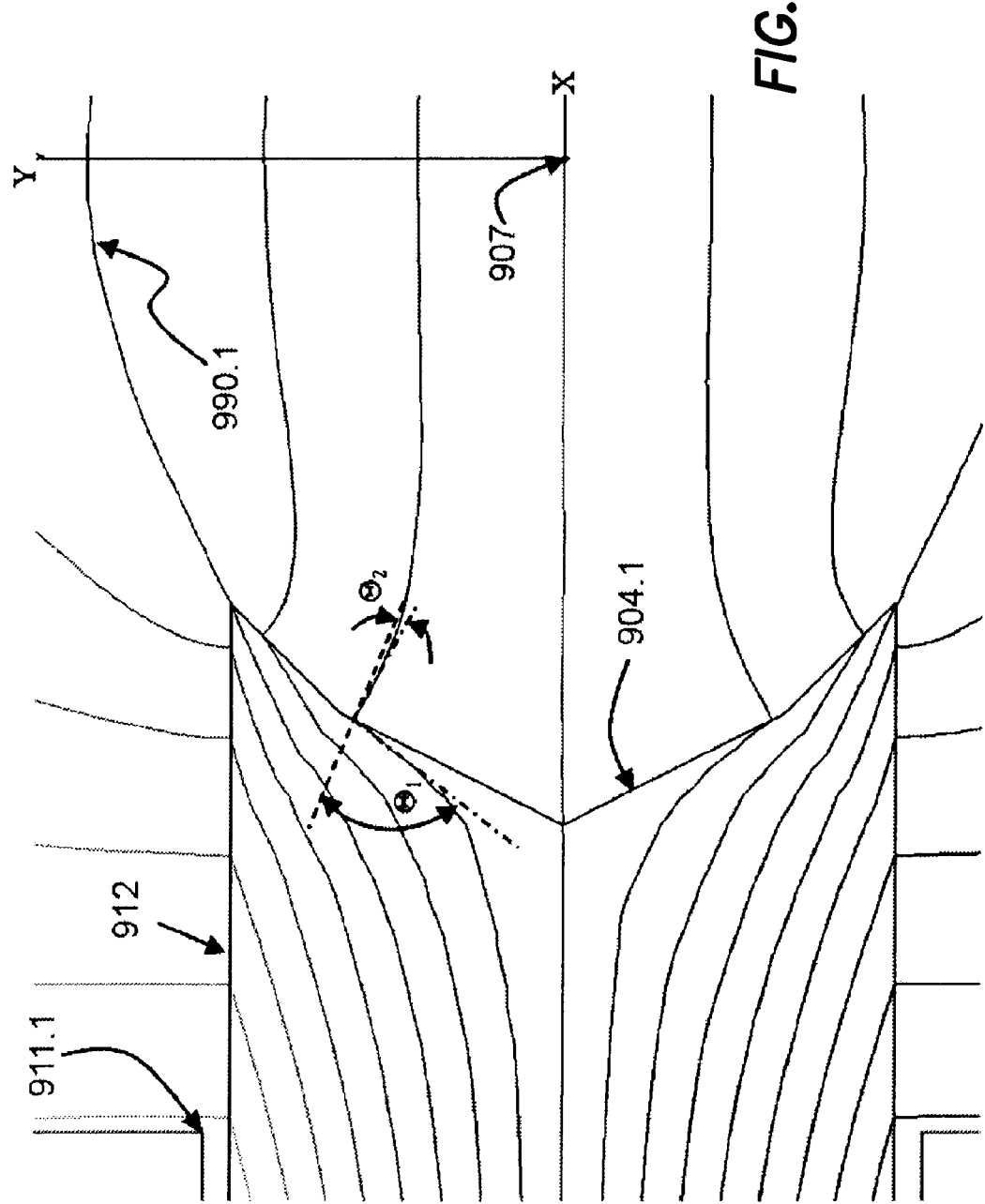
FIG. 35B is an orthographic representation of the refraction index generated by a magnetic aperture.

FIGS. 35A & 35B are schematic representations of the preferred embodiments of the newly configured magnetic cavity, whereby a formation of the magnetic aperture 950, is depicted. Discontinuity of material properties, such as the permeability ($\mu$>1000) of the ferrous materials, used in the magnetic field generator; coil 911.1, core 912.1, and pole face 904.1, and air,[with permeability $\mu$=1] within the operating region, which changes the refractive angle at the boundaries, as the magnetic energy (flux) leaves the ferrous material and enters the operating region 910. In the case of employing a dual core-coil arrangement, (shown in FIG. 35A, reference numerals 911.1, 911.2 and 912.1, 912.2), fitted with concave pole faces 904.1 & 904.2, the flux is directed back to the operating region focusing the flux distribution while forming a lens geometry. The lens geometry reference numerals 905.$_{x1}$ is indicative of the possible insertion of multiple geometric forms in support of different field configurations.

The flux lines generated, (e.g. 990.1), by the current in one coil 911.1 is not closed around the coil directly, but bend to follow the path through the core 912.1 of the other coil 911.2 and its core 912.2.

The general laws of electromagnetic wave propagation through materials of different permeability and magnetic properties are described by Snell's law of refraction. In its simplest form the law states that the relative angles of wave propagation in one media through the boundary of the second media depends on both the dielectric and magnetic properties of each media, jointly defining the index of refraction coefficient n($\omega$). The speed of the electromagnetic wave is given by c (speed of light), thus the speed of magnetic wave propagation in the media is inversely proportional to the index of refraction. This index can be expressed in terms of permittivity $\epsilon(\omega)$ and permeability $\mu(\omega)$. The permittivity and permeability of the mediums are related to the index of refraction by the relation of $\mu(\omega) \cdot \epsilon(\omega) = n^2(\omega)/c^2$. Now the Snell's law states:

$$n_1 \sin(\theta_1) = n_n \sin(\theta_2) \quad [18]$$

In a static ($\omega \approx 0$) magnetic structure we can write for the general relation:

$$\frac{B_{1t}}{\mu_1} = \frac{B_{2t}}{\mu_2} \text{ if } J_s = 0 \quad [19]$$

Where subscript 1t and 2t stands for the tangential components of B on both sides of the boundary. The tangential components of B are discontinuous regardless of any current density at the interface. This discontinuity is related to the permeability of the two mediums. As a direct consequence of the above interface conditions, the magnetic field (either H or B) is refracted at the interface between the two materials (magnetic steel and air) with different permeability ($\mu_{steel}$>>1000 and $\mu_{air}$=1)

$$\tan\theta_1 = \frac{H_{1t}}{H_{1n}} \text{ and } \tan\theta_2 = \frac{H_{2t}}{H_{2n}} \quad [20]$$

Where t stands for tangential component and n for normal component. Substituting H=B/$\mu$ and $B_{1n}=B_{2n}$ we obtain $$\frac{\tan\theta_1}{\tan\theta_2} = \frac{\mu_1}{\mu_2} \quad [21]$$

Equation [18] and [19] correspond to a common interpretation of a relativistic wave propagation dynamics and its salient case of a nonrelativistic static perspective. The static solution derived from FIG. 35B calculates as follows:

$$\theta_1 = 80° \quad \mu_1 = 1000 \quad \mu_2 = 1 \quad \tan\theta_2 = \frac{\mu_2}{\mu_1 \cdot \tan\theta_1} \text{ thus } \theta_2 < 1° \quad [22]$$

Thus, the magnetic flux exits the pole face 904.X nearly perpendicularly and is directed from the concave-shaped surface, (magnetic aperture 904.1 & 904.2) into the operating region.

A further improvement, and another embodiment of the above shaped pole face focusing is to add a cylindrical core 912.1 & 912.2 to the otherwise isotropic magnetic steel core of coils 911.1 and 911.2. The added core 912, has a permeability value $\mu$=10. This embodiment of varying the permeability values, by incorporating different materials with variable $\mu$. Is an additional method in utilizing anisotropy in magnetic properties to shape the resulting magnetic field(s) geometry on demand.

Figure 35C:
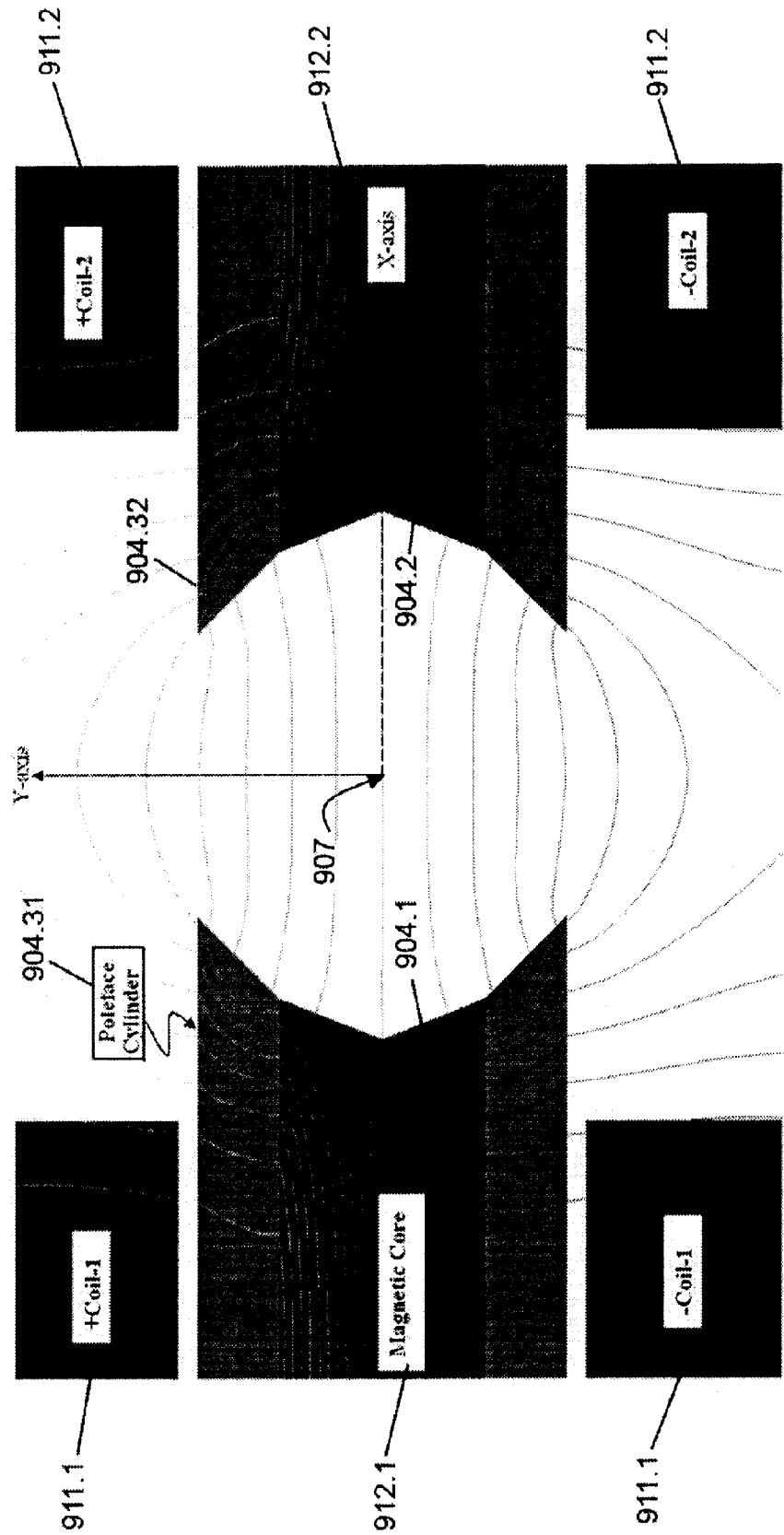
FIG. 35C is a graphic depiction the magnetic capsule aperture geometry layout.

FIG. 35C is a graphic depiction of flux line geometry where the magnetic aperture 950, formed out of items 904.1 & 904.2 direct the EM radiation by narrowing the trajectory due to cores 912.1 & 912.2 action resulting from the narrowing of the flux line geometry representing the magnetic energy or flux density formation as predicted by the Snell's law formalism. The inner region is illustrated in FIG. 35C with eleven flux lines enveloping the operating magnetic lens. The pole face cylinder 912.2, bends the flux lines toward the center allowing focused enhancement of the flux density at the crossing of the X and Y axis. Due to the anisotropy of the magnetic property (permeability) across the core, the magnetic aperture 950, narrows and flux density increases at the center. The core 912.1 & 912.2 now consists of a core cylinder with material permeability of $\mu$=1000, a outer cylinder material permeability of $\mu$=10, projecting the flux vector into the region of air with $\mu$=1.

Figure 36:
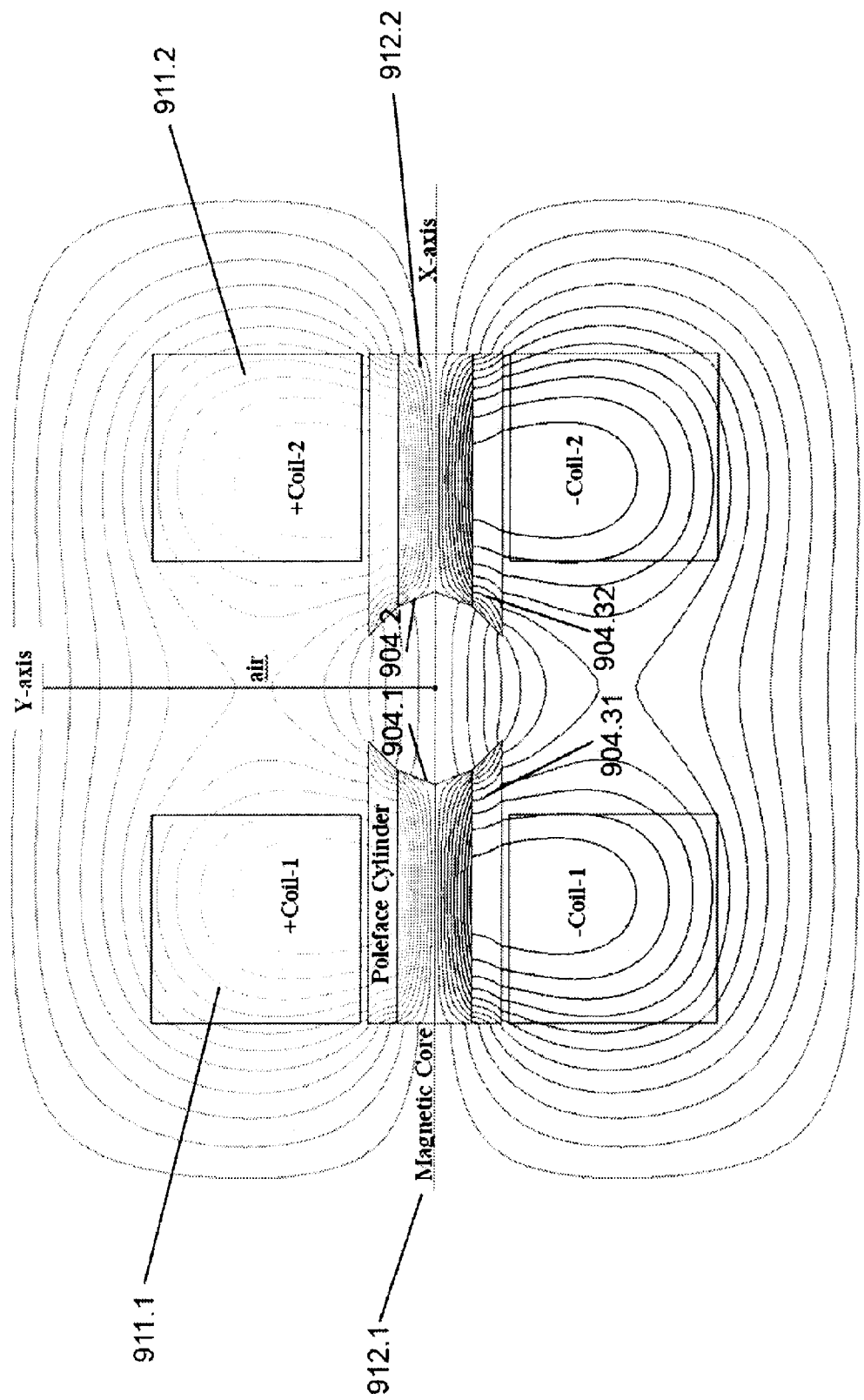
FIG. 36 is an orthographic depiction of the directional and flux density map.

FIG. 36 is a graphic representation of an embodiment whereby further improvement of the flux-focusing and aperture control of the inner operating region is presented. The pole face cylinder 904.31 & 904.32 are replaced with much narrower and smaller concentric cylindrical shaped cores 904.3$x_1$ & 904.3$x_2$ around the pole face 904.1 & 904.2. The coils 911, are fitted with high permeability magnetic steel ($\mu$>1000) under them, while the pole face 904.1 & 904.2 are divided into a high permeability (($\mu$>1000) inner core 912.1 & 912.2 and a low permeability (($\mu$>10) outer core 904.3$x_1$ & 904.3$x_2$. This division makes the pole face 904.1 & 904.2 behave as an anisotropic core shaping the flux even more, to bend the magnetic flux line geometry toward the central operating region.

Figure 36A:
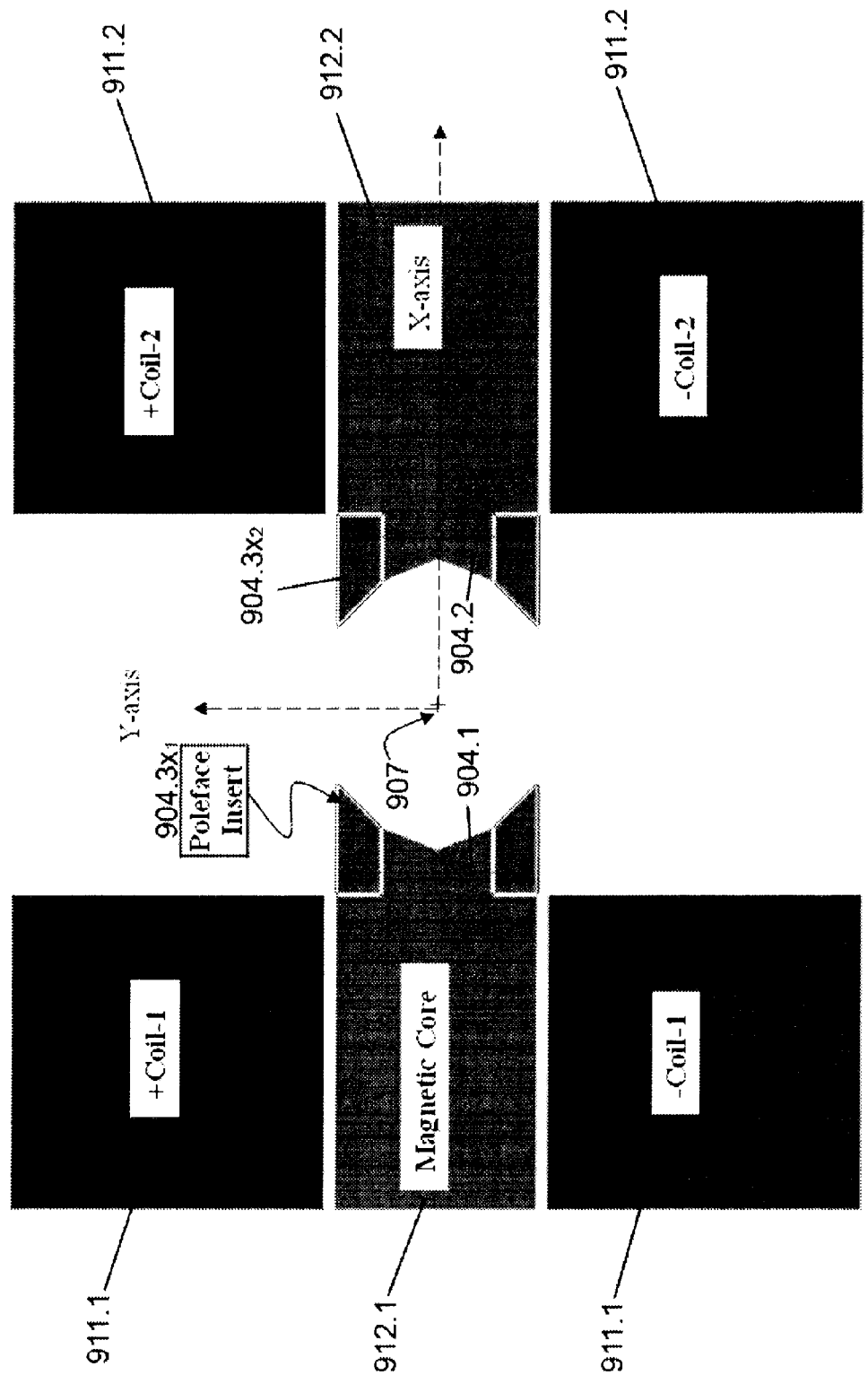
FIG. 36A is an orthographic depiction of the pole face cylindrical insert layout.
Figure 36B:
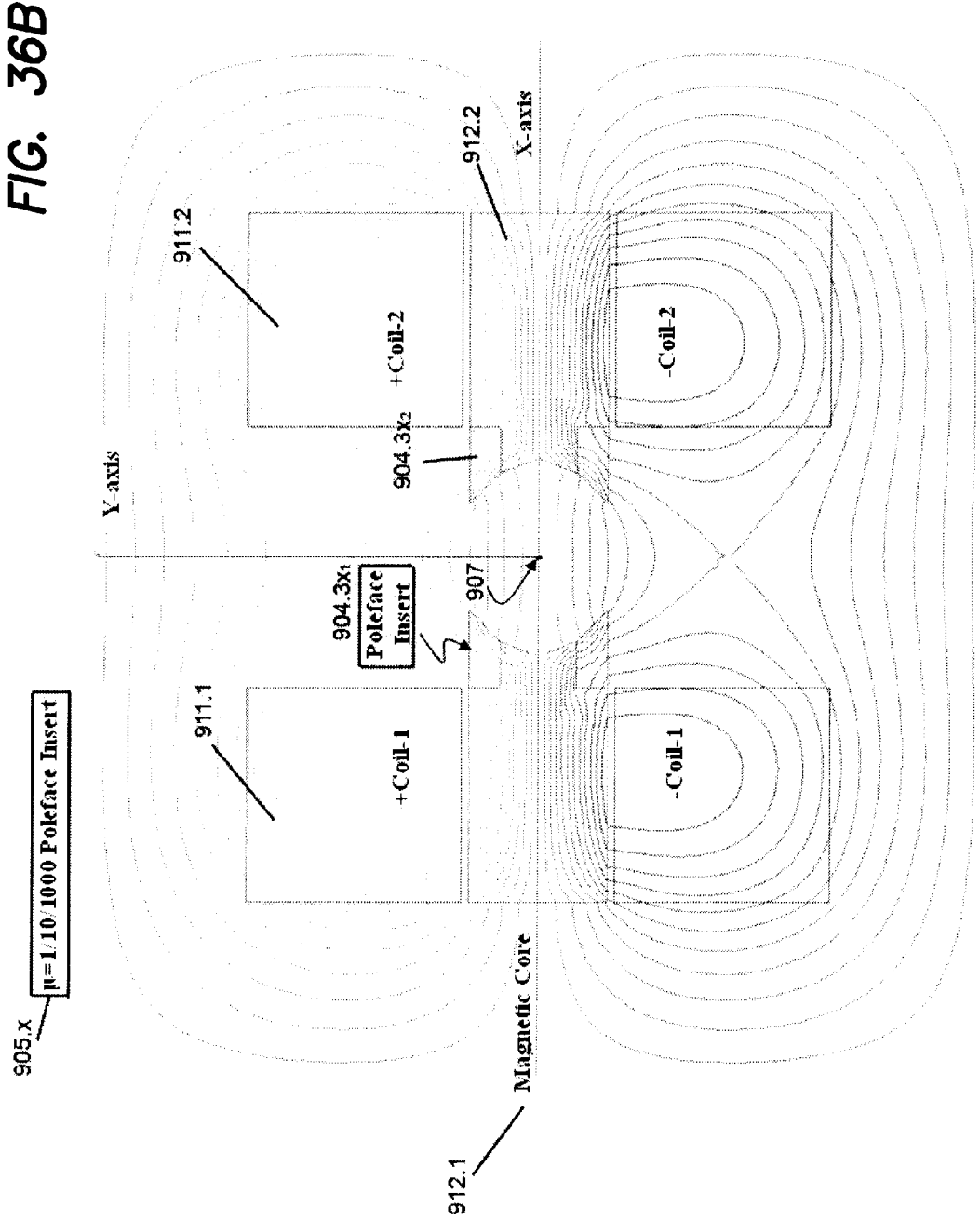
FIG. 36B is an orthographic representation of the directional and flux density map with relative permeability constants.

FIGS. 36A and 36B are orthographic depictions of the directional and flux density map whereby an equal or better performance characteristics of the "lensing" results, is presented by employing the segmented pole face 904.1 & 904.2 rings are inserted 904.3$x_1$ and 904.3$x_2$ as indicated by FIGS. 36A and 36B. This arrangement is modular and provides for insertion of different refraction indices based on demand or specificity of the task at hand. This method of combining the inserts 904.3$x_1$ & 904.3$x_2$ as low permeability ring arrangement improve the anisotropic geometry to "condense" the flux line density, while shifting the center of focus on demand. Experimental evaluation confirms better results of increased narrowing and focused flux through the magnetic lens 905.$x_2$, due to segmented or hybrid pole face material permeability.

FIG. 36B is a graphic representation of the directional and flux density map indicating equal or better performance with the segmented pole face ring insertion with different permeability values e.g. $\mu=1$, $\mu=10$, and $\mu=1000$. This arrangement of segmented hybrid permeability performs better as an aperture narrowing and focusing the flux.

FIG. 36C is a graphic representation of the magnetic aperture 950, whereby a hybrid permeability of different materials is forming the aperture to achieve a field focusing. The coil 911.1 is fitted with a magnetic core 912.1 with $\mu=1000$, (reference numeral 905.$x3$), the magnetic aperture 950, is augmented with a pole face insert with 904.$3x_1$ $\mu=10$ (reference numeral 905.$x_3$). The effective operating area has the permeability value $\mu=1$, (reference numeral 905.$x_i$), the resulting directional and flux density map is graphically shown in view "A". The combination of pole face geometry, 904.$3xy$ with different permeability values, 905.$x_y$ is the reason by which the magnetic cavity's lensing ability is improved.

The static solution derived from FIGS. 36C and 36D is calculated as follows:

$$\theta_1 = 45° \ \mu_1 = 1000 \ \mu_2 = 1 \ \tan\theta_2 = \frac{\mu_2}{\mu_1 \cdot \tan\theta_1} \quad [23]$$

$$\text{thus } \theta_2 = 0.65°$$

Thus, the magnetic flux again exits the pole face with close to perpendicular pointing from the concave-shaped surface into the operating region 910. The standing wave front is altered based on combination of material permeability's: 905.$x_y$ [$\mu=1$, $\mu=10$, $\mu=1000$.] and pole face geometry: 904.$x$.

We teach the use of magnetic aperture with its use of permeability inserts so as to demonstrate the marked improvements in using the "lensing" technique while guiding and controlling an untethered device and specifically in employing such method for diagnostic and therapeutic magnetic propulsion vessel as instructed by the MGCE system.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

We claim:

1. An apparatus for guiding a magnetic propulsion capsule through a lumen of a patient comprising:
    a first plurality of paired electromagnets disposed circumferentially with respect to a longitudinal axis around a magnetic chamber, each pair of the first plurality of electromagnets aligned with each other along an axis radial to the longitudinal axis, wherein each of the first plurality of paired electromagnets comprises an AC coil and a DC coil;
    a second plurality of paired electromagnets disposed along the longitudinal axis around the magnetic chamber, each pair of the second plurality of electromagnets aligned with each other along an axis parallel to the longitudinal axis;
    a retractable operating table capable of being adjustably inserted into the magnetic chamber for selectively positioning the patient along the longitudinal axis in the magnetic chamber; and
    a control center coupled to the first and second plurality of paired electromagnets and operating table.

2. The apparatus of claim 1 where each of the first plurality of paired electromagnets comprise an AC electromagnetic coil stacked with a DC electromagnetic coil.

3. The apparatus of claim 1 where each of the second plurality of paired electromagnets are comprised of a ring electromagnet.

4. The apparatus of claim 1 further comprising circular shielding circumferentially disposed around the first and second plurality of paired electromagnets to collect stray magnetic field lines.

5. The apparatus of claim 1 where the second plurality of paired electromagnets are arranged and configured by the control center to generate a levitating force on the capsule arising from Lenz' law.

6. The apparatus of claim 1 where each of the first plurality of paired electromagnets each comprise an AC and a DC coil formed together on a corresponding common laminate core, each electromagnet arranged and configured by the control center to produce a mixed AC and DC magnetic field having a constant amplitude carrier DC magnetic field at a carrier frequency modulated by an AC alternating magnetic pulse field.

7. The apparatus of claim 1 where the first and second plurality of paired electromagnets are arranged and configured by the control center to define the magnetic chamber in the form of a three dimensional closed magnetic cavity, where energy efficiency is maximized due to low magnetic loss in the magnetic cavity, symmetry and a degree of homogeneity of a magnetic field in the magnetic cavity, and where a defined magnetic field pattern is dynamically moveable in the magnetic cavity relative to a location of the capsule.

8. An apparatus for guiding a magnetic propulsion capsule through a lumen of a patient comprising:
  a first plurality of paired electromagnets disposed circumferentially with respect to a longitudinal axis around a magnetic chamber, each pair of the first plurality of electromagnets aligned with each other along an axis radial to the longitudinal axis, wherein each of the first plurality of paired electromagnets comprises an AC coil and a DC coil;
  a second plurality of paired electromagnets disposed along the longitudinal axis around the magnetic chamber, each pair of the second plurality of electromagnets aligned with each other along an axis parallel to the longitudinal axis;
  a retractable operating table capable of being adjustably inserted into the magnetic chamber for selectively positioning the patient along the longitudinal axis in the magnetic chamber;
  a sensor for sensing the capsule's position and orientation;
  and a control center coupled to the sensor; the first and second plurality of paired electromagnets; and the operating table to provide control of a magnetic field generated by the first and second plurality of paired electromagnets in the magnetic chamber using a closed servo-loop modality with the capsule's sensed position and orientation.

9. The apparatus of claim 8 where the control center comprises a controller and a work station coupled to the controller for providing a user interface including a haptic controller and a joystick to allow direct control of the capsule, the work station and controller bidirectionally communicated with each other for real-time transmission of parameters and commands using a fixed packet protocol, the controller providing regulation of currents provided to the first and second plurality of paired electromagnets and the position of the operating table in response to navigation commands received from the work station to magnetically position the capsule to a user selected location, the controller wirelessly receiving position and orientation information from the capsule.

10. The apparatus of claim 9 where the joystick comprises a virtual capsule user input device with inputs to control the position, orientation, and rotation of the capsule within the magnetic cavity coupled to the control center to control the first and second plurality of paired electromagnets to effect motion of capsule and to provide force feedback to provide tactile indications that the capsule has encountered an obstruction for closed servo loop modality.

11. The apparatus of claim 9 where the work station and controller intercommunicated using a method comprising:
  initiating communication with the controller through a repeated sequential CallBack interrupts;
  compensating for any variation of elapsed time between sequential CallBack interrupts using a precision performance timer to determine a precise elapsed time from a previous CallBack interrupt;
  assembling a packet to be sent to the work station which packet includes information relating to an elapsed time since the last CallBack interrupt, the position and orientation of the capsule and at least one system health field;
  receiving the assembled packet on the work station from the controller;
  parsing and interpreting the information received and interpreted in corresponding work station subsystems;
  sending position and orientation information to a haptic controller handler which computes force feedback (FFB) direction and magnitude;
  updating the haptic controller using the FFB settings;
  processing the received packet by a user interface (UI) handler which updates the appropriate UI elements to reflect current input navigation system settings and states;
  collecting information required for response by the controller to current navigation system settings and states; and
  returning the collected information to the controller for execution.

12. An apparatus for guiding a magnetic propulsion capsule through a body lumen of a patient comprising a plurality of paired electromagnets disposed circumferentially with respect to a longitudinal axis around a magnetic chamber, each pair of the plurality of electromagnets aligned with each other along an axis radial to the longitudinal axis, the plurality of paired electromagnets arranged and configured to produce an inverted magnetic gradient vortex by fusing the fields from each of the plurality of paired electromagnets to rotate and translate the capsule along a center portion of the chamber enabling a full six degrees of freedom of movement of the capsule within a body lumen in three dimensional space,
  wherein each of the plurality of electromagnets comprises an AC coil stacked with a DC coil.

13. An apparatus for guiding a magnetic propulsion capsule through a lumen of a patient comprising:
  a plurality of paired electromagnets disposed circumferentially with respect to a longitudinal axis around a magnetic chamber, each pair of the plurality of electromagnets aligned with each other along an axis radial to the longitudinal axis;
  a retractable operating table capable of being adjustably inserted into the magnetic chamber for selectively positioning the patient along the longitudinal axis in the magnetic chamber; and
  a control center coupled to the plurality of paired electromagnets and the operating table,
  where each of the electromagnets comprises an AC coil stacked with a DC coil, a magnetically permeable core, a permeable pole face and a permeable pole face insert collectively providing a shaped magnetic field.

14. The apparatus of claim 13 where each of the paired electromagnets comprise a pole face that is provided with a concave shape oriented toward the opposing electromagnet of the pair to direct a flux to an operating region.

15. The apparatus of claim 13 where the magnetically permeable core is comprised of a permeable steel ring with a first permeability and a shaped inner concentric permeable core with a second permeability to utilize magnetic anisotropy of the magnetically permeable core to shape a resulting magnetic field geometry.

16. The apparatus of claim 13 where the magnetically permeable core is comprised of a permeable steel ring with a first permeability and a plurality of nested shaped inner concentric permeable cores each with corresponding selected permeabilities to utilize magnetic anisotropy of the magnetically permeable core to shape a resulting magnetic field geometry.

17. The apparatus of claim 15 further comprising a modular and interchangeable permeable, shaped, segmented pole face ring concentrically disposed about a pole face of the shaped inner concentric core.

* * * * *